US008846036B2

(12) United States Patent
Birkenmeyer et al.

(10) Patent No.: US 8,846,036 B2
(45) Date of Patent: *Sep. 30, 2014

(54) ANTIBODIES THAT BIND TO MAMMALIAN NGAL AND USES THEREOF

(75) Inventors: Larry G. Birkenmeyer, Glenview, IL (US); Suresh M. Desai, Libertyville, IL (US); David J. Hawksworth, Lake Villa, IL (US); Edward T. Olejniczak, Grayslake, IL (US); Qiaoqiao Ruan, Round Lake, IL (US); Robert W. Siegel, Fountaintown, IN (US); Sergey Y. Tetin, Lindenhurst, IL (US); Bryan C. Tieman, Elmhurst, IL (US); Bailin Tu, Libertyville, IL (US); Joan D. Tyner, Beach Park, IL (US); Lowell Tyner, legal representative, Chicago, IL (US); Robert N. Ziemann, Lindenhurst, IL (US); Frank C. Grenier, Libertyville, IL (US); Ryan F. Workman, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 420 days.

This patent is subject to a terminal disclaimer.

(21) Appl. No.: 12/329,357

(22) Filed: Dec. 5, 2008

(65) Prior Publication Data

US 2009/0263894 A1  Oct. 22, 2009

Related U.S. Application Data

(63) Continuation-in-part of application No. 12/104,408, filed on Apr. 16, 2008, now abandoned, and a continuation-in-part of application No. 12/104,410, filed on Apr. 16, 2008, now abandoned, and a continuation-in-part of application No. 12/104,413, filed on Apr. 16, 2008, and a continuation of application No. PCT/US2008/080340, filed on Oct. 17, 2008.

(60) Provisional application No. 60/981,473, filed on Oct. 19, 2007, provisional application No. 60/981,471, filed on Oct. 19, 2007, provisional application No. 60/981,470, filed on Oct. 19, 2007.

(51) Int. Cl.
*A61K 38/00* (2006.01)
*C07K 16/18* (2006.01)

(52) U.S. Cl.
CPC ............ *C07K 16/18* (2013.01); *C07K 2317/55* (2013.01); *C07K 2317/92* (2013.01); *C07K 2317/34* (2013.01)
USPC .............. 424/130.1; 424/141.1; 424/133.1; 530/387.1; 530/387.3; 530/388.1

(58) Field of Classification Search
CPC ............... G01N 33/6893; C12Q 2600/158; C12Q 1/6883; C07K 14/47; C07K 2317/565; C07K 2317/56
See application file for complete search history.

(56) References Cited

U.S. PATENT DOCUMENTS

| | | | |
|---|---|---|---|
| 5,876,950 A | 3/1999 | Siadak et al. | |
| 6,136,526 A | 10/2000 | Venge | |
| 6,447,989 B1 | 9/2002 | Comper et al. | |
| 7,056,702 B2 * | 6/2006 | Villanueva et al. | 435/70.21 |
| 7,435,804 B2 | 10/2008 | Kordyum et al. | |
| 7,659,378 B2 | 2/2010 | Han et al. | |
| 2003/0100060 A1 | 5/2003 | Fulton et al. | |
| 2003/0175686 A1 | 9/2003 | Rose et al. | |
| 2005/0272101 A1 | 12/2005 | Devarajan et al. | |
| 2006/0088908 A1 | 4/2006 | Skerra et al. | |
| 2006/0105389 A1 | 5/2006 | Kordyum et al. | |
| 2008/0038257 A1 | 2/2008 | Han et al. | |
| 2009/0123946 A1 * | 5/2009 | Birkenmeyer et al. | 435/7.21 |
| 2009/0124022 A1 * | 5/2009 | Birkenmeyer et al. | 436/501 |
| 2009/0169547 A1 | 7/2009 | Sahin et al. | |

FOREIGN PATENT DOCUMENTS

| | | |
|---|---|---|
| EP | 0756708 B1 | 7/2001 |
| EP | 1616184 B1 | 1/2006 |
| EP | 1766395 B1 | 3/2007 |
| EP | 1831699 B1 | 9/2007 |
| EP | 2035835 B1 | 3/2009 |
| EP | 2128625 A2 | 12/2009 |
| WO | WO/97/44460 | 11/1997 |
| WO | 03/029463 A2 | 4/2003 |
| WO | WO/03/080672 | 10/2003 |
| WO | 03/101283 A3 | 11/2003 |
| WO | 2004/005540 A2 | 1/2004 |
| WO | WO/2004/005544 | 1/2004 |
| WO | WO/2004/088276 | 10/2004 |

(Continued)

OTHER PUBLICATIONS

Grenier, et al: "Multi-site evaluation of an assay in development for NGAL (Neutrophil Gelatinase-Associated Lipocalin) on the Abbott Architect® Analyzer," Clinical Chemistry, vol. 54, No. 6, pp. Suppl-A170 (Jun. 2008).

(Continued)

*Primary Examiner* — Sean Aeder
*Assistant Examiner* — Julie Wu
(74) *Attorney, Agent, or Firm* — Audrey L. Bartnicki; Jennifer L. Wahlsten; Emily M. Haliday

(57) ABSTRACT

The present invention relates to antibodies specific for glycosylated mammalian NGAL, and to methods of making and using such antibodies.

28 Claims, 25 Drawing Sheets

(56) References Cited

FOREIGN PATENT DOCUMENTS

| WO | WO/2005/107793 | | 11/2005 |
|---|---|---|---|
| WO | WO/2005/121788 | | 12/2005 |
| WO | 2006/056464 | A2 | 6/2006 |
| WO | WO/2006/066587 | | 6/2006 |
| WO | 2006/086638 | A2 | 8/2006 |
| WO | 2007/044994 | A2 | 4/2007 |
| WO | 2007/098102 | A2 | 8/2007 |
| WO | WO/2007/137584 | | 12/2007 |
| WO | WO 2009052392 | A1 * | 4/2009 |
| WO | WO/2010/058378 | | 5/2010 |

OTHER PUBLICATIONS

Kjeldsen, et al: "Human neutrophil gelatinase-associated lipocalin and homologous proteins in rat and mouse," Biochimica et Biophysica Acta, vol. 1482, No. 1-2, pp. 272-283 (Oct. 18, 2000).
Kjeldsen, et al: "Identification of Neutrophil Gelatinase-Associated Lipocalin as a Novel Matrix Protein of Specific Granules in Human Neutrophils," Blood, vol. 83, No. 3, pp. 799-807 (Feb. 1, 1994).
Kjeldsen, et al: "Characterization of two ELISAs for NGAL, a newly described lipocalin in human neutrophils" Journal of Immunological Methods, vol. 198, No. 2, pp. 155-164 (Nov. 13, 1996).
Kjeldsen, et al: "Isolation and Primary Structure of NGAL, A Novel Protein Associated With Human Neutrophil Gelatinase," Journal of Biological Chemistry, vol. 268, No. 14, pp. 10425-10432 (May 15, 1993).
PCT/US2008/080325, International Search Report and the Written Opinion of the International Searching Authority, or the Declaration, Mailed Mar. 3, 2009.
PCT/US2008/080331, International Search Report and the Written Opinion of the International Searching Authority, or the Declaration, Mailed Mar. 9, 2009.
PCT/US2008/080340, International Search Report and the Written Opinion of the International Searching Authority, or the Declaration, Mailed Mar. 9, 2009.
"Quantikine. Human Lipocalin-2/NGAL Immunoassay," (Internet Citation), Retrieved from the Internet on Jul. 4, 2007: URL:http://www.rndsystems.com/pdf/DLCN20.pdf.
Rudd, et al: "Glycosylation of natural human neutrophil gelatinase B and neutrophil gelatinase B-associated lipocalin," Biochemistry 19991019 American Chemical Society US, vol. 38, No. 42, pp. 13937-13950 (Oct. 19, 1999).
Yan, et al: "The high molecular weight urinary matrix metalloproteinase (MMP) activity is a complex of gelatinase B/MMP-9 and neutrophil gelatinase-associated lipocalin (NGAL). Modulation of MMP-9 activity by NGAL.Modulation of MMP-9 Activity by NGAL," Journal of Biological Chemistry, American Society of Biolochemical Biologists, vol. 276, No. 40, pp. 37258-37265 (Oct. 5, 2001).
Alere Triage Product Insert, Dated 2011, downloaded 2012; pp. 1-24.
Antibodyshop O14a Product Specification "Anti-NGAL (human, neutrophil gelatinase associated lipocalin) Mouse monoclonal antibody," Product No. HYB 211-01. Mar. 31, 2009; One Page.
Antibodyshop O14b Product Specification "Anti-NGAL (human, neutrophil gelatinase associated lipocalin) Mouse monoclonal antibody, biotinylated," Product No. HYB 211-01 B. Mar. 31, 2009; One Page.
Antibodyshop 14c Product Specification "Anti-NGAL (human, neutrophil gelatinase associated lipocalin) Mouse monoclonal antibody," Product No. HYB 211-02. Apr. 14, 2009; One Page.
Antibodyshop O14d Product Specification "Anti-NGAL (human, neutrophil gelatinase associated lipocalin) Mouse monoclonal antibody, biotinylated," Product No. HYB 211-02 B. Apr. 14, 2009; One Page.
Antibodyshop O14e Product Specification "Anti-NGAL (human, neutrophil gelatinase associated lipocalin) Mouse monoclonal antibody," Product No. HYB 211-05. Apr. 14, 2009; One Page.
Axelsson et al. (1995) "Studies of the release and turnover of a human neutrophil lipocalin," Scand J Clin Lab Invest 55:577-588.
Bangert et al. (2005) "Urinary NGAL is dramatically increased in acute renal failure," Poster European Society of Intensive Care Medicine (ESICM), 18th annual congress—Amsterdam, Netherlands, Sep. 25-28, 2005 pp. 1-7; Abstract 242.
Bangert et al. (2006) "NGAL is significantly increased in urine and plasma in acute renal failure," Abstract 0023, ESICM, 19th annual congress—Barcelona, Spain; One Page.
Bennett et al. (2008) "Urine NGAL predicts severity of acute kidney injury after cardiac surgery: A prospective study," Clin J Am Soc Nephrol 3:665-673.
Bewick et al. (2004) "Statistics review 13: Receiver operating characteristic curves," Crit Care 8(6):508-512.
BioPorto. Announcement dated Sep. 22, 2005; One Page.
Blaser et al. (1995) "A sandwich enzyme immunoassay for the determination of neutrophil lipocalin in body fluids," Clinica Chimica Acta 235:137-145.
Cai et al. (2010) "The Origin of Multiple Molecular Forms in Urine of HNL/NGAL," Clinical Journal of the American Society of Nephrology 5:2229-2235.
Daemen et al. (1999) "Inhibition of apoptosis induced by ischemia-reperfusion prevents inflammation.," J. Clin. Invest. 104:541-549.
Declaration by Prof. Dr. Schulze-Lohoff (English translation) Oct. 4, 2012 "Research on NGAL biomarker"; pp. 1-2.
Declaration by Professor John Kellum, M.D. dated Sep. 28, 2011 and Dr. Kellum's CV dated Apr. 11, 2011.
Declaration of Dr. Devarajan dated Feb. 13, 2007 and filed during examination proceedings of U.S. Appl. No. 11/096,113; pp. 1-6.
Dent et al. (2005) "NGAL: A Novel Early Biomarker of Renal Injury Following Cardiac Surgery," Journal of the American College of Cardiology 45(3):324A; Abstract # 1143-241.
Dent et al. (2007) "Plasma neutrophil gelatinase-associated lipocalin predicts acute kidney injury, morbidity and mortality after pediatric cardiac surgery: a prospective uncontrolled cohort study," Critical Care 11(6):R127(pp. 1-8).
Deshpande (1996) "Enzyme Immunoassays from Concept to Product Development," Chapter 9, Assay Development, Evaluation and Validation, in Chapman & Hall, NY pp. 1-90.
Devarajan (2005) "Novel biomarkers for the early prediction of acute kidney injury," Cancer Ther 3:477-488.
Devarajan (2007) "Emerging biomarkers of acute kidney injury," Contrib. Nephrol. 156:203-212.
Devarajan et al. (2003) "Gene expression in early ischemic renal injury: clues towards pathogenesis, biomarker discovery, and novel therapeutics," Molecular Genetics and Metabolism 80:365-376.
Dhamidharka et al. (2002) "Serum Cystatin C is Superior to Serum Creatinine as a Marker of Kidney Function: A Meta-Analysis," Amer. J. Kidney Diseases 40:221-226.
Dorland's Illustrated Medical Dictionary, 29th Edition. W.B. Saunders Company, New York (2000); pp. 1-6.
Dr. Devarajan's presentation Oct. 2004 entitled: "NGAL: A Novel Early Biomarker of Renal Injury Following Cardiac Surgery."
Elneihoum et al. (1996) "Leukocyte activation detected by increased plasma levels of inflammatory mediators in patients with ischemic cerebrovascular diseases," Stroke 27:1734-1738(pp. 1-10).
Elneihoum et al. (1997) "Leukocyte activation in atherosclerosis: correlation with risk factors," Atherosclerosis 131:79-84.
Emami et al. (1991) "Transient ischemia or heat stress induces a cytoprotectant protein in rat kidney.," Am J Physiology 260(4Pt2):F479-F485.
Flo et al. (2004) "Lipocalin 2 mediates an innate immune response to bacterial infection by sequestrating iron," Nature 432:917-921.
Forsblad et al. (2002) "Clinical manifestations of atherosclerosis in an elderly population are related to plasma neopterin, NGAL and endothelin-1, but not to Chlamydia pneumoniae serology," Int Angiol 21(2):173-179.
Friedl et al. (1999) "Neutrophil gelatinase-associated lipocalin in normal and neoplastic human tissues. Cell type specific pattern of expression," Histochem J. 31:433-441.
Goetz et al. (2002) "The Neutrophil Lipocalin NGAL Is a Bacteriostatic Agent that Interferes with Siderophore-Mediated Iron Acquisition," Molecular Cell 10:1033-43.

(56) References Cited

OTHER PUBLICATIONS

Grenier et al. (2010) "Evaluation of the Architect urine NGAL assay: Assay performance, specimen handling requirements and biological variability," *Clinical Biochemistry* 43(6):615-620.
Haase et al. (2009) "Accuracy of Neutrophil Gelatinase-Associated Lipocalin (NGAL) in Diagnosis and Prognosis in Acute Kidney Injury: A Systematic Review and Meta-analysis," *American Journal of Kidney Diseases* 54(6):1012-1024.
Haase et al. (2011) "The outcome of neutrophil gelatinase-associated lipocalin-positive subclinical acute kidney injury.," *J Am Coll Card* 57(17):1752-1761.
Han et al. (2002) "Kidney Injury Molecule-1 (KIM-1): A novel biomarker for human renal proximal tubule injury," *Kidney International* 62:237-244.
Henderson's Dictionary of Biological Terms (2000) 12th edition, Prentice Hall; pp. 1-4.
Hraba-Renevey et al. (1989) "SV40-induced expression of mouse gene 24p3 involves a post-transcriptional mechanism," *Oncogene* 4:601-608.
Human NGAL ELISA kit product insert, Kamiya Biomedical Company, K-Assay® Cat. No. KT-564; pp. 1-7; Aug. 22, 2009.
Hvidberg et al. (2005) "The endocytic receptor megalin binds the iron transporting neutrophil-gelatinase-associated lipocalin with high affinity and mediates its cellular uptake," *FEBS Letters* 579:773-777.
Kellum et al. (2002) "Developing a consensus classification system for acute renal failure," *Curr Opin Crit Care* 8:509-514.
Kristiansen et al. (2004) "A proteomic analysis of human bile," *Mol Cell Proteomics* 3:715-728.
Kunis et al. (2004) "Ngal (Neutrophil Gelatinase-Associated Lipocalin) as a Marker for Tubular Damage in Patients with Acute Tubular Necrosis (ATN).," Poster abstract 3709 published on Oct. 31, 2004; One Page.
Kunis, Cheryl L. Declaration and poster—Oct. 31, 2004 (American Society of Nephrology Meeting) with Exhibits A-D and Curriculum Vitae of Dr. Kunis; pp. 1-9.
Maack (1992) "Renal handling of proteins and polypeptides," Chapter 44 from *Handbook of Physiology*, Ed Windhager, published 1992 pp. 2039-2082.
Matthaeus et al. (2001) "Acute Ischemic Renal Failure Induces Expression of Neutrophil Gelatinase-Associated Lipocalin and Matrix Metalloproteinase-9 in Damaged Tubuli," *Kidney Blood Press Res* Abstract P268 p. 342.
Matthaeus et al. 2001 "Co-regulation of Neutrophil Gelatinase-Associated Lipocalin and Matrix Metalloproteinase-9 in the Postischemic Rat Kidney; Opponent I," *J. Am. Soc. Nephrol.* 12:787A (Abst. No. 4112).
Mehta et al. (2007) "Acute kidney injury network: report of an initiative to improve outcomes in acute kidney injury," *Crit Care* 11(2):R31(pp. 1-8).
Merck Manual, List of causes of Acute Renal Failure (ARF) and Acute Tubulointerstitial Nephritis (ATN), Dec. 2007; pp. 1-9.
Mishra et al. (2003) "Identification of neutrophil gelatinase-associated lipocalin as a novel early urinary biomarker for ischemic renal injury," *J Am Soc Nephrol* 14:2534-2543.
Mishra et al. (2004) "Neutrophil gelatinase-associated lipocalin: A novel early urinary biomarker for cisplatin nephrotoxicity," *Am J Nephrol* 24:307-315.
Mishra et al. (2005) "Neutrophil gelatinase-associated lipocalin (NGAL) as a biomarker for acute injury after cardiac surgery," *Lancet* 365:1231-1238.
Monier et al. (2000) "Gelatinase isoforms in urine from bladder cancer patients," *Clin. Chim. Acta* 299:11-23.
Mori et al. (2005) "Endocytic delivery of lipocalin-siderophore-iron complex rescues the kidney from ischemia reperfusion injury," *J Clin Invest* 115(3):610-621.
Mueller et al. (2003) "Urinary heat shock protein-72 excretion in clinical and experimental renal ischemia.," *Pediatr Nephrol* 18:97-99. Published online Dec. 19, 2002.

Muramatsu et al. (2002) "Early detection of cysteine rich protein 61 (CYR61, CCN1) in urine following renal ischemic reperfusion injury.," *Kidney Int* 62:1601-1610.
NGAL ELISA Kit 036. (2010) Download, BioPorto Diagnostics. pp. 1-14.
NGAL Rapid ELISA Kit 037. Revision NR2007-12-EN, BioPorto Diagnostics, Dec. 2007.
Nielsen et al. (1999) "Rectal dialysate and fecal concentrations of neutrophil gelatinase-associated lipocalin, interleukin-8, and tumor necrosis factor-a in ulcerative colitis," *Am J Gastroenterol* 94(10):2923-2928.
Ohlsson et al. (2003) "Increased circulating levels of proteinase 3 in patients with anti-neutrophilic cytoplasmic autoantibodies-associated systemic vasculitis in remission," *Clin Exp Immunol* 131:528-535.
Ohlsson et al. (2005) "Increased monocyte transcription of the proteinase 3 gene in small vessel vasculitis," *Clin Exp Immunol* 141:174-182.
Parikh et al. (2005) "NGAL and IL-18: Novel early sequential predictive biomarkers of acute kidney injury after cardiac surgery," Abstract ASNO5LI 1064a: contact view; One Page.
PCT International Search Report and Written Opinion dated May 18, 2006 issued in PCT/DK2005/000806.
Racusen LC (2001) "The morphologic basis of acute renal failure.," Book excerpt from '*Acute Renal Failure*' ed. by Molitoris BA, Finn WF, W.B. Saunders Co.pp. 1-12.
Ray et al. (2010) "Statistical evaluation of a biomarker.," *Anesthesiology* 112:1023-1040.
Rudikoff et al. (1982) "Single amino acid substitution altering antigen-binding specificity," *Proc. Nat. Acad. Sci. USA* 79:1979-1983.
Sack et al. (2000) "Diurnal changes in the pattern of the distribution of gelatinases and associated proteins in tear fluid. Evidence that the PMN cell is a major source of MMP activity in normal and pathological tear fluid," *Cornea* 19:(6) p. S119(pp. 1-2).
Salom et al. (2010) "Aqueous humor neutrophil gelatinase-associated lipocalin levels in patients with idiopathic acute anterior uveitis," *Mol Vision* 16:1448-1452.
Scherberich et al. (1992) "Biochemical and Immunological Properties of Urinary Angiotensinase A and Dipeptidylaminopeptidase IV Their Use as Markers in Patients with Renal Cell Injury," *Eur. J. Clin. Chem. Clin. Biochem.* 30:663-668.
Solberg (1994) "Establishment and Use of Reference Values," *Textbook of Clinical Chemistry*. 2nd Edition, Chapter 13 pp. 454-484.
Soni et al. (2010) "NGAL: a biomarker of acute kidney injury and other systemic conditions," *Int Urol Nephrol* 42:141-150.
Table Analysis of data presented in Table 2 of EP1831699: Table A parts 1, 2 and 3 (2011) pp. 1-8.
Table Analysis of data presented in Table 2 of EP1831699: Table A parts 1, 2 and 3 (2011) pp. 1-8 (includes patient Nos. 1, 11, 18, 29, 30, 41, 42, 45, 57, 72, 84, 86 and 91 and patient 49).
Tamura et al. (2000) "Structural Correlates of an Anticarcinoma Antibody: Identification of Specificity-Determining Residues (SDRs) and Development of a Minimally Immunogenic Antibody Variant by Retention of SDRs Only," *J Immunol* 164:1432-1441.
The NGAL Test Reagent Kit (ST001CA) (2011) Available online at www.bioporto.comlarticles/the_ngaUesUnstructions_for_use/the_ngaUest_cc_ivd_download_1; pp. 1-21.
Uttenthal (2005) "NGAL: a marker molecule for the distressed kidney," *Renal Disease, Clinical Laboratory Investigation (CLI)*, (www.cli-online.com). Nov. 2005; pp. 1-2.
Uttenthal (2007) "NGAL: how useful is the new marker of kidney damage," *Clinical Laboratory International (CLI)*(www.cli-online.com) pp. 1-4.
Weinberg et al. (1991) "The cell biology of ischemic renal injury," *Kidney Int.* 39:476-500.
Westerlund et al. (1996) "Human neutrophil gelatinase and associated lipocalin in adult and localized juvenile periodontitis," *J Dent Res* 75:1553-1563.
Wheeler et al. (2008) "Serum neutrophil gelatinase-associated lipocalin (NGAL) as a marker of acute kidney injury in critically ill children with septic shock," *Crit Care Med* 36(4):1297-1303.

(56) References Cited

OTHER PUBLICATIONS

Wu et al. (1998) "Analytical and clinical evaluation of new diagnostic tests for myocardial damage," *Clin Chim Acta* 272:11-21.

Xu et al. (1994) "The development of an assay for human neutrophil lipocalin (HNL)—to be used as a specific marker of neutrophil activity in vivo and vitro," *Journal of Immunological Methods* 171:245-252.

Xu et al. (1995) "Serum measurements of human neutrophil lipocalin (HNL) discriminate between acute bacterial and viral infections," *Scand. J Clin Lab Invest* 55:125-131.

Xu et al. (2000) "Lipocalins as biochemical markers of disease," *Biochim Biophys Acta* 1482:298-307.

Yoshida et al. (2002) "Global Analysis of Gene Expression in Renal Ischemia-Reperfusion in the Mouse," *Biochem Biophys Res Commun* 291:787-794.

Youssef (2012) "Urine neutrophil gelatinase-associated lipocalin and kidney injury in children with focal segmental glomerulosclerosis.," *Iran J Kidney Dis* 6:355-360.

Zappitelli et al. (2007) "Urine neutrophil gelatinase-associated lipocalin is an early marker of acute kidney injury in critically ill children: a prospective cohort study," *Crit Care* 11(4):R84 (pp. 1-11).

Zweig et al. (1993) "Receiver-Operating Characteristic (ROC) Plots: A Fundamental Evaluation Tool in Clinical Medicine," *Clin Chem* 39(4):561-577.

\* cited by examiner

Signal Peptide

*MPLGLLWLGL* *ALLGALHAQA* QDSTSDLIPA PPLSKVPLQQ

NFQDNQFQGK WYVVGLAGNA ILREDKDPQK MYATIYELKE

DKSYNVTSVL FRKKKCDYWI RTFVPGCQPG EFTLGNIKSY

PGLTSYLVRV VSTNYNQHAM VFFKKVSQNR EYFKITLYGR

TKELTSELKE NFIRFSKSLG LPENHIVFPV PIDQCIDGHH

HHHH

6X His Tag

Figure 1

Signal Peptide

*MPLGLLWLGL* *ALLGALHAQA* QDSTSDLIPA PPLSKVPLQQ

NFQDNQFQGK WYVVGLAGNA ILREDKDPQK MYATIYELKE

DKSYNVTSVL FRKKKCDYWI RTFVPGSQPG EFTLGNIKSY

PGLTSYLVRV VSTNYNQHAM VFFKKVSQNR EYFKITLYGR

TKELTSELKE NFIRFSKSLG LPENHIVFPV PIDQCIDGHH

HHHH

6X His Tag

Figure 3

```
ATGCCCCTAGGTCTCCTGTGGCTGGGCCTAGCCCTGTTGGGGGCTCTGCATGCCCAGGCCCA
GGACTCCACCTCAGACCTGATCCCAGCCCCACCTCTGAGCAAGGTCCCTCTGCAGCAGAACT
TCCAGGACAACCAATTCCAGGGGAAGTGGTATGTGGTAGGCCTGGCAGGGAATGCAATTCTC
AGAGAAGACAAAGACCCGCAAAAGATGTATGCCACCATCTATGAGCTGAAAGAAGACAAGAG
CTACAATGTCACCTCCGTCCTGTTTAGGAAAAAGAAGTGTGACTACTGGATCAGGACTTTTG
TTCCAGGTTGCCAGCCCGGCGAGTTCACGCTGGGCAACATTAAGAGTTACCCTGGATTAACG
AGTTACCTCGTCCGAGTGGTGAGCACCAACTACAACCAGCATGCTATGGTGTTCTTCAAGAA
AGTTTCTCAAAACAGGGAGTACTTCAAGATCACCCTCTACGGGAGAACCAAGGAGCTGACTT
CGGAACTAAAGGAGAACTTCATCCGCTTCTCCAAATCTCTGGGCCTCCCTGAAAACCACATC
GTCTTCCCTGTCCAATCGACCAGTGTATCGACGGCCATCATCACCATCACCAT
```

Figure 4

```
ATGCCCCTAGGTCTCCTGTGGCTGGGCCTAGCCCTGTTGGGGGCTCTGCATGCCCAGGCCCA
GGACTCCACCTCAGACCTGATCCCAGCCCCACCTCTGAGCAAGGTCCCTCTGCAGCAGAACT
TCCAGGACAACCAATTCCAGGGGAAGTGGTATGTGGTAGGCCTGGCAGGGAATGCAATTCTC
AGAGAAGACAAAGACCCGCAAAAGATGTATGCCACCATCTATGAGCTGAAAGAAGACAAGAG
CTACAATGTCACCTCCGTCCTGTTTAGGAAAAAGAAGTGTGACTACTGGATCAGGACTTTTG
TTCCAGGTTCGCAGCCCGGCGAGTTCACGCTGGGCAACATTAAGAGTTACCCTGGATTAACG
AGTTACCTCGTCCGAGTGGTGAGCACCAACTACAACCAGCATGCTATGGTGTTCTTCAAGAA
AGTTTCTCAAAACAGGGAGTACTTCAAGATCACCCTCTACGGGAGAACCAAGGAGCTGACTT
CGGAACTAAAGGAGAACTTCATCCGCTTCTCCAAATCTCTGGGCCTCCCTGAAAACCACATC
GTCTTCCCTGTCCCAATCGACCAGTGTATCGACGGCCATCATCACCATCACCAT
```

Figure 5

VH gene
GluValGlnLeuValGlu SerGlyGly GlyLeuVal GlnProGly GlySerLeu LysLeuSer CysAlaAla SerGlyPhe ThrPheAsn
GAGGTCCAG CTGGTGGAG TCTGGGGGA GGCTTAGTG CAGCCTGGA GGGTCCCTG AAACTCTCC TGTGCAGCC TCTGGATTC ACTTTCAAT
CTTCAGTC GACCACCTC AGACCCCT CCGAATCAC GTCGGACCT CCCAGGGAC TTTGAGAGG ACAGGTCGG AGACCTAAG TGAAAGTTA
AsnTyrTyr MetSerTrp ValArgGln ThrProGln ArgArgLeu GluTrpVal AlaTyrIle SerSerSer GlyGlySer ThrTyrTyr
AACTATTAC ATGTCTTGG GTTCGCCAG ACTCCAGAG AGGAGGCTG GAGTGGGTC GCATACATT AGTAGTAGT GGTGGTAGT ACCTACTAT
TTGATAATG TACAGAACC CAAGCGGTC TGAGGTCTC TCCTCCGAC CTCACCCAG CGTATGTAA TCATCATCA CCACCATCA TGGATGATA
SerAspSer ValArgGly ArgPheThr IleSerArg AspThrAla ArgAsnThr LeuTyrLeu GlnMetThr SerLeuLys SerGluAsp
TCAGACAGT GTGAGGGGT CGATTCACC ATCTCCAGA GACACTGCC AGGAACACC CTGTACCTG CAAATGACC AGTCTGAAG TCTGAGGAC
AGTCTGTCA CACTCCCCA GCTAAGTGG TAGAGGTCT CTGTGACGG TCCTTGTGG GACATGGAC GTTACTGG TCAGACTTC AGACTCCTG
ThrAlaMet TyrTyrCys AlaArgHis PheGlyAsp TyrSerTyr PheAspTyr TrpGlyGln GlyThrThr LeuThrVal SerSer
ACAGCCATG TATTACTGT GCAAGACAT TTTGGTGAT TACTCTTAC TTTGACTAC TGGGGCCAA GGCACCACT CTCACAGTC TCCTCA
TGTCGGTAC ATAATGACA CGTTCTGTA AAACCACTA ATGAGAATG AAACTGATG ACCCCGGTT CCGTGGTGA GAGTGTCAG AGGAGTa CDR H1 : Gly-Phe-Thr-Phe-Asn-Tyr-Tyr-Met-Ser
CDR H2 : Ile-Ser-Ser-Ser-Gly-Gly-Ser-Thr
CDR H3 : His-Phe-Gly-Asp-Tyr-Ser-Tyr-Phe-Asp-Tyr

Figure 9A

VL gene

| | | | | | | | | | |
|---|---|---|---|---|---|---|---|---|---|
| AspIleGln | MetThrGln | SerProAla | SerLeuSer | AlaSerVal | GlyGluThr | ValThrIle | ThrCysArg | AlaSerGln | AsnPheTyr |
| GACATCCAG | ATGACCCAG | TCTCCAGTC | TCCCTATCT | GCATCTGTG | GGAGAAACT | GTCACCATC | ACATGTCGA | GCAAGTGAG | AATTTTTAC |
| CTGTAGTC | TACTGGGTC | AGAGGTCAG | AGGGATAGA | CGTAGACAC | CCTCTTTGA | CAGTGGTAG | TGTACAGCT | CGTTCACTC | TTAAAAATG |
| SerTyrLeu | AlaTrpTyr | GlnGlnLys | GlnGlyLys | SerProGln | LeuLeuVal | TyrAsnAla | LysThrLeu | AlaGluGly | ValProSer |
| AGTTATTTA | GCATGGTAT | CAACAGAAA | CAGGGAAAA | TCTCCTCAG | CTCCTGGTC | TATAATGCA | AAAACCTTA | GCAGAAGGT | GTGCCGTCA |
| ArgPheSer | GlySerGly | SerGlyThr | GlnPheSer | LeuLysIle | LeuAsnSer | LeuGlnPro | AspPheGly | ThrTyrTyr | CysGlnHis |
| AGGTTCAGT | GGCAGTGGA | TCAGGCACA | CAGTTTTCT | CTGAAGATC | AACAGCCTG | CAGCCTGAA | GATTTTGGG | ACTTATTAC | TGTCAACAT |
| HisTyrAsp | IleProLeu | ThrPheGly | AlaGlyThr | LysLeuGlu | LeuLysArg | | | | |
| CATTATGAT | ATTCCGCTC | ACGTTCGGT | GCTGGGACC | AAGCTGGAG | CTGAAGCGG | | | | |
| GTAATACTA | TAAGGCGAG | TGCAAGCCA | CGACCCTGG | TTCGACCTC | GACTTCGCC | | | | |

CDR L1: Arg-Ala-Ser-Glu-Asn-Phe-Tyr-Ser-Tyr-Leu-Ala
CDR L2: Asn-Ala-Lys-Thr-Leu-Ala-Glu
CDR L3: Gln-His-His-Tyr-Asp-Ile-Pro-Leu-Thr

| | | | | | | | |
|---|---|---|---|---|---|---|---|
| LysIleGln | LeuValGln | SerGlyPro | GluLeuLys | LysProGly | GluThrVal | LysIleSer | CysLysAla | CysGlyTyr | ThrPheThr |
| AAGATCCAG | TTGGTGCAG | TCTGGACCT | GAACTGAAG | AAGCCTGGA | GAGACAGTC | AAGATCTCC | TGCAAGGCT | TCTGGGTAT | ACATTCACA |
| AsnTyrGly | MetAsnTrp | ValLysGln | AlaProGly | LysGlyLeu | LysTrpMet | GlyTrpIle | AsnIleAsn | ThrGlyGlu | ProThrTyr |
| AACTATGGA | ATGAACTGG | GTGAAGCAG | GCTCCAGGA | AAGGGTTTA | AAGTGGATG | GGCTGGATA | AACATCAAC | ACTGGAGAG | CCAACATAT |
| AlaGluGly | PheLysGly | ArgPheAla | PheSerLeu | GluThrSer | AlaThrThr | AlaPheLeu | GlnIleAsn | AsnLeuLys | AsnGluAsp |
| GCTGAAGGC | TTCAAGGGA | CGGTTTGCC | TTCTCTTTG | GAAACCTCT | GCCACCACT | GCCTTTTTG | CAGATCAAC | AACCTCAAA | AATGAGGAC |
| ThrAlaThr | TyrLeuCys | AlaArgAsp | SerTyrSer | GlyGlyPhe | AspTyrPhe | GlyGlyMet | ThrIleVal | ThrValSer | Ser |
| ACGGCTACA | TATCTCTGT | GCAAGAGAT | TCCTATTCG | GGGGCTTTT | GACTACTTT | GGCCAAGGC | ACGATTGTC | ACAGTCTCC | TCA |
| | | | | | | | | | AGT |

CDR H1 : Gly-Tyr-Thr-Phe-Thr-Asn-Tyr-Gly-Met-Asn
CDR H2 : Ile-Asn-Ile-Asn-Thr-Gly-Glu-Pro-Thr
CDR H3 : Asp-Ser-Tyr-Ser-Gly-Gly-Phe-Asp-Tyr

Figure 10A

```
VL
AspIleVal    MetThrGln    SerProSer    SerLeuSer    ValSerAla    GlyGluLys    ValThrLeu    SerCysLys    SerSerGln    SerLeuLeu
GACATTGTG    ATGACACAG    TCTCCATCC    TCCCTGAGT    GTGTCAGCA    GGAGAGAAG    GTCACTTTG    AGCTGCAAG    TCCAGTCAG    AGTCTGTTA
CTGTAACAC    TACTGTGTC    AGAGGTAGG    AGGGACTCA    CACGTCGT    CCTCTCTTC    CAGTGAAAC    TCGACGTTC    AGGTCAGTC    TCAGACAAT
IleSerGly    AsnGlnLys    AsnTyrLeu    AlaTrpTyr    GlnGlnLys    ProGlyGln    ProProLys    LeuLeuIle    TyrGlyAla    SerThrArg
ATCAGTGGA    GATCAAAAG    AACTACTTG    GCCTGGTAC    CAGCAGAAA    CCAGGGCAG    CCTCCTAAA    CTGTTGATC    TACGGGGCA    TCCACTAGG
TAGTCACCT    CTAGTTTTC    TTGATGAAC    CGGACCATG    GTCGTCTTT    GGTCCCGTC    GGAGGATTT    GACAACTAG    ATGCCCCGT    AGGTGATCC
AspSerGly    ValProAsp    ArgPheThr    GlySerGly    SerGlyAla    AspPheThr    LeuThrIle    SerSerVal    GlnAlaGlu    AspLeuAla
GACTCTGGG    GTCCCTGAT    CGGTTCACA    GGCAGTGGA    TCTGGAGCC    GATTTCACT    CTTACCATC    AGCAGTGTG    CAGGCTGAA    GACCTGGCA
CTGAGACCC    CAGGAGCTA    GCCAAGTGT    CCGTCACCT    AGACCTCGG    CTAAAGTGA    GAATGGTAG    TCGTCACAC    GTCCGACTT    CTGGACCGT
ValTyrTyr    CysGlnAsn    AspHisSer    PheProPro    ThrPheGly    AlaGlyThr    LysLeuArg
GTTTATTAC    TGTCAGAAT    GATCATAGT    TTCCCTCCC    ACGTTCGGT    GCTGGGACC    AAGCTGGAG    CTGAAACGG
CAATAATG     ACAGTCTTA    CTAGTATCA    AAGGGAGGG    TGCAAGCCA    CGACCCTGG    TTCGACCTC    GACTTTGCC

CDR L1 : Lys-Ser-Ser-Gln-Ser-Leu-Leu-Ile-Ser-Gly-Asp-Gln-Lys-Asn-Tyr-Leu-Ala
CDR L2 : Gly-Ala-Ser-Thr-Arg-Asp-Ser
CDR L3 : Gln-Asn-Asp-His-Ser-Phe-Pro-Pro-Thr
```

Figure 10B

```
    ATGCAGGACTCTACTTCCGACCTGATTCCGGCTCCGCCGCTGTCTAAAGTGCCGCTGCAG
 1  ------+---------+---------+---------+---------+---------+  60
     M  Q  D  S  T  S  D  L  I  P  A  P  P  L  S  K  V  P  L  Q

CAGAACTTTCAAGACAACCAGTTCCAGGGTAAATGGTACGTTGTGGGCCTGGCTGGTAAC
 61 ------+---------+---------+---------+---------+---------+ 120
     Q  N  F  Q  D  N  Q  F  Q  G  K  W  Y  V  V  G  L  A  G  N

GCGATCCTGCGTGAAGACAAAGATCCGCAGAAAATGTATGCTACCATCTACGAACTGAAA
121 ------+---------+---------+---------+---------+---------+ 180
     A  I  L  R  E  D  K  D  P  Q  K  M  Y  A  T  I  Y  E  L  K

GAAGACAAATCTTATAACGTGACCAGCGTTCTGTTTCGTAAAAAGAAATGTGACTACTGG
181 ------+---------+---------+---------+---------+---------+ 240
     E  D  K  S  Y  N  V  T  S  V  L  F  R  K  K  K  C  D  Y  W

ATTCGCACCTTCGTGCCGGGCTCTCAGCCGGGCGAGTTCACTCTGGGTAACATCAAATCT
241 ------+---------+---------+---------+---------+---------+ 300
     I  R  T  F  V  P  G  S  Q  P  G  E  F  T  L  G  N  I  K  S

TACCCGGGTCTGACTAGCTACCTGGTGCGTGTGGTTTCTACTAACTATAACCAGCATGCT
301 ------+---------+---------+---------+---------+---------+ 360
     Y  P  G  L  T  S  Y  L  V  R  V  V  S  T  N  Y  N  Q  H  A

ATGGTGTTCTTCAAGAAAGTTTCTCAGAACCGTGAATACTTCAAGATTACTCTGTACGGT
361 ------+---------+---------+---------+---------+---------+ 420
     M  V  F  F  K  K  V  S  Q  N  R  E  Y  F  K  I  T  L  Y  G

CGTACCAAAGAGCTGACCTCTGAGCTGAAAGAAAACTTCATCCGTTTCTCTAAATCTCTG
421 ------+---------+---------+---------+---------+---------+ 480
     R  T  K  E  L  T  S  E  L  K  E  N  F  I  R  F  S  K  S  L

GGCCTGCCGGAGAACCATATCGTGTTTCCGGTTCCGATCGATCAGTGCATCGACGGTCAT
481 ------+---------+---------+---------+---------+---------+ 540
     G  L  P  E  N  H  I  V  F  P  V  P  I  D  Q  C  I  D  G  H

CATCACCATCACCATTGA
541 ------+--------- 558
     H  H  H  H  H  *
```

Figure 14

SEQUENCE LISTING

```
<160> NUMBER OF SEQ ID NOS: 33

<210> SEQ ID NO 1
<211> LENGTH: 198
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: The first 20 amino acids are the signal peptide
      which would be labeled -1 to -20, with Gln (at position 21) being
      considered amino acid 1 of the NGAL peptide

<400> SEQUENCE: 1

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125
```

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
                180                 185                 190

Asp Gln Cys Ile Asp Gly
            195

<210> SEQ ID NO 2
<211> LENGTH: 198
<212> TYPE: PRT
<213> ORGANISM: Artificial sequence
<220> FEATURE:
<223> OTHER INFORMATION: Chemically synthesized
<220> FEATURE:
<221> NAME/KEY: MISC_FEATURE
<222> LOCATION: (1)..(20)
<223> OTHER INFORMATION: The first 20 amino acids are the signal peptide
      which would be labeled -1 to -20, with Gln (at position 21) being
      considered amino acid 1 of the NGAL peptide

<400> SEQUENCE: 2

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
                20                  25                  30

Leu Ser Lys Val Pro Leu Gln Gln Asn Phe Gln Asp Asn Gln Phe Gln
            35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Ser Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
                180                 185                 190

Asp Gln Cys Ile Asp Gly
            195

<210> SEQ ID NO 3
<211> LENGTH: 612
<212> TYPE: DNA
<213> ORGANISM: Homo sapiens

<400> SEQUENCE: 3
atgcccctag gtctcctgtg gctgggccta gccctgttgg gggctctgca tgcccaggcc        60

```
caggactcca cctcagacct gatcccagcc ccacctctga gcaaggtccc tctgcagcag    120
aacttccagg acaaccaatt ccaggggaag tggtatgtgg taggcctggc agggaatgca    180
attctcagag aagacaaaga cccgcaaaag atgtatgcca ccatctatga gctgaaagaa    240
gacaagagct acaatgtcac ctccgtcctg tttaggaaaa agaagtgtga ctactggatc    300
aggacttttg ttccaggttg ccagcccggc gagttcacgc tgggcaacat taagagttac    360
cctggattaa cgagttacct cgtccgagtg gtgagcacca actacaacca gcatgctatg    420
gtgttcttca agaaagtttc tcaaaacagg gagtacttca agatcaccct ctacggagaa    480
accaaggagc tgacttcgga actaaaggag aacttcatcc gcttctccaa atctctgggc    540
ctccctgaaa accacatcgt cttccctgtc ccaatcgacc agtgtatcga cggccatcat    600
caccatcacc at                                                      612

<210> SEQ ID NO 4
<211> LENGTH: 612
<212> TYPE: DNA
<213> ORGANISM: Artificial sequence
<220> FEATURE:
<223> OTHER INFORMATION: Chemically synthesized

<400> SEQUENCE: 4
atgcccctag gtctcctgtg gctgggccta gccctgttgg gggctctgca tgcccaggcc     60
caggactcca cctcagacct gatcccagcc ccacctctga gcaaggtccc tctgcagcag    120
aacttccagg acaaccaatt ccaggggaag tggtatgtgg taggcctggc agggaatgca    180
attctcagag aagacaaaga cccgcaaaag atgtatgcca ccatctatga gctgaaagaa    240
gacaagagct acaatgtcac ctccgtcctg tttaggaaaa agaagtgtga ctactggatc    300
aggacttttg ttccaggttc gcagcccggc gagttcacgc tgggcaacat taagagttac    360
cctggattaa cgagttacct cgtccgagtg gtgagcacca actacaacca gcatgctatg    420
gtgttcttca agaaagtttc tcaaaacagg gagtacttca agatcaccct ctacggagaa    480
accaaggagc tgacttcgga actaaaggag aacttcatcc gcttctccaa atctctgggc    540
ctccctgaaa accacatcgt cttccctgtc ccaatcgacc agtgtatcga cggccatcat    600
caccatcacc at                                                      612

<210> SEQ ID NO 5
<211> LENGTH: 357
<212> TYPE: DNA
<213> ORGANISM: Artificial sequence
<220> FEATURE:
<223> OTHER INFORMATION: Chemically synthesized

<400> SEQUENCE: 5
gaagtgcagc tggtggagtc tggggggaggc ttagtgcagc ctggagggtc cctgaaactc     60
tcctgtgcag cctctggatt cactttcaat aactattaca tgtcttgggt tcgccagact    120
ccagagagga ggctggagtg ggtcgcatac attagtagta gtggtggtag tacctactat    180
tcagacagtg tgaggggtcg attcaccatc tccagagaca ctgccaggaa caccctgtac    240
ctgcaaatga ccagtctgaa gtctgaggac acagccatgt attactgtgc aagacatttt    300
ggtgattact cttactttga ctactggggc caaggcacca ctctcacagt ctcctca       357

<210> SEQ ID NO 6
<211> LENGTH: 324
<212> TYPE: DNA
```

-continued

<213> ORGANISM: Artificial sequence
<220> FEATURE:
<223> OTHER INFORMATION: Chemically synthesized

<400> SEQUENCE: 6

```
gacatccaga tgactcagtc tccagcctcc ctatctgcat ctgtgggaga aactgtcacc    60
atcacatgtc gagcaagtga gaattttac agttatttag catggtatca acagaaacag   120
ggaaaatctc ctcagctcct ggtctataat gcaaaaacct tagcagaagg tgtgccgtca   180
aggttcagtg gcagtggatc aggcacacag ttttctctga agatcaacag cctgcagcct   240
gaagattttg ggacttatta ctgtcaacat cattatgata ttccgctcac gttcggtgct   300
gggaccaagc tggagctgaa gcgg                                          324
```

<210> SEQ ID NO 7
<211> LENGTH: 119
<212> TYPE: PRT
<213> ORGANISM: Artificial sequence
<220> FEATURE:
<223> OTHER INFORMATION: Chemically synthesized

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Asn Tyr
            20                  25                  30

Tyr Met Ser Trp Val Arg Gln Thr Pro Glu Arg Arg Leu Glu Trp Val
        35                  40                  45

Ala Tyr Ile Ser Ser Gly Gly Ser Thr Tyr Tyr Ser Asp Ser Val
    50                  55                  60

Arg Gly Arg Phe Thr Ile Ser Arg Asp Thr Ala Arg Asn Thr Leu Tyr
65                  70                  75                  80

Leu Gln Met Thr Ser Leu Lys Ser Glu Asp Thr Ala Met Tyr Tyr Cys
                85                  90                  95

Ala Arg His Phe Gly Asp Tyr Ser Tyr Phe Asp Tyr Trp Gly Gln Gly
            100                 105                 110

Thr Thr Leu Thr Val Ser Ser
        115

<210> SEQ ID NO 8
<211> LENGTH: 9
<212> TYPE: PRT
<213> ORGANISM: Artificial sequence
<220> FEATURE:
<223> OTHER INFORMATION: Chemically synthesized

<400> SEQUENCE: 8

Gly Phe Thr Phe Asn Tyr Tyr Met Ser
1               5

<210> SEQ ID NO 9
<211> LENGTH: 8
<212> TYPE: PRT
<213> ORGANISM: Artificial sequence
<220> FEATURE:
<223> OTHER INFORMATION: Chemically synthesized

<400> SEQUENCE: 9

Ile Ser Ser Ser Gly Gly Ser Thr
1               5

```
<210> SEQ ID NO 10
<211> LENGTH: 10
<212> TYPE: PRT
<213> ORGANISM: Artificial sequence
<220> FEATURE:
<223> OTHER INFORMATION: Chemically synthesized

<400> SEQUENCE: 10

His Phe Gly Asp Tyr Ser Tyr Phe Asp Tyr
1               5                   10

<210> SEQ ID NO 11
<211> LENGTH: 108
<212> TYPE: PRT
<213> ORGANISM: Artificial sequence
<220> FEATURE:
<223> OTHER INFORMATION: Chemically synthesized

<400> SEQUENCE: 11

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Phe Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Asp Ile Pro Leu
                85                  90                  95

Thr Phe Gly Ala Gly Thr Lys Leu Glu Leu Lys Arg
            100                 105

<210> SEQ ID NO 12
<211> LENGTH: 11
<212> TYPE: PRT
<213> ORGANISM: Artificial sequence
<220> FEATURE:
<223> OTHER INFORMATION: Chemically synthesized

<400> SEQUENCE: 12

Arg Ala Ser Glu Asn Phe Tyr Ser Tyr Leu Ala
1               5                   10

<210> SEQ ID NO 13
<211> LENGTH: 7
<212> TYPE: PRT
<213> ORGANISM: Artificial sequence
<220> FEATURE:
<223> OTHER INFORMATION: Chemically synthesized

<400> SEQUENCE: 13

Asn Ala Lys Thr Leu Ala Glu
1               5

<210> SEQ ID NO 14
<211> LENGTH: 9
<212> TYPE: PRT
<213> ORGANISM: Artificial sequence
<220> FEATURE:
<223> OTHER INFORMATION: Chemically synthesized

<400> SEQUENCE: 14
```

Gln His His Tyr Asp Ile Pro Leu Thr
1               5

<210> SEQ ID NO 15
<211> LENGTH: 354
<212> TYPE: DNA
<213> ORGANISM: Artificial sequence
<220> FEATURE:
<223> OTHER INFORMATION: Chemically synthesized

<400> SEQUENCE: 15
aagatccagt tggtgcagtc tggacctgaa ctgaagaagc ctggagagac agtcaagatc      60
tcctgcaagg cttctgggta cattcaca aactatggaa tgaactgggt gaagcaggct      120
ccaggaaagg gtttaaagtg gatgggctgg ataaacatca acactggaga gccaacatat    180
gctgaagagt tcaagggacg gtttgccttc tctttggaaa cctctgccac cactgccttt    240
ttgcagatca acaacctcaa aaatgaggac acggctacat atctctgtgc aagagattcc    300
tattcggggg gctttgacta ctggggccaa ggcaccattg tcacagtctc ctca          354

<210> SEQ ID NO 16
<211> LENGTH: 342
<212> TYPE: DNA
<213> ORGANISM: Artificial sequence
<220> FEATURE:
<223> OTHER INFORMATION: Chemically synthesized

<400> SEQUENCE: 16
gacattgtga tgacacagtc tccatcctcc ctgagtgtgt cagcaggaga gaaggtcact     60
ttgagctgca gtccagtca gagtctgtta atcagtggag atcaaaagaa ctacttggcc    120
tggtaccagc agaaaccagg gcagcctcct aaactgttga tctacggggc atccactagg    180
gactctgggg tccctgatcg cttcacaggc agtggatctg gagccgattt cactcttacc    240
atcagcagtg tgcaggctga agacctggca gtttattact gtcagaatga tcatagtttt    300
cctcccacgt tcggtgctgg gaccaagctg gagctgaaac gg                       342

<210> SEQ ID NO 17
<211> LENGTH: 118
<212> TYPE: PRT
<213> ORGANISM: Artificial sequence
<220> FEATURE:
<223> OTHER INFORMATION: Chemically synthesized

<400> SEQUENCE: 17

Lys Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Asn Tyr
            20                  25                  30
Gly Met Asn Trp Val Lys Gln Ala Pro Gly Lys Gly Leu Lys Trp Met
        35                  40                  45
Gly Trp Ile Asn Ile Asn Thr Gly Glu Pro Thr Tyr Ala Glu Glu Phe
    50                  55                  60
Lys Gly Arg Phe Ala Phe Ser Leu Glu Thr Ser Ala Thr Thr Ala Phe
65                  70                  75                  80
Leu Gln Ile Asn Asn Leu Lys Asn Glu Asp Thr Ala Thr Tyr Leu Cys
                85                  90                  95
Ala Arg Asp Ser Tyr Ser Gly Gly Phe Asp Tyr Trp Gly Gln Gly Thr
            100                 105                 110
Ile Val Thr Val Ser Ser

```
<210> SEQ ID NO 18
<211> LENGTH: 10
<212> TYPE: PRT
<213> ORGANISM: Artificial sequence
<220> FEATURE:
<223> OTHER INFORMATION: Chemically synthesized

<400> SEQUENCE: 18

Gly Tyr Thr Phe Thr Asn Tyr Gly Met Asn
1               5                   10

<210> SEQ ID NO 19
<211> LENGTH: 9
<212> TYPE: PRT
<213> ORGANISM: Artificial sequence
<220> FEATURE:
<223> OTHER INFORMATION: Chemically synthesized

<400> SEQUENCE: 19

Ile Asn Ile Asn Thr Gly Glu Pro Thr
1               5

<210> SEQ ID NO 20
<211> LENGTH: 9
<212> TYPE: PRT
<213> ORGANISM: Artificial sequence
<220> FEATURE:
<223> OTHER INFORMATION: Chemically synthesized

<400> SEQUENCE: 20

Asp Ser Tyr Ser Gly Gly Phe Asp Tyr
1               5

<210> SEQ ID NO 21
<211> LENGTH: 114
<212> TYPE: PRT
<213> ORGANISM: Artificial sequence
<220> FEATURE:
<223> OTHER INFORMATION: Chemically synthesized

<400> SEQUENCE: 21

Asp Ile Val Met Thr Gln Ser Pro Ser Ser Leu Ser Val Ser Ala Gly
1               5                   10                  15

Glu Lys Val Thr Leu Ser Cys Lys Ser Ser Gln Ser Leu Leu Ile Ser
            20                  25                  30

Gly Asp Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Asp Ser Gly Val
    50                  55                  60

Pro Asp Arg Phe Thr Gly Ser Gly Ser Gly Ala Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Phe Pro Pro Thr Phe Gly Ala Gly Thr Lys Leu Glu Leu
            100                 105                 110

Lys Arg

<210> SEQ ID NO 22
<211> LENGTH: 17
<212> TYPE: PRT
<213> ORGANISM: Artificial sequence
```

<220> FEATURE:
<223> OTHER INFORMATION: Chemically synthesized

<400> SEQUENCE: 22

Lys Ser Gln Ser Leu Leu Ile Ser Gly Asp Gln Lys Asn Tyr Leu
1               5                   10                  15
Ala

<210> SEQ ID NO 23
<211> LENGTH: 7
<212> TYPE: PRT
<213> ORGANISM: Artificial sequence
<220> FEATURE:
<223> OTHER INFORMATION: Chemically synthesized

<400> SEQUENCE: 23

Gly Ala Ser Thr Arg Asp Ser
1               5

<210> SEQ ID NO 24
<211> LENGTH: 9
<212> TYPE: PRT
<213> ORGANISM: Artificial sequence
<220> FEATURE:
<223> OTHER INFORMATION: Chemically synthesized

<400> SEQUENCE: 24

Gln Asn Asp His Ser Phe Pro Pro Thr
1               5

<210> SEQ ID NO 25
<211> LENGTH: 33
<212> TYPE: DNA
<213> ORGANISM: Homo sapiens

<400> SEQUENCE: 25
cagccggcca tggcccagga ctccacctca gac                                33

<210> SEQ ID NO 26
<211> LENGTH: 36
<212> TYPE: DNA
<213> ORGANISM: Artificial sequence
<220> FEATURE:
<223> OTHER INFORMATION: Chemically synthesized

<400> SEQUENCE: 26
ctctagactc gaggccgtcg atacactggt cgattg                             36

<210> SEQ ID NO 27
<211> LENGTH: 20
<212> TYPE: DNA
<213> ORGANISM: Artificial sequence
<220> FEATURE:
<223> OTHER INFORMATION: Chemically synthesized

<400> SEQUENCE: 27
tagcatgact ggtggacagc                                               20

<210> SEQ ID NO 28
<211> LENGTH: 18
<212> TYPE: DNA
<213> ORGANISM: Artificial sequence
<220> FEATURE:
<223> OTHER INFORMATION: Chemically synthesized

<400> SEQUENCE: 28

```
cgtagaatcg agaccgag                                                       18
```

<210> SEQ ID NO 29
<211> LENGTH: 558
<212> TYPE: DNA
<213> ORGANISM: Artificial sequence
<220> FEATURE:
<223> OTHER INFORMATION: Chemically synthesized

<400> SEQUENCE: 29

```
atgcaggact ctacttccga cctgattccg gctccgccgc tgtctaaagt gccgctgcag    60
cagaactttc aagacaacca gttccagggt aaatggtacg ttgtgggcct ggctggtaac   120
gcgatcctgc gtgaagacaa agatccgcag aaaatgtatg ctaccatcta cgaactgaaa   180
gaagacaaat cttataacgt gaccagcgtt ctgtttcgta aaagaaatg tgactactgg    240
attcgcacct tcgtgccggg ctctcagccg ggcgagttca ctctgggtaa catcaaatct   300
tacccgggtc tgactagcta cctggtgcgt gtggtttcta ctaactataa ccagcatgct   360
atggtgttct tcaagaaagt ttctcagaac cgtgaatact tcaagattac tctgtacggt   420
cgtaccaaag agctgacctc tgagctgaaa gaaaacttca ccgtttctc taaatctctg    480
ggcctgccgg agaaccatat cgtgtttccg gttccgatcg atcagtgcat cgacggtcat   540
catcaccatc accattga                                                  558
```

<210> SEQ ID NO 30
<211> LENGTH: 178
<212> TYPE: PRT
<213> ORGANISM: Artificial sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Gln can be preceded by a Met residue (e.g., when synthetic and/or produced in prokaryotes)
<220> FEATURE:
<221> NAME/KEY: MISC_FEATURE
<222> LOCATION: (178)..(178)
<223> OTHER INFORMATION: Can, optionally, be succeeded at the C-terminus by one or more His residues, and especially, 6 His residues (HHHHHH).

<400> SEQUENCE: 30

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
```

```
                    130                 135                 140
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 31
<211> LENGTH: 15
<212> TYPE: PRT
<213> ORGANISM: Artificial Sequence
<220> FEATURE:
<223> OTHER INFORMATION: scFV linking sequence

<400> SEQUENCE: 31

```
Gly Pro Ala Lys Glu Leu Thr Pro Leu Lys Glu Ala Lys Val Ser
1               5                   10                  15
```

<210> SEQ ID NO 32
<211> LENGTH: 552
<212> TYPE: DNA
<213> ORGANISM: Artificial sequence
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Optionally, can be preceded at the N-terminus
      by an initiation codon encoding Met, namely, an ATG.

<400> SEQUENCE: 32

```
caggactcca cctcagacct gatcccagcc ccacctctga gcaaggtccc tctgcagcag    60
aacttccagg acaaccaatt ccaggggaag tggtatgtgg taggcctggc agggaatgca   120
attctcagag aagacaaaga cccgcaaaag atgtatgcca ccatctatga gctgaaagaa   180
gacaagagct acaatgtcac ctccgtcctg tttaggaaaa agaagtgtga ctactggatc   240
aggacttttg ttccaggttc gcagcccggc gagttcacgc tgggcaacat taagagttac   300
cctggattaa cgagttacct cgtccgagtg gtgagcacca actacaacca gcatgctatg   360
gtgttcttca agaaagtttc tcaaaacagg gagtacttca agatcaccct ctacgggaga   420
accaaggagc tgacttcgga actaaaggag aacttcatcc gcttctccaa atctctgggc   480
ctccctgaaa accacatcgt cttccctgtc ccaatcgacc agtgtatcga cggccatcat   540
caccatcacc at                                                       552
```

<210> SEQ ID NO 33
<211> LENGTH: 178
<212> TYPE: PRT
<213> ORGANISM: Artificial sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Gln can be preceded by a Met residue (e.g.,
      when synthetic and/or produced in prokaryotes.
<220> FEATURE:
<221> NAME/KEY: MISC_FEATURE
<222> LOCATION: (178)..(178)
<223> OTHER INFORMATION: Can, optionally, be succeeded at the C-terminus
      by one or more His residues, and especially, 6 His residues
      (HHHHHH).

<400> SEQUENCE: 33

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
         50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

ANTIBODIES THAT BIND TO MAMMALIAN NGAL AND USES THEREOF

RELATED APPLICATION INFORMATION

This application is a Continuation of International Application No. PCT/US08/80340, filed Oct. 17, 2008, which is a Continuation-in-Part of U.S. Nonprovisional application Ser. No. 12/104,408, filed Apr. 16, 2008; Ser. No. 12/104,410, filed Apr. 16, 2008; and Ser. No. 12/104,413, filed Apr. 16, 2008; and International Application No. PCT/US08/80340 also claims benefit under 35 U.S.C. §119 to Provisional Application Nos. 60/981,470, filed Oct. 19, 2007; 60/981,471, filed Oct. 19, 2007; and 60/981,473, filed Oct. 19, 2007; all of which are incorporated by reference in their entireties.

TECHNICAL FIELD

The present invention relates to antibodies that bind to mammalian NGAL, and methods of using the antibodies.

BACKGROUND

Lipocalins are a family of extracellular ligand-binding proteins that are found in a variety of organisms from bacteria to humans. Lipocalins possess many different functions, such as the binding and transport of small hydrophobic molecules, nutrient transport, cell growth regulation, and modulation of the immune response, inflammation and prostaglandin synthesis. Moreover, some lipocalins are also involved in cell regulatory processes and serve as diagnostic and prognostic markers in a variety of disease states. For example, the plasma level of alpha glycoprotein is monitored during pregnancy and in diagnosis and prognosis of conditions including cancer chemotherapy, renal dysfunction, myocardial infarction, arthritis, and multiple sclerosis.

The novel lipocalin neutrophil gelatinase-associated lipocalin (or NGAL, also known as Lipocalin-2 or LCN2) from human neutrophils was identified in 1993. NGAL is a 25-kDa lipocalin that exists in monomeric and homo- and heterodimeric forms, the latter as a 46-kDa dimer with human neutrophil gelatinase. A trimer form of NGAL has also been identified. NGAL is secreted from specific granules of activated human neutrophils. Homologous proteins have been identified in mouse (24p3/uterocalin) and rat (alpha (2)-microglobulin-related protein/neu-related lipocalin). Structural data have confirmed a typical lipocalin fold of NGAL with an eight-stranded beta-barrel, but with an unusually large cavity lined with more polar and positively charged amino acid residues than normally seen in lipocalins. The 25-kDa NGAL protein is believed to bind small lipophilic substances such as bacteria-derived lipopolysaccharides and formylpeptides, and may function as a modulator of inflammation.

Renal injuries or disease, such as acute kidney failure or chronic kidney failure, can result from a variety of different causes (such as illness, injury, and the like). The early identification and treatment of renal injuries and disease would be useful in preventing disease progression. Currently, serum creatinine is frequently used as a biomarker of kidney function. However, serum creatinine measurements are influenced by muscle mass, gender, race and medications. Unfortunately, these limitations often result in the diagnosis of kidney disease only after significant damage has already occurred.

NGAL is an early marker for acute renal injury or disease. In addition to being produced by specific granules of activated human neutrophils, NGAL is also produced by nephrons in response to tubular epithelial damage and is a marker of tubulointerstitial (TI) injury. NGAL levels rise in acute tubular necrosis (ATN) from ischemia or nephrotoxicity, even after mild "subclinical" renal ischemia, as compared to normal serum creatinine levels. Moreover, NGAL is known to be expressed by the kidney in cases of chronic kidney disease (CKD). Elevated urinary NGAL levels have been suggested as predictive of progressive kidney failure. It has been previously demonstrated that NGAL is markedly expressed by kidney tubules very early after ischemic or nephrotoxic injury in both animal and human models. NGAL is rapidly secreted into the urine, where it can be easily detected and measured, and precedes the appearance of any other known urinary or serum markers of ischemic injury. The protein is resistant to proteases, suggesting that it can be recovered in the urine as a faithful marker of tubule expression of NGAL. Further, NGAL derived from outside of the kidney, for example, filtered from the blood, does not appear in the urine, but rather is quantitatively taken up by the proximal tubule.

A variety of immunoassays are known in the art for detecting NGAL. As mentioned previously herein, NGAL is found as a monomer, as a dimer (a homodimer or heterodimer) and even as a trimer. Thus, there is a need in the art for new antibodies and immunoassays which are able to specifically detect and distinguish between NGAL monomer, dimer or trimer in a test sample. Additionally, there is also a need in the art for immunoassays that are able to quantify the relative proportion of monomer to dimer contained in a test sample. Such new antibodies and immunoassays can be used to assess among other things the extent of any renal injury or disease in a patient, monitor the kidney status of a patient suffering from renal injury or disease, or assess the extent of any renal injury in a patient and thereafter monitor the patient's kidney status. Additional objects and advantages of the invention will be apparent from the description provided herein.

SUMMARY

In one embodiment, the present invention relates to an isolated antibody that specifically binds to a conformational epitope comprising amino acid residues 112, 118 and 147 of human NGAL protein as set forth in SEQ ID NOS:1 or 33. The isolated antibody can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

The above described antibody further binds to at least one additional amino acid of human NGAL protein, wherein the amino acid is selected from the group consisting of amino acid residues 117 or 119 of human NGAL protein as set forth in SEQ ID NOS:1 or 33. More specifically, the antibody further binds to amino acid residue 117 of human NGAL protein as set forth in SEQ ID NOS:1 or 33. Alternatively, the antibody further binds to amino acid residue 119 of human NGAL protein as set forth in SEQ ID NOS:1 or 33. Alternatively, the antibody further binds to amino acid residues 117 and 119 of human NGAL protein as set forth in SEQ ID NOS:1 or 33.

In another embodiment, the present invention relates to an isolated antibody that specifically binds to human NGAL, wherein the antibody has a variable heavy domain region comprising the amino acid sequence of SEQ ID NO:7.

In another embodiment, the present invention relates to an isolated antibody that specifically bind to human NGAL, wherein the antibody has a variable light domain region comprising the amino acid sequence of SEQ ID NO:11.

In still yet another embodiment, the present invention relates to an isolated antibody that specifically binds to human NGAL, wherein the antibody has a variable heavy domain region comprising the amino acid sequence of SEQ ID NO:7 and a variable light domain region comprising the amino acid sequence of SEQ ID NO:11.

In yet another embodiment, the present invention relates to a murine hybridoma cell line 1-2322-455 having ATCC Accession No. PTA-8024.

In yet still another embodiment, the present invention relates to an antibody produced by murine hybridoma cell line 1-2322-455 having ATCC Accession No. PTA-8024.

In still yet another embodiment, the present invention relates to an isolated antibody that specifically binds to human NGAL, wherein the antibody has a variable heavy domain region comprising the amino acid sequence of SEQ ID NO:17.

In yet another embodiment, the present invention relates to an isolated antibody that specifically bind to human NGAL, wherein the antibody has a variable light domain region comprising the amino acid sequence of SEQ ID NO:21.

In another embodiment, the present invention relates to an isolated antibody that specifically binds to human NGAL, wherein the antibody has a variable heavy domain region comprising the amino acid sequence of SEQ ID NO:17 and a variable light domain region comprising the amino acid sequence of SEQ ID NO:21.

In another embodiment, the present invention relates to a murine hybridoma cell line 1-903-430 having ATCC Accession No. PTA-8026.

In still another embodiment, the present invention relates to an antibody produced by murine hybridoma cell line 1-903-430 having ATCC Accession No. PTA-8026.

In still yet another embodiment, the present invention relates to an immunodiagnostic reagent comprising one or more antibodies selected from the group consisting of:

(a) an antibody that specifically binds to a conformational epitope comprising amino acid residues 112, 118 and 147 of human NGAL protein as set forth in SEQ ID NOS:1, 2, 30 or 33;

(b) an isolated antibody that specifically binds to human NGAL, wherein the antibody has a variable heavy domain region comprising the amino acid sequence of SEQ ID NO:7;

(c) an isolated antibody that specifically bind to human NGAL, wherein the antibody has a variable light domain region comprising the amino acid sequence of SEQ ID NO:11;

(d) an isolated antibody that specifically binds to human NGAL, wherein the antibody has a variable heavy domain region comprising the amino acid sequence of SEQ ID NO:7 and a variable light domain region comprising the amino acid sequence of SEQ ID NO:11;

(e) an antibody produced by murine hybridoma cell line 1-2322-455 having ATCC Accession No. PTA-8024;

(f) an isolated antibody that specifically binds to human NGAL, wherein the antibody has a variable heavy domain region comprising the amino acid sequence of SEQ ID NO:17;

(g) an isolated antibody that specifically bind to human NGAL, wherein the antibody has a variable light domain region comprising the amino acid sequence of SEQ ID NO:21;

(h) an isolated antibody that specifically binds to human NGAL, wherein the antibody has a variable heavy domain region comprising the amino acid sequence of SEQ ID NO:17 and a variable light domain region comprising the amino acid sequence of SEQ ID NO:21; and (i) an antibody produced by murine hybridoma cell line 1-903-430 having ATCC Accession No. PTA-8026.

In still yet another embodiment, the present invention relates to an isolated antibody that specifically binds to a human NGAL protein as set forth in SEQ ID NOS:1, 2, 30 or 33 (especially as set forth in SEQ ID NOS: 30 or 33), wherein as a result of adding the antibody to the human NGAL protein, the antibody causes as compared to when the antibody is not added, (1) a perturbation of from about 0.05 ppm to about 1.0 ppm in a $^1$H resonance position, (2) a perturbation of from about 0.3 ppm to about 3.0 ppm in a $^{15}$N resonance position, or (3) from about a 2.5-fold to about a 20-fold decrease in resonance intensity, in a TROSY proton-nitrogen correlation NMR spectra of at least four of the amide resonance positions for amino acids corresponding to residues of SEQ ID NOS:1, 2, 30 or 33 (especially of SEQ ID NOS: 30 or 33) selected from the group consisting of:

(a) for residue N116, a resonance position located at about $^1$H=9.47 or about $^{15}$N=118.30;

(b) for residue Q117, a resonance position located at about $^1$H=7.79 or about $^{15}$N=117.67;

(c) for residue H118, a resonance position located at about $^1$H=8.75 or about $^{15}$N=116.43;

(d) for residue T141, a resonance position located at about $^1$H=7.99 or about $^{15}$N=109.06;

(e) for residue K142, a resonance position located at about $^1$H=7.82 or about $^{15}$N=114.25;

(f) for residue E143, a resonance position located at about $^1$H=7.40 or about $^{15}$N=114.00; and (g) for residue E150, a resonance position located at about $^1$H=8.70 or about $^{15}$N=118.80.

In still yet another embodiment, the present invention relates to an isolated antibody that specifically binds to a human NGAL protein as set forth in SEQ ID NOS:1, 2, 30 or 33 (especially as set forth in SEQ ID NOS: 30 or 33), wherein as a result of adding the antibody to the human NGAL protein, the antibody causes as compared to when the antibody is not added, (1) a perturbation of from about 0.05 ppm to about 1.0 ppm in a $^1$H resonance position, (2) a perturbation of from about 0.3 ppm to about 3.0 ppm in a $^{15}$N resonance position, or (3) from about a 2.5-fold to about a 20-fold decrease in resonance intensity, in a TROSY proton-nitrogen correlation NMR spectra of at least four of the amide resonance positions for amino acids corresponding to residues SEQ ID NOS:1, 2, 30 or 33 (especially of SEQ ID NOS: 30 or 33) selected from the group consisting of:

(a) for residue Y64, a resonance position located at about $^1$H=9.15 or about $^{15}$N=113.30;

(b) for residue V84, a resonance position located at about $^1$H=9.34 or about $^{15}$N=121.50;

(c) for residue G87, a resonance position located at about $^1$H=8.32 or about $^{15}$N=111.60;

(d) for residue T93, a resonance position located at about $^1$H=9.32 or about $^{15}$N=112.20;

(e) for residue L94, a resonance position located at about $^1$H=7.71 or about $^{15}$N=122.34;

(f) for residue G95, a resonance position located at about $^1H=9.35$ or about $^{15}N=114.13$; and (g) for residue S99, a resonance position located at about $^1H=8.18$ or about $^{15}N=114.40$.

BRIEF DESCRIPTION OF THE FIGURES

FIG. 1 shows the human NGAL wild-type antigen sequence (SEQ ID NO:1). Native human NGAL signal peptide residues are in italics and underlined. Wild-type human NGAL sequences in pJV-NGAL-A3 plasmid are in bold. The 6×His tag in the C-terminal is underlined.

FIG. 3 shows the human NGAL C87S mutant antigen sequences (SEQ ID NO:2). Native human NGAL signal peptides are in italics and underlined. Wild-type NGAL sequences in the pJV-NGAL(Ser87)-His-T3 plasmid are in bold, and the NGAL C87S mutant codon sequence is in bold and underlined. The 6×His tag in the C-terminal is also underlined.

FIG. 4 shows the wild-type human NGAL polynucleotide sequence (SEQ ID NO:3).

FIG. 5 shows the mutant human NGAL polynucleotide sequence (SEQ ID NO:4).

FIGS. 9A-B show various sequences of monoclonal antibody 1-2322-455. FIG. 9A shows the polynucleotide and amino acid sequences of the variable heavy chain (SEQ ID NOS:5 and 7), and the amino acid sequence for the CDR heavy chain 1 (SEQ ID NO:8), CDR heavy chain 2 (SEQ ID NO:9), and CDR heavy chain 3 (SEQ ID NO:10). FIG. 9B shows polynucleotide and amino acid sequences of the variable variable light chain (SEQ ID NO:6 and 11), and the amino acid sequence for the CDR light chain 1 (SEQ ID NO:12), CDR light chain 2 (SEQ ID NO:13) and CDR light chain 3 (SEQ ID NO:14).

FIGS. 10A-B show various sequences of monoclonal antibody 1-903-430. FIG. 10A shows the polynucleotide and amino acid sequences for the variable heavy chain (SEQ ID NOS:15 and 17) and the amino acid sequence for the CDR heavy chain 1 (SEQ ID NO:18), CDR heavy chain 2 (SEQ ID NO:19), and CDR heavy chain 3 (SEQ ID NO:20). FIG. 10B shows the polynucleotide and amino acid sequences for the variable light chain (SEQ ID NOS:16 and 21) and the amino acid sequence for the CDR light chain 1 (SEQ ID NO:22), CDR light chain 2 (SEQ ID NO:23) and CDR light chain 3 (SEQ ID NO:24).

FIG. 13A shows the critical residues (Arg109 and Lys15) for the anti-NGAL monoclonal antibody 1-903-430 interaction. FIG. 13B shows the critical residues (Ser112, His118 and Glu147) for the anti-NGAL 1-2322-455 monoclonal antibody interaction.

FIG. 14 shows the polynucleotide sequence (SEQ ID NO:29) and amino acid sequence (SEQ ID NO:30) of mutagenized NGAL (mature NGAL sequence minus any signal peptide) used in Example 8 to identify epitopes of NGAL using NMR. The bold sequences at amino acid residue 87 and nucleotide 263 illustrate the changed nucleotide in the modified codon and the predicted Cys to Ser alteration. The italicized Cys at residues 76 and 175 illustrates an intra-chain S—S bond (there being three Cys residues in wild-type NGAL at residues 76, 87 and 175). The initial Met residue is produced only in prokaryotes and not eukaryotes, and consequently, is counted herein as residue −1 when present, and with no similar adjustment made for polynucleotide sequence when present in prokaryotes versus eukaryotes. The TGA terminator codon is identified on the amino acid sequence with an asterisk.

FIG. 17A shows a section of spectra after addition of an excess of mAb 903. FIG. 17B shows the corresponding portion of spectra of human NGAL after addition of an excess of mAb 2322. The difference between these figures confirms that the antibodies interact on different surfaces on NGAL. Assignments are based on those deposited in the public database *Biological Magnetic Resonance Data Bank* (database entry 4267).

FIG. 18A shows the resonance changes observed for mAb 2322. FIG. 18B shows the resonance changes observed for mAb 809. FIG. 18C shows the resonance changes observed for mAb 269. FIG. 18D shows the resonance changes observed for mAb 181. FIG. 18E shows the resonance changes observed for mAb 903. FIG. 18F shows the resonance changes observed for mAb 419.

FIG. 19A shows the location of some of the residues perturbed by mAb 2322 binding, including residues between K142 and E150. FIG. 19B shows the surface location of some of the residues perturbed by mAb 903 binding including L18 and Q88. Both ribbons are in the same orientation.

FIG. 21A shows results for the mAb 2322 and mAb 903 pair. FIG. 21B shows results for the mAb 2322 and mAb 809 pair. FIG. 21C shows results for the mAb 809 and mAb 181 pair.

DETAILED DESCRIPTION

Figure 2:
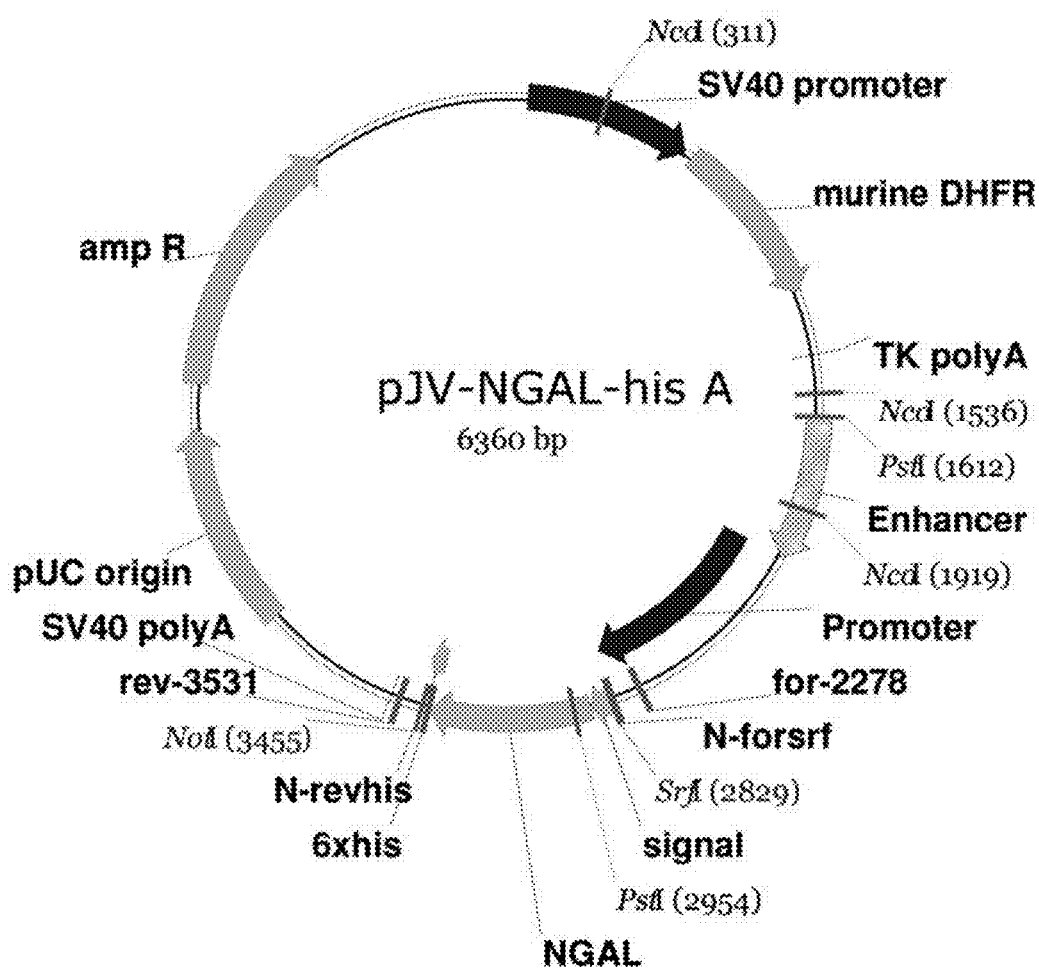
FIG. 2 shows plasmid pJV-NGAL-A3 (also known as pJV-NGAL-hisA) containing the wild-type human NGAL sequence as discussed in Example 1.

Antibodies that bind to certain mammalian NGAL proteins have been discovered. These anti-NGAL antibodies (also loosely referred to herein as "NGAL antibodies") either alone or in combination have a variety of uses, for example, as a component of a diagnostic assay, or present in an immunoassay kit.

All NGAL polynucleotide and polypeptide sequences, and wild-type NGAL recombinant antigen (rAg) and mutant C87S NGAL NGAL rAg clones, subclones, hybrids, and hybridomas (including names and numbering) are as described in U.S. Provisional Application Ser. No. 60/981,470 filed Oct. 19, 2007 (incorporated by reference for its teachings regarding same).

A. DEFINITIONS

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Antibody

As used herein, the terms "antibody" and "antibodies" refer to monoclonal antibodies, multispecific antibodies, human antibodies, humanized antibodies (fully or partially humanized), animal antibodies (in one aspect, a bird (for example, a duck or goose), in another aspect, a shark or whale, in yet another aspect, a mammal, including a non-primate (for example, a cow, pig, camel, llama, horse, goat, rabbit, sheep, hamsters, guinea pig, feline, canine, rat, murine, etc) and a non-human primate (for example, a monkey, such as a cynomologous monkey, a chimpanzee, etc), recombinant antibodies, chimeric antibodies, single-chain Fvs (scFv), single chain antibodies, single domain antibodies, Fab fragments, F(ab')$_2$ fragments, disulfide-linked Fv (sdFv), and anti-idiotypic (anti-Id) antibodies (including, for example, anti-Id antibodies to antibodies of the present invention), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_1$ and IgA$_2$) or subclass. For simplicity sake, an antibody against an analyte is frequently referred to as being either an "anti-analyte antibody", or merely an "analyte antibody" (e.g., an NGAL antibody).

b) Renal Tubular Cell Injury

As used herein the expression "renal tubular cell injury" means a renal or kidney failure or dysfunction, either sudden (acute) or slowly declining over time (chronic), that can be triggered by a number of disease or disorder processes. Both acute and chronic forms of renal tubular cell injury can result in a life-threatening metabolic derangement.

c) Acute Kidney Disease

An "acute renal tubular cell injury" means acute ischemic renal injury (IRI) or acute nephrotoxic renal injury (NRI). IRI includes but is not limited to ischemic injury and chronic ischemic injury, acute renal failure, acute glomerulonephritis, and acute tubulo-interstitial nephropathy. NRI toxicity includes but is not limited to, sepsis (infection), shock, trauma, kidney stones, kidney infection, drug toxicity, poisons or toxins, or after injection with a radiocontrast dye.

d) Chronic Kidney Disease

The phrases "chronic renal tubular cell injury", "progressive renal disease", "chronic renal disease (CRD)", "chronic kidney disease (CKD)" as used interchangeably herein, include any kidney condition or dysfunction that occurs over a period of time, as opposed to a sudden event, to cause a gradual decrease of renal tubular cell function or worsening of renal tubular cell injury. One endpoint on the continuum of chronic renal disease is "chronic renal failure (CRF)". For example, chronic kidney disease or chronic renal injury as used interchangeably herein, includes, but is not limited to, conditions or dysfunctions caused by chronic infections, chronic inflammation, glomerulonephritides, vascular diseases, interstitial nephritis, drugs, toxins, trauma, renal stones, long standing hypertension, diabetes, congestive heart failure, nephropathy from sickle cell anemia and other blood dyscrasias, nephropathy related to hepatitis, HIV, parvovirus and BK virus (a human polyomavirus), cystic kidney diseases, congenital malformations, obstruction, malignancy, kidney disease of indeterminate causes, lupus nephritis, membranous glomerulonephritis, membranoproliferative glomerulonephritis, focal glomerular sclerosis, minimal change disease, cryoglobulinemia, Anti-Neutrophil Cytoplasmic Antibody (ANCA)-positive vasculitis, ANCA-negative vasculitis, amyloidosis, multiple myeloma, light chain deposition disease, complications of kidney transplant, chronic rejection of a kidney transplant, chronic allograft nephropathy, and the chronic effects of immunosuppressives. Preferably, chronic renal disease or chronic renal injury refers to chronic renal failure or chronic glomerulonephritis.

e) Immunodiagnostic Reagent

An "immunodiagnostic reagent" according to the present invention comprises one or more antibodies that specifically bind to a region of an NGAL protein. The use of such antibodies of the present invention, e.g., in immunoassays and/or as calibrators, controls, and immunodiagnostic agents, is described herein. However, the antibodies of the subject invention also optionally can be employed in improved NGAL assays, e.g., as set forth in U.S. Provisional Application Ser. No. 60/981,473 filed Oct. 19, 2007 (incorporated by reference for its teachings regarding same).

f) NGAL Polynucleotide and Polypeptide Sequences

NGAL polynucleotide and polypeptide sequences are as described in U.S. Provisional Application Ser. No. 60/981, 470 filed Oct. 19, 2007 (incorporated by reference for its teachings regarding same). Such polynucleotide and polypeptide sequences optionally can be employed in the context of the subject invention.

Generally, the NGAL as employed herein can be any NGAL sequence, e.g., including that set forth as Genbank accession numbers Genpept CAA58127 (SEQ ID NO:1), AAB26529, XP_862322, XP_548441, P80108, P11672, X83006.1, X99133.1, CAA67574.1, BC033089.1, AAH33089.1, S75256.1, AD14168.1, JC2339, 1DFVA, 1DFVB, 1L6MA, 1L6MB, 1L6MC, 1NGLA, 1QQSA, 1X71A, 1X71B, 1X71C, 1X89A, 1X89B, 1X89C, 1X8UA, 1X8UB, and 1X8UC. NGAL polynucleotide and polypeptide (e.g., polyamino acid) sequences are as found in nature, based on sequences found in nature, isolated, synthetic, semi-synthetic, recombinant, or other. In one embodiment, the NGAL is human NGAL (also known as "hNGAL"). Unless specified otherwise, NGAL polypeptide sequences are numbered according to the mature human NGAL sequence minus the 20 residue amino acid signal peptide typically found in nature (and minus any other signal peptide sequence). When a signal peptide is present, it is numbered with negative numbers, e.g., as residues −1 to −20, with comparable numbering applied for the encoding polynucleotide sequence.

Likewise, an initial Met residue at the N-terminus of NGAL is present only in NGAL produced in prokaryotes (e.g., *E. coli*), or in synthetic (including semi-synthetic) or derived sequences, and not in NGAL produced in eukaryotes (e.g., mammalian cells, including human and yeast cells). Consequently, when present, an initial Met residue is counted herein as a negative number, e.g., as residue −1, with no similar numbering adjustment being made for the polynucleotide sequence in a prokaryotic versus eukaryotic background or expression system inasmuch as the polynucleotide sequence is replicated and transcribed the same in both backgrounds and the difference lies at the level of translation.

Accordingly, the disclosure herein encompasses the use (e.g., as an immunogen and/or in antibody binding studies) of a multitude of different NGAL polynucleotide and polypeptide sequences as present and/or produced in a prokaryotic and/or eukaryotic background (e.g., with consequent optimization for codon recognition). In sum, the sequences may or may not possess or encode: (a) a signal peptide; (b) an initiator Met residue present in the mature NGAL sequence at the N-terminus; (c) an initiator Met residue present at the start of a signal peptide that precedes the mature NGAL protein; and (d) other variations such as would be apparent to one skilled in the art.

Exemplary sequences include, but are not limited to, those as set forth herein: SEQ ID NO:1 (NGAL wild-type polypeptide including signal peptide); SEQ ID NO:2 (NGAL mutant polypeptide including signal peptide); SEQ ID NO:30 (NGAL mutant polypeptide not including any signal peptide, and which can be preceded by a Met initiator residue when produced in prokaryotes and a Met initiator codon is present; however, there is no Met initiator residue when produced in eukaryotes, regardless of whether a Met initiator codon is present); SEQ ID NO:33 (NGAL wild-type polypeptide not including any signal peptide, and which can be preceded by a Met initiator residue when produced in prokaryotes and a Met initiator codon is present; however, there is no Met initiator residue when produced in eukaryotes, regardless of whether a Met initiator codon is present); SEQ ID NO:3 (NGAL wild-type polynucleotide sequence including that encoding a signal peptide); SEQ ID NO:4 (NGAL mutant polynucleotide including that encoding a signal peptide); SEQ ID NO:32 (NGAL mutant polynucleotide, synthetic or for eukaryotic expression, not including that encoding any signal peptide, but which optionally further can be preceded at the N-terminus either with or without a Met initiator codon, e.g., ATG); SEQ ID NO:29 (NGAL mutant polynucleotide, synthetic or for prokaryotic expression, not including that encoding any signal peptide, but which optionally further can be preceded at the N-terminus either with or without a Met initiator codon, e.g., ATG).

g) Glycosylated Mammalian NGAL

Glycosylated mammalian NGAL (e.g., employed as an immunogen and/or assessing the binding of various antibodies) is as described in U.S. Provisional Application Ser. No. 60/981,470 filed Oct. 19, 2007 (incorporated by reference for its teachings regarding same).

Generally, as used herein, the phrases "oligosaccharide moiety" or "oligosaccharide molecule" as used interchangeably herein refers to a carbohydrate-containing molecule comprising one or more monosaccharide residues, capable of being attached to a polypeptide (to produce a glycosylated polypeptide, such as, for example, mammalian NGAL) by way of in vivo or in vitro glycosylation. Except where the number of oligosaccharide moieties attached to the polypeptide is expressly indicated, every reference to "oligosaccharide moiety" referred to herein is intended as a reference to one or more such moieties attached to a polypeptide. Preferably, the polypeptide to which said carbohydrate-containing molecule is capable of being attached is wild-type or mutant mammalian NGAL, i.e., to provide "glycosylated mammalian NGAL" as described further herein.

The term "in vivo glycosylation" is intended to mean any attachment of an oligosaccharide moiety occurring in vivo, for example, during posttranslational processing in a glycosylating cell used for expression of the polypeptide, for example, by way of N-linked and O-linked glycosylation. Usually, the N-glycosylated oligosaccharide-moiety has a common basic core structure composed of five monosaccharide residues, namely two N-acetylglucosamine residues and three mannose residues. The exact oligosaccharide structure depends, to a large extent, on the glycosylating organism in question and on the specific polypeptide.

The phrase "in vitro glycosylation" refers to a synthetic glycosylation performed in vitro, normally involving covalently linking an oligosaccharide moiety to an attachment group of a polypeptide, optionally using a cross-linking agent. In vitro glycosylation can be achieved by attaching chemically synthesized oligosaccharide structures to a polypeptide (such as, for example, mammalian NGAL) using a variety of different chemistries. For example, the chemistries that can be employed are those used for the attachment of polyethylene glycol (PEG) to proteins, wherein the oligosaccharide is linked to a functional group, optionally, via a short spacer. In vitro glycosylation can be carried out in a suitable buffer at a pH of about 4.0 to about 7.0 in protein concentrations of about 0.5 to about 2.0 mg/mL in a volume of about 0.02 to about 2.0 ml. Other in vitro glycosylation methods are described, for example in WO 87/05330, by Aplin et al., *CRC Crit. Rev. Biochem.* 259-306 (1981), by Lundblad et al. in *Chemical Reagents for Protein Modification*, CRC Press Inc., Boca Raton, Fla., Yan et al., *Biochemistry*, 23:3759-3765 (1982) and Doebber et al., *J. Biol. Chem.*, 257:2193-2199 (1982).

h) Human NGAL Fragment

A human NGAL fragment (e.g., employed as an immunogen and/or for assessing the binding of various antibodies) is as described in U.S. Provisional Application Ser. No. 60/981,470 filed Oct. 19, 2007 (incorporated by reference for its teachings regarding same).

Generally, as used herein, the term "human NGAL fragment" herein refers to a polypeptide that comprises a part that is less than the entirety of a mature human NGAL or NGAL including a signal peptide. In particular, a human NGAL fragment comprises from about 5 to about 178 or about 179 contiguous amino acids of SEQ ID NOS:1, 2, 30 or 33. In particular, a human NGAL fragment comprises from about 5 to about 170 contiguous amino acids of SEQ ID NOS:1, 2, 30 or 33. In particular, a human NGAL fragment comprises at least about 5 contiguous amino acids of SEQ ID NO:1, 2, 30 or 33, at least about 10 contiguous amino acids residues of SEQ ID NOS:1, 2, 30 or 33; at least about 15 contiguous amino acids residues of amino acids of SEQ ID NOS:1, 2, 30 or 33; at least about 20 contiguous amino acids residues of SEQ ID NOS:1, 2, 30 or 33; at least about 25 contiguous amino acids residues of SEQ ID NOS:1, 2, 30 or 33, at least about 30 contiguous amino acid residues of amino acids of SEQ ID NOS:1, 2, 30 or 33, at least about 35 contiguous amino acid residues of SEQ ID NOS:1, 2, 30 or 33, at least about 40 contiguous amino acid residues of SEQ ID NOS:1, 2, 30 or 33, at least about 45 contiguous amino acid residues of SEQ ID NOS:1, 2, 30 or 33, at least about 50 contiguous amino acid residues of SEQ ID NOS:1, 2, 30 or 33, at least about 55 contiguous amino acid residues of SEQ ID NOS:1, 2, 30 or 33, at least about 60 contiguous amino acid residues of SEQ ID NOS:1, 2, 30 or 33, at least about 65 contiguous amino acid residues of SEQ ID NOS:1, 2, 30 or 33, at least about 70 contiguous amino acid residues of SEQ ID NOS:1, 2, 30 or 33, at least about 75 contiguous amino acid residues of SEQ ID NOS:1, 2, 30 or 33, at least about 80 contiguous amino acid residues of SEQ ID NOS:1, 2, 30 or 33, at least about 85 contiguous amino acid residues of SEQ ID NOS:1, 2, 30 or 33, at least about 90 contiguous amino acid residues of SEQ ID NOS:1, 2, 30 or 33, at least about 95 contiguous amino acid residues of SEQ ID NOS:1, 2, 30 or 33, at least about 100 contiguous amino acid residues of SEQ ID NOS:1, 2, 30 or 33, at least about 105 contiguous amino acid residues of SEQ ID NOS:1, 2, 30 or 33, at least about 110 contiguous amino acid residues of SEQ ID NOS:1, 2, 30 or 33, at least about 115 contiguous amino acid residues of SEQ ID NOS:1, 2, 30 or 33, at least about 120 contiguous amino acid residues of SEQ ID NOS:1, 2, 30 or 33, at least about 125 contiguous amino acid residues of SEQ ID NOS:1, 2, 30 or 33, at least about 130 contiguous amino acid residues of SEQ ID NOS:1, 2, 30 or 33, at least about 135 contiguous amino acid residues of SEQ ID NOS:1, 2, 30 or 33, at least about 140 contiguous amino acid residues of SEQ ID NOS:1, 2, 30 or 33, at least about 145 contiguous amino acid residues of SEQ ID NOS:1, 2, 30 or 33, at least about 150 contiguous amino acid residues of SEQ ID NOS:1, 2, 30 or 33, at least about 160 contiguous amino acid residues of SEQ ID NOS:1, 2, 30 or 33, at least about 165 contiguous amino acid residues of SEQ ID NOS:1, 2, 30 or 33, at least about 170 contiguous amino acid residues of SEQ ID NOS:1, 2, 30 or 33 or at least about 175 contiguous amino acid residues of SEQ ID NOS:1, 2, 30 or 33.

Examples of human NGAL fragments contemplated for use in the context of the present invention (e.g., employed as an immunogen and/or for assessing the binding of various antibodies) include, but are not limited to:

(a) a human NGAL fragment of at least about 7 contiguous amino acids which includes amino acid residues 112, 113, 114, 115, 116, 117 and 118 of SEQ ID NOS:1, 2, 30 or 33 (with the numbering of SEQ ID NO:1 and 2 beginning at the Gln residue of the mature sequence immediately following the signal peptide and any Met initiator residue, and the signal peptide and any Met initiator residue(s) being numbered in the negative, as previously described herein);

(b) a human NGAL fragment of at least about 8 contiguous amino acids which includes amino acid residues 112, 113, 114, 115, 116, 117, 118 and 119 of SEQ ID NOS:1, 2, 30 or 33 (with the numbering of SEQ ID NO:1 and 2 beginning at the Gln residue of the mature sequence immediately following the signal peptide and any Met initiator residue);

(c) a human NGAL fragment of at least about 36 contiguous amino acid which includes amino acid residues 112, 118 and 147 of SEQ ID NOS:1, 2, 30 or 33 (with the numbering of SEQ ID NO:1 and 2 beginning at the Gln residue of the mature sequence immediately following the signal peptide and any Met initiator residue);

(d) a human NGAL fragment of at least about 95 contiguous amino acids which includes amino acid residues 15 and 109 of SEQ ID NOS:1, 2, 30 or 33 (with the numbering of SEQ ID NO:1 and 2 beginning at the Gln residue of the mature sequence immediately following the signal peptide and any Met initiator residue);

(e) a human NGAL fragment of at least about 144 contiguous amino acids which includes amino acid residues 15, 109 and 158 of SEQ ID NOS:1, 2, 30 or 33 (with the numbering of SEQ ID NO:1 and 2 beginning at the Gln residue of the mature sequence immediately following the signal peptide and any Met initiator residue);

(f) a human NGAL fragment of at least about 145 contiguous amino acids which includes amino acid residues 15, 109, 158 and 159 of SEQ ID NOS:1, 2, 30 or 33 (with the numbering of SEQ ID NO:1 and 2 beginning at the Gln residue of the mature sequence immediately following the signal peptide and any Met initiator residue); or (g) a human NGAL fragment of at least about 146 contiguous amino acids which includes amino acid residues 15, 109, 158, 159 and 160 of SEQ ID NOS:1, 2, 30 or 33 (with the numbering of SEQ ID NO:1 and 2 beginning at the Gln residue of the mature sequence immediately following the signal peptide and any Met initiator residue).

Optionally, such human NGAL fragments employed as described herein are encoded either in part or in the entirety by the corresponding sequences of SEQ ID NOS:3, 4 or 32. Along these lines, in one embodiment, the present invention contemplates the use of an isolated, purified, or isolated and purified human NGAL polynucleotide comprising or consisting of the sequence of SEQ ID NOS:4 or 32.

i) NGAL Hybrid

As used herein, the term "NGAL hybrid" or 'NGAL hybridoma" refers to a particular hybridoma clone or subclone (as specified) that produces an anti-NGAL antibody of interest. Generally, there may be some small variation in the affinity of antibodies produced by a hybridoma clone as compared to those from a subclone of the same type, e.g., reflecting purity of the clone. By comparison, it is well established that all hybridoma subclones originating from the same clone and further, that produce the anti-NGAL antibody of interest produce antibodies of identical sequence and/or identical structure.

j) Specific Binding

The term "specific binding" is defined herein as the preferential binding of one binding partner to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a random molecule lacking the specifically recognized site(s)).

k) Binding Partner

A "binding partner," as used herein, is a member of a binding pair, i.e., a pair of molecules wherein one of the molecules binds to the second molecule. Binding partners that bind specifically are termed "specific binding partners." In addition to the antigen and antibody binding partners commonly used in immunoassays, other specific binding partners can include biotin and avidin, carbohydrates and lectins, complementary nucleotide sequences, effector and receptor molecules, cofactors and enzymes, enzyme inhibitors and enzymes, and the like. Furthermore, specific binding partners can include partner(s) that is/are analog(s) of the original specific binding partner, for example, an analyte-analog. Immunoreactive specific binding partners include antigens, antigen fragments, antibodies and antibody fragments, both monoclonal and polyclonal, and complexes thereof, including those formed by recombinant DNA methods.

l) Epitope

As used herein, the term "epitope", "epitopes" or "epitopes of interest" refer to a site(s) on any molecule that is recognized and is capable of binding to a complementary site(s) on its specific binding partner. The molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner, can be, but is not limited to, an antibody.

In particular, an epitope refers to a particular region (composed of one or more amino acids) of an antigen, namely a protein to which an antibody binds. More specifically, an antigenic epitope is the area on protein surface that interacts with the complementary area (paratope) on the surface of the antibody binding domains. The epitope thus participates in electrostatic interactions, hydrophobic interactions and hydrogen bonding with the antibody and also contains residues responsible for the correct geometry of the surface, its malleability and structural dynamics. There are also buried "second sphere" residues that carry a strong supporting role for the antigenic epitope.

m) Binding Constants (e.g., $K_D$, $k_a$, and $k_d$)

The terms "equilibrium dissociation constant" or "$K_D$", as used interchangeably herein, refer to the value obtained in a titration measurement at equilibrium, or by dividing the dissociation rate constant ($k_{off}$) by the association rate constant ($k_{on}$). The association rate constant, the dissociation rate constant and the equilibrium dissociation constant are used to represent the binding affinity of an antibody to an antigen.

The terms "relative affinity" or "relative $K_R$", can be defined as the binding avidity of antibody to antigen revealed using the same test method to measure antibody/antigen $K_D$ within a test population that includes antiserum test samples or uncloned hybrid test samples, thus providing relative affinity values rather than 'absolute' specificity data. (See, e.g., Immunology, 32:49 (1977) and Essential Immunology, Blackwell Scientific Publications, 7th edition, page 74 (1991)).

The term "association rate constant", "$k_{on}$" or "$k_a$" as used interchangeably herein, refers to the value indicating the binding rate of an antibody to its target antigen or the rate of complex formation between an antibody and antigen as shown by the equation below:

$$\text{Antibody (``Ab'')} + \text{Antigen (``Ag'')} \rightarrow \text{Ab-Ag.}$$

The term "dissociation rate constant", "$k_{off}$" or "$k_d$" as used interchangeably herein, refers to the value indicating the dissociation rate of an antibody from its target antigen or separation of Ab–Ag complex over time into free antibody and antigen as shown by the equation below:

$$\text{Ab} + \text{Ag} \leftarrow \text{Ab-Ag.}$$

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

n) Subject

As used herein, the terms "subject" and "patient" are used interchangeably irrespective of whether the subject has or is currently undergoing any form of treatment. As used herein, the terms "subject" and "subjects" refer to a mammal including, a non-primate (for example, a cow, pig, camel, llama, horse, goat, rabbit, sheep, hamsters, guinea pig, feline, canine, rat, and murine), a non-human primate (for example, a monkey, such as a cynomolgous monkey, chimpanzee, etc) and a human. Preferably, the subject is a human.

o) Test Sample

As used herein, the term "test sample" refers to a biological sample derived from serum, plasma, blood (including, but not limited to, whole blood), lymph, urine or other bodily fluids of a subject. The test sample can be prepared using routine techniques known to those skilled in the art. Preferably, the test sample is urine or blood.

p) Pretreatment Reagent (e.g., Lysis, Precipitation and/or Solubilization Reagent)

A pretreatment reagent used in a diagnostic assay as described herein is one that lyses any cells and/or solubilizes any analyte that are present in a test sample. Pretreatment is not necessary for all samples, as described further herein. Among other things, solubilizing the analyte (i.e., NGAL) entails release of the analyte from any endogenous binding proteins present the sample. A pretreatment reagent may be homogenous (not requiring a separation step) or heterogeneous (requiring a separation step). With use of a heterogenous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte. Also, proteases, either alone or in combination with any other pretreament agents (e.g., solvents, detergents, salts, and the like) can be employed.

q) Solid Phase

A "solid phase," as used herein, refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

The terminology used herein is for the purpose of describing particular embodiments only and is not otherwise intended to be limiting.

B. GLYCOSYLATED MAMMALIAN NGAL

Glycosylated mammalian NGAL employed in the context of the present invention is as described in U.S. Provisional Application Ser. No. 60/981,470 filed Oct. 19, 2007 (incorporated by reference for its teachings regarding same). Generally, the present invention contemplates used of mammalian NGAL of any type (e.g., isolated, recombinant, mutant, wild-type, synthetic, semi-synthetic, and the like), especially mammalian NGAL that optionally is glycosylated, and particularly human NGAL as set forth herein. Such mammalian NGAL is employed, e.g., as immunogen for making antibodies, and/or in assessing binding of such antibodies.

In one embodiment, the present invention relates to the use of isolated glycosylated mammalian NGAL. More specifically, the present invention relates to glycosylated mammalian NGAL that contains at least one oligosaccharide molecule or moiety and up to ten (10) oligosaccharide molecules or moieties. The glycosylated mammalian NGAL employed in the present invention includes, but is not limited to, glycosylated canine NGAL, glycosylated feline NGAL, glycosylated rat NGAL, glycosylated murine NGAL, glycosylated horse NGAL, glycosylated non-human primate NGAL and glycosylated human NGAL. Preferably, the glycosylated mammalian NGAL is human NGAL. Moreover, the glycosylated mammalian NGAL can be wild-type NGAL (namely, any wild-type mammalian NGAL, such as, but not limited to, wild-type canine NGAL, wild-type feline NGAL, wild-type rat NGAL, wild-type murine NGAL, wild-type horse NGAL, wild-type non-human primate NGAL or wild-type human NGAL). Preferably, the wild-type mammalian NGAL, is wild-type human NGAL having the amino acid sequence shown in SEQ ID NO:1 (including a signal peptide, and with the numbering of SEQ ID NO:1 beginning at the Gln residue of the mature sequence immediately following the signal peptide and any Met initiator residue) or SEQ ID NO:33 (not including a signal peptide). Alternatively, the glycosylated mammalian NGAL can be a glycosylated mutant mammalian NGAL that comprises an amino acid sequence comprising one or more amino acid substitutions, deletions or additions when compared to the corresponding amino acid sequence of the wild-type mammalian NGAL. For example, the glycosylated mammalian NGAL can be human NGAL wherein the amino acid sequence of the wild-type human NGAL (See, e.g., SEQ ID NOS:1 or 33) contains at least one amino acid substitution. Specifically, at least one amino acid substitution can be made at amino acid residue 87 of SEQ ID NOS:1 or 33. Specifically, the cysteine at amino acid 87 shown in SEQ ID NOS:1 or 33 can be replaced with a serine (See, e.g., SEQ ID NOS:2 and 30). Other substitutions for amino acids other than serine or cysteine can be made, e.g., glycine or alanine. Moreover, other amino acid substitutions, deletions or additions other than the single amino acid substitution at amino acid 87 of SEQ ID NOS:1 or 33 can be made by those skilled in the art using routine experimentation.

The mammalian NGAL employed herein (e.g., optionally glycosylated) can be made using recombinant DNA technology, by chemical synthesis or by a combination of chemical synthesis and recombinant DNA technology. Specifically, a polynucleotide sequence encoding mammalian NGAL may be constructed by isolating or synthesizing a polynucleotide sequence encoding the mammalian NGAL of interest. As mentioned above, the mammalian NGAL (e.g., optionally glycosylated) can be a wild-type mammalian NGAL or can be a mutant mammalian NGAL containing one more amino acid substitutions, deletions or additions. Such amino acid substitutions, deletions or additions can be made using routine techniques known in the art, such as by mutagenesis (for example, using site-directed mutagenesis in accordance with well known methods, e.g., as described in Nelson and Long, *Analytical Biochemistry* 180:147-151(1989), random mutagenesis, or shuffling).

The polynucleotide sequence encoding the mammalian NGAL of interest may be prepared by chemical synthesis, such as by using an oligonucleotide synthesizer, wherein oligonucleotides are designed based on the amino acid sequence of the desired mammalian NGAL (wild-type or mutant), and by preferably selecting those codons that are favored in the host cell in which the recombinant mammalian NGAL will be produced. For example, several small oligonucleotides coding for portions of the desired mammalian NGAL may be synthesized and assembled by polymerase chain reaction (PCR), ligation or ligation chain reaction (LCR). The individual oligonucleotides typically contain 5' or 3' overhangs for complementary assembly.

Once assembled (such as by synthesis, site-directed mutagenesis or another method), the polynucleotide sequence encoding the mammalian NGAL of interest may be inserted into a recombinant vector and operably linked to any control sequences necessary for expression of thereof in the desired transformed host cell.

Although not all vectors and expression control sequences may function equally well to express a polynucleotide sequence of interest and not all hosts function equally well with the same expression system, it is believed that those skilled in the art will be able to easily make a selection among these vectors, expression control sequences, optimized codons, and hosts for use in the present invention without any undue experimentation. For example, in selecting a vector, the host must be considered because the vector must be able to replicate in it or be able to integrate into the chromosome. The vector's copy number, the ability to control that copy number, and the expression of any other proteins encoded by the vector, such as antibiotic markers, should also be considered. In selecting an expression control sequence, a variety of factors can also be considered. These include, but are not limited to, the relative strength of the sequence, its controllability, and its compatibility with the polynucleotide sequence encoding the mammalian NGAL, particularly as regards potential secondary structures. Hosts should be selected by consideration of their compatibility with the chosen vector, their codon usage, their secretion characteristics, their ability to fold the polypeptide correctly, their fermentation or culture requirements, their ability (or lack thereof) to glycosylate the protein, and the ease of purification of the products coded for by the nucleotide sequence, etc.

The recombinant vector may be an autonomously replicating vector, namely, a vector existing as an extrachromosomal entity, the replication of which is independent of chromosomal replication (such as a plasmid). Alternatively, the vector can be one which, when introduced into a host cell, is integrated into the host cell genome and replicated together with the chromosome(s) into which it has been integrated.

The vector is preferably an expression vector, in which the polynucleotide sequence encoding the mammalian NGAL is operably linked to additional segments required for transcription of the polynucleotide sequence. The vector is typically derived from plasmid or viral DNA. A number of suitable expression vectors for expression in the host cells mentioned herein are commercially available or described in the literature. Useful expression vectors for eukaryotic hosts, include, but are not limited to, vectors comprising expression control sequences from SV40, bovine papilloma virus, adenovirus and cytomegalovirus. Specific vectors include, pCDNA3.1 (+)\Hyg (Invitrogen Corp., Carlsbad, Calif.) and pCI-neo (Stratagene, La Jolla, Calif., USA). Examples of expression vectors for use in yeast cells include, but are not limited to, the 2μ plasmid and derivatives thereof, the POT1 vector (See, U.S. Pat. No. 4,931,373), the pJSO37 vector (described in Okkels, *Ann. New York Acad. Sci.*, 782:202-207, (1996)) and pPICZ A, B or C (Invitrogen Corp., Carlsbad, Calif.). Examples of expression vectors for use in insect cells include, but are not limited to, pVL941, pBG311 (Cate et al., "Isolation of the Bovine and Human Genes for Mullerian Inhibiting Substance And Expression of the Human Gene In Animal Cells" *Cell*, 45:685-698 (1986), pBluebac 4.5 and pMelbac (both of which are available from Invitrogen Corp., Carlsbad, Calif.). A preferred vector for use in the invention is pJV (available from Abbott Laboratories, Abbott Bioresearch Center, Worcester, Mass.).

Other vectors that can be used allow the polynucleotide sequence encoding the mammalian NGAL to be amplified in copy number. Such amplifiable vectors are well known in the art. These vectors include, but are not limited to, those vector that can be amplified by DHFR amplification (See, for example, Kaufinan, U.S. Pat. No. 4,470,461, Kaufinan et al., "Construction Of A Modular Dihydrofolate Reductase cDNA Gene: Analysis Of Signals Utilized For Efficient Expression" *Mol. Cell. Biol.*, 2:1304-1319 (1982)) and glutamine synthetase (GS) amplification (See, for example, U.S. Pat. No. 5,122,464 and EP Patent Application 0 338,841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2μ replication genes REP 1-3 and origin of replication.

The vector may also comprise a selectable marker, namely, a gene or polynucleotide, the product of which complements a defect in the host cell, such as the gene coding for dihydrofolate reductase (DHFR) or the *Schizosaccharomyces pombe* TPI gene (See, P. R. Russell, *Gene*, 40: 125-130 (1985)), or one which confers resistance to a drug, such as, ampicillin, kanamycin, tetracycline, chloramphenicol, neomycin, hygromycin or methotrexate. For filamentous fungi, selectable markers include, but are not limited to, amdS, pyrG, arcB, niaD and sC.

As used herein, the phrase "control sequences" refers to any components, which are necessary or advantageous for the expression of mammalian NGAL. Each control sequence may be native or foreign to the nucleic acid sequence encoding the mammalian NGAL. Such control sequences include, but are not limited to, a leader, polyadenylation sequence, propeptide sequence, promoter, enhancer or upstream activating sequence, signal peptide sequence and transcription terminator. At a minimum, the control sequences include at least one promoter operably linked to the polynucleotide sequence encoding the mammalian NGAL.

As used herein, the phrase "operably linked" refers to the covalent joining of two or more polynucleotide sequences, by means of enzymatic ligation or otherwise, in a configuration relative to one another such that the normal function of the sequences can be performed. For example, a polynucleotide sequence encoding a presequence or secretory leader is operably linked to a polynucleotide sequence for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the polynucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for directing transcription in mammalian cells include the early and late promoters of SV40 and adenovirus, for example, the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, *J Mol Biol.*, 196:947-50 (1987)).

In order to improve expression in mammalian cells a synthetic intron may be inserted in the 5' untranslated region of the polynucleotide sequence encoding the mammalian NGAL. An example of a synthetic intron is the synthetic intron from the plasmid pCI-Neo (available from Promega Corporation, Wis., USA).

Examples of suitable control sequences for directing transcription in insect cells include, but are not limited to, the polyhedrin promoter, the P10 promoter, the baculovirus immediate early gene 1 promoter and the baculovirus 39K delayed-early gene promoter and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulas* glucoamylase, *A. nidulans* acetamidase, *Rhizomucor miehei* aspartic proteinase or lipase, the TPI1 terminator and the ADH3 terminator.

The polynucleotide sequence encoding the mammalian NGAL may or may not also include a polynucleotide sequence that encodes a signal peptide. The signal peptide is present when the mammalian NGAL is to be secreted from the cells in which it is expressed. Such signal peptide, if present, should be one recognized by the cell chosen for expression of the polypeptide. The signal peptide may be homologous (for example, it may be that normally associated with the mammalian NGAL of interest) or heterologous (namely, originating from another source than the mammalian NGAL of interest) to the mammalian NGAL of interest or may be homologous or heterologous to the host cell, namely, be a signal peptide normally expressed from the host cell or one which is not normally expressed from the host cell. Accordingly, the signal peptide may be prokaryotic, for example, derived from a bacterium, or eukaryotic, for example, derived from a mammalian, or insect, filamentous fungal or yeast cell.

The presence or absence of a signal peptide will, for example, depend on the expression host cell used for the production of the mammalian NGAL. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. For use in insect cells, the signal peptide may be derived from an insect gene (See, WO 90/05783), such as the lepidopteran *Manduca sexta* adipokinetic hormone precursor, (See, U.S. Pat. No. 5,023,328), the honeybee melittin (Invitrogen Corp., Carlsbad, Calif.), ecdysteroid UDP glucosyltransferase (egt) (Murphy et al., *Protein Expression and Purification* 4: 349-357 (1993), or human pancreatic lipase (hpl) (*Methods in Enzymology*, 284: 262-272 (1997)).

Specific examples of signal peptides for use in mammalian cells include murine Ig kappa light chain signal peptide (Coloma, M, *J. Imm. Methods*, 152:89-104 (1992)). For use in yeast cells suitable signal peptides include the α-factor signal peptide from *S. cerevisiae* (See, U.S. Pat. No. 4,870,008), the signal peptide of mouse salivary amylase (See, O. Hagenbuchle et al., *Nature*, 289:643-646 (1981)), a modified carboxypeptidase signal peptide (See, L. A. Valls et al., *Cell*, 48:887-897 (1987)), the yeast BAR1 signal peptide (See, WO 87/02670), and the yeast aspartic protease 3 (YAP3) signal peptide (See, M. Egel-Mitani et al., *Yeast*, 6:127-137 (1990)).

Any suitable host may be used to produce the glycosylated mammalian NGAL of the present invention, including bacteria, fungi (including yeasts), plant, insect mammal or other appropriate animal cells or cell lines, as well as transgenic animals or plants. When a non-glycosylating organism such as *E. coli* is used, the expression in *E. coli* is preferably followed by suitable in vitro glycosylation in order to produce the glycosylated mammalian NGAL of the present invention.

Examples of bacterial host cells include, but are not limited to, gram positive bacteria such as strains of *Bacillus*, for example, *B. brevis* or *B. subtilis*, *Pseudomonas* or *Streptomyces*, or gram negative bacteria, such as strains of *E. coli*. The introduction of a vector into a bacterial host cell may, for instance, be effected by protoplast transformation (See, for example, Chang et al., *Molecular General Genetics*, 168: 111-115 (1979)), using competent cells (See, for example, Young et al., *Journal of Bacteriology*, 81:823-829 (1961)), or Dubnau et al., *Journal of Molecular Biology*, 56:209-221 (1971)), electroporation (See, for example, Shigekawa et al., *Biotechniques*, 6:742-751 (1988)), or conjugation (See, for example, Koehler et al., *Journal of Bacteriology*, 169:5771-5278 (1987)).

Examples of suitable filamentous fungal host cells include, but are not limited to, strains of *Aspergillus*, for example, *A. oyzae, A. niger*, or *A. nidulans, Fusarium* or *Trichoderma*. Fungal cells may be transformed by a process involving protoplast formation, transformation of the protoplasts, and regeneration of the cell wall using techniques known to those skilled in the art. Suitable procedures for transformation of *Aspergillus* host cells are described in EP Patent Application 238 023 and U.S. Pat. No. 5,679,543. Suitable methods for transforming *Fusarium* species are described by Malardier et al., *Gene*, 78:147-156 (1989) and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al, *Journal of Bacteriology*, 153:163 (1983); and Hinnen et al., *Proceedings of the National Academy of Sciences USA*, 75:1920 (1978).

Preferably, the mammalian NGAL of the present invention is glycosylated in vivo. When the mammalian NGAL is to be glycosylated in vivo, the host cell is selected from a group of host cells capable of generating the desired glycosylation of the mammalian NGAL. Thus, the host cell may be selected from a yeast cell, insect cell, or mammalian cell.

Examples of suitable yeast host cells include strains of *Saccharomyces*, for example, *S. cerevisiae, Schizosaccharomyces, Klyveromyces, Pichia*, such as *P. pastoris* or *P. methanolica, Hansenula*, such as *H. polymorpha* or *yarrowia*. Methods for transforming yeast cells with heterologous polynucleotides and producing heterologous polypeptides therefrom are disclosed by Clontech Laboratories, Inc, Palo Alto, Calif., USA (in the product protocol for the Yeastmaker™ Yeast Tranformation System Kit), and by Reeves et al., *FEMS Microbiology Letters*, 99:193-198 (1992), Manivasakam et al., *Nucleic Acids Research*, 21:4414-4415 (1993) and Ganeva et al., *FEMS Microbiology Letters*, 121:159-164 (1994).

Examples of suitable insect host cells include, but are not limited to, a *Lepidoptora* cell line, such as *Spodoptera frugiperda* (Sf9 or Sf21) or *Trichoplusia ni* cells (High Five) (See, U.S. Pat. No. 5,077,214). Transformation of insect cells and production of heterologous polypeptides are well known to those skilled in the art.

Examples of suitable mammalian host cells include Chinese hamster ovary (CHO) cell lines, Green Monkey cell lines (COS), mouse cells (for example, NS/O), Baby Hamster Kidney (BHK) cell lines, human cells (such as, human embryonic kidney cells (for example, HEK293 (ATCC Accession No.

CRL-1573))) and plant cells in tissue culture. Preferably, the mammalian host cells are CHO cell lines and HEK293 cell lines. Another preferred host cell is the B3 cell line (e.g., Abbott Laboratories, Abbott Bioresearch Center, Worcester, Mass.), or another dihydrofolate reductase deficient (DHFR⁻) CHO cell line (e.g., available from Invitrogen Corp., Carlsbad, Calif.). In one aspect, the present invention relates to a CHO cell line which produces glycosylated human wild-type NGAL (namely, that which has the amino acid sequence of SEQ ID NOS:1 or 33), wherein the CHO cell line has been deposited with American Type Culture Collection (ATCC) on Nov. 21, 2006 and received ATCC Accession No. PTA-8020. Preferably, the wild-type human NGAL produced by the CHO cell line having ATCC Accession No. PTA-8020 has a molecular weight of about 25 kilodaltons (kDa). In another aspect, the present invention relates to a CHO cell line which produces glycosylated mutant human NGAL. Preferably, the glycosylated mutant human NGAL comprises an amino acid substitution at the amino acid corresponding to amino acid 87 of the amino acid sequence of wild-type human NGAL (namely, SEQ ID NOS:1 or 33). More preferably, the amino acid substitution is the replacement of a cysteine with a serine (See, SEQ ID NOS:2 or 30). Most preferably, the CHO cell line is a CHO cell line that has been deposited with the ATCC on Jan. 23, 2007 and received ATCC Accession No. PTA-8168. The CHO cell line having ATCC Accession No. PTA-8168 produces a glycosylated mutant human NGAL comprising an amino acid sequence of SEQ ID NOS:2 or 30. In yet another aspect, the present invention relates to an isolated mutant glycosylated human NGAL comprising the amino acid sequence of SEQ ID NOS:2 or 30.

Methods for introducing exogenous polynucleotides into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamine™ 2000. These methods are well known in the art and are described, for example by Ausbel et al. (eds.) *Current Protocols in Molecular Biology* John Wiley & Sons, New York, USA (1996). The cultivation of mammalian cells are conducted according to established methods, e.g. as disclosed in Jenkins, Ed., *Animal Cell Biotechnology, Methods and Protocols*, Human Press Inc. Totowa, N.J., USA (1999) and Harrison and Rae *General Techniques of Cell Culture*, Cambridge University Press (1997).

In the production methods, cells are cultivated in a nutrient medium suitable for production of the mammalian NGAL using methods known in the art. For example, cells are cultivated by shake flask cultivation, small-scale or large-scale fermentation (including continuous, batch, fed-batch, or solid state fermentations) in laboratory or industrial fermenters performed in a suitable medium and under conditions allowing the glycosylated mammalian NGAL to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the glycosylated mammalian NGAL is secreted into the nutrient medium, the mammalian NGAL can be recovered directly from the medium. If the mammalian NGAL is not secreted, it can be recovered from cell lysates.

The resulting mammalian NGAL may be recovered by methods known in the art. For example, the mammalian NGAL may be recovered from the nutrient medium by conventional procedures including, but not limited to, centrifugation, filtration, extraction, spray drying, evaporation, or precipitation.

The mammalian NGAL may be purified by a variety of procedures known in the art including, but not limited to, chromatography (such as, but not limited to, ion exchange, affinity, hydrophobic, chromatofocusing, and size exclusion), electrophoretic procedures (such as, but not limited to, preparative isoelectric focusing), differential solubility (such as, but not limited to, ammonium sulfate precipitation), SDS-PAGE, or extraction (See, for example, J-C Janson and Lars Ryden, editors, *Protein Purification*, VCH Publishers, New York (1989)).

The glycosylated mammalian NGAL (wild-type and mutant) described herein can be used for a variety of different purposes and in a variety of different ways. Specifically, the glycosylated mammalian NGAL described herein can be used as one or more calibrators, one or more controls or as a combination of one or more calibrators or controls in an assay, preferably, an immunoassay, for detecting mammalian NGAL in a test sample. This is the subject matter of U.S. Provisional Application Ser. No. 60/981,470 filed Oct. 19, 2007 (incorporated by reference for its teachings regarding antigens, calibrators, controls, and kits), and of U.S. Provisional Application Ser. No. 60/981,473 filed Oct. 19, 2007 (incorporated by reference for its teachings regarding improved NGAL assays).

Preferably, the glycosylated mammalian NGAL comprises the amino acid sequence of SEQ ID NOS:1 or 33. Alternatively, the glycosylated mammalian NGAL comprises the amino acid sequence of SEQ ID NOS:2 or 30.

Furthermore, and as discussed further herein, the mammalian NGAL can be employed as immunogen to immunize animals for antibody production, e.g., where the animal can be a murine, rabbit, chicken, rat, sheep, goat, shark, camel, horse, feline canine, non-human primate, human or other animal. In one embodiment, the immunogen comprises glycosylated mammalian NGAL, especially glycosylated human NGAL comprising the sequence of SEQ ID NO: 1, 2, 30 or 33. In another embodiment, the mammalian NGAL is that of a canine, feline, rat, murine, horse, non-human primate, human, or other mammal.

C. HUMAN NGAL ANTIBODIES

The present invention provides antibodies that specifically bind to wild-type human NGAL (namely, SEQ ID NOS:1 or 33) or human NGAL fragment. The antibodies also optionally bind to human NGAL wherein the amino acid sequence contains at least one amino acid substitution of the wild-type sequence (SEQ ID NOS:1 or 33) so as to comprise a mutant or non-native sequence (e.g., SEQ ID NOS:2 or 30).

In particular, in one aspect, the present invention provides for isolated antibodies that bind to an epitope, particularly a conformational epitope, comprising (or in some embodiments consisting of) the noncontiguous amino acid residues 112, 118 and 147 of wild-type human NGAL (namely, SEQ ID NOS:1 or 33; with the numbering of SEQ ID NO:1 beginning at the Gln residue of the mature sequence immediately following the signal peptide and any Met initiator residue). As described herein, a conformational epitope (also known as a discontinuous epitope) is a type of epitope formed by residues that are sequentially discontinuous but close together in three-dimensional space. In another aspect, the present invention provides for isolated antibodies that bind to a conformational epitope comprising amino acid residues 112, 118 and 147 of wild-type human NGAL (namely, SEQ ID NOS:1 or 33) and at least one (1) additional amino acid of human NGAL protein, wherein the additional amino acid is amino acid residue 117 or 119 of wild-type human NGAL (namely, SEQ ID NOS:1 or 33). In yet another aspect, the present invention provides for isolated antibodies that bind to a conformational epitope comprising amino acid residues 112, 117, 118, 119 and 147 of wild-type human NGAL (namely, SEQ ID NOS:1 or 33).

In another aspect, the present invention relates to an isolated antibody that specifically binds to wild-type human NGAL, wherein the antibody has a variable heavy domain region comprising an amino acid sequence of SEQ ID NO:7.

In another aspect, the present invention relates to an isolated antibody that specifically binds to wild-type human NGAL, wherein the antibody has a variable heavy domain region comprising an amino acid sequence of SEQ ID NO:7 and further wherein the antibody binds to: (1) amino acid residues 112, 118 and 147 of wild-type human NGAL protein (namely, SEQ ID NOS:1 or 33); (2) amino acid residues 112, 118 and 147 of wild-type human NGAL protein (namely, SEQ ID NOS:1 or 33) and at least one additional amino acid of wild-type human NGAL protein, wherein the additional amino acid is amino acid residue 117 of 119 of wild-type human NGAL (namely, SEQ ID NOS:1 or 33); or (3) to a conformational epitope comprising amino acid residues 112, 117, 118, 119 and 147 of wild-type human NGAL (namely, SEQ ID NOS:1 or 33).

In another aspect, the present invention relates to an isolated antibody that specifically binds to wild-type human NGAL, wherein the antibody has a variable light domain region comprising an amino acid sequence of SEQ ID NO:11.

In another aspect, the present invention relates to an isolated antibody that specifically binds to wild-type human NGAL, wherein the antibody has a variable light domain region comprising an amino acid sequence of SEQ ID NO:11 and further wherein the antibody binds to: (1) amino acid residues 112, 118 and 147 of wild-type human NGAL protein (namely, SEQ ID NOS:1 or 33); (2) amino acid residues 112, 118 and 147 of wild-type human NGAL protein (namely, SEQ ID NOS:1 or 33) and at least one additional amino acid of wild-type human NGAL protein, wherein the additional amino acid is amino acid residue 117 of 119 of wild-type human NGAL (namely, SEQ ID NOS:1 or 33); or (3) to a conformational epitope comprising comprising amino acid residues 112, 117, 118, 119 and 147 of wild-type human NGAL (namely, SEQ ID NOS:1 or 33).

In another aspect, the present invention relates to an isolated antibody that specifically binds to wild-type human NGAL, wherein the antibody has a variable heavy domain region comprising an amino acid sequence of SEQ ID NO:7 and a variable light domain region comprising an amino acid sequence of SEQ ID NO:11.

In another aspect, the present invention relates to an isolated antibody that specifically binds to wild-type human NGAL, wherein the antibody has a variable heavy domain region comprising an amino acid sequence of SEQ ID NO:7 and a variable light domain region comprising an amino acid sequence of SEQ ID NO:11 and further wherein the antibody binds to: (1) amino acid residues 112, 118 and 147 of wild-type human NGAL protein (namely, SEQ ID NOS:1 or 33); (2) amino acid residues 112, 118 and 147 of wild-type human NGAL protein (namely, SEQ ID NOS:1 or 33) and at least one additional amino acid of wild-type human NGAL protein, wherein the additional amino acid is amino acid residue 117 of 119 of wild-type human NGAL (namely, SEQ ID NOS:1 or 33); or (3) to a conformational epitope comprising amino acid residues 112, 117, 118, 119 and 147 of wild-type human NGAL (namely, SEQ ID NOS:1 or 33).

In yet another aspect, the present invention relates to murine hybridoma cell line 1-2322-455 having ATCC Accession No. PTA-8024, deposited on Nov. 21, 2006. In yet another aspect, the present invention relates to an antibody produced by murine hybridoma cell line 1-2322-455 having ATCC Accession No. PTA-8024, deposited on Nov. 21, 2006. The antibody produced by murine hybridoma cell line 1-2322-455 can bind to: (1) amino acid residues 112, 118 and 147 of wild-type human NGAL protein (namely, SEQ ID NOS:1 or 33); (2) amino acid residues 112, 118 and 147 of wild-type human NGAL protein (namely, SEQ ID NOS:1 or 33) and at least one additional amino acid of human NGAL protein, wherein the additional amino acid is amino acid residue 117 of 119 of wild-type human NGAL (namely, SEQ ID NOS:1 or 33); or (3) to a conformational epitope comprising amino acid residues 112, 117, 118, 119 and 147 of wild-type human NGAL (namely, SEQ ID NOS:1 or 33). Murine hybridoma cell line 1-2322-455 has a variable heavy domain comprising the amino acid sequence of SEQ ID NO:7 and a variable light domain comprising the amino acid sequence of SEQ ID NO:11.

In yet another aspect, the present invention relates to an isolated antibody that specifically binds to wild-type human NGAL, wherein the antibody has a variable heavy domain region comprising an amino acid sequence of SEQ ID NO:17.

In yet another aspect, the present invention relates to an isolated antibody that specifically binds to wild-type human NGAL, wherein the antibody has a variable heavy domain region comprising an amino acid sequence of SEQ ID NO:17 and further wherein the antibody binds to (1) amino acid residues 15 and 109 of wild-type human NGAL protein (namely, SEQ ID NOS:1 or 33); (2) amino acid residues 15 and 109 of wild-type human NGAL protein (namely, SEQ ID NOS:1 or 33) and at least one additional amino acid of wild-type human NGAL protein, wherein the additional amino acid is amino acid residue 158, 159 or 160 of wild-type human NGAL (namely, SEQ ID NOS:1 or 33); or (3) to a conformational epitope comprising amino acid residues 15, 109, 158, 159 or 160 of wild-type human NGAL (namely, SEQ ID NOS:1 or 33).

In yet another aspect, the present invention relates to an isolated antibody that specifically binds to wild-type human NGAL, wherein the antibody has a variable light domain region comprising an amino acid sequence of SEQ ID NO:21.

In yet another aspect, the present invention relates to an isolated antibody that specifically binds to wild-type human NGAL, wherein the antibody has a variable light domain region comprising an amino acid sequence of SEQ ID NO:21 and further wherein the antibody binds to (1) amino acid residues 15 and 109 of wild-type human NGAL protein (namely, SEQ ID NOS:1 or 33); (2) amino acid residues 15 and 109 of wild-type human NGAL protein (namely, SEQ ID NOS:1 or 33) and at least one additional amino acid of wild-type human NGAL protein, wherein the additional amino acid is amino acid residue 158, 159 or 160 of wild-type human NGAL (namely, SEQ ID NOS:1 or 33); or (3) to a conformational epitope comprising amino acid residues 15, 109, 158, 159 or 160 of wild-type human NGAL (namely, SEQ ID NOS:1 or 33).

In another aspect, the present invention relates to an isolated antibody that specifically binds to wild-type human NGAL, wherein the antibody has a variable heavy domain region comprising an amino acid sequence of SEQ ID NO:17 and a variable light domain region comprising an amino acid sequence of SEQ ID NO:21.

In another aspect, the present invention relates to an isolated antibody that specifically binds to wild-type human NGAL, wherein the antibody has a variable heavy domain region comprising an amino acid sequence of SEQ ID NO:17 and a variable light domain region comprising an amino acid sequence of SEQ ID NO:21 and further wherein the antibody binds to: (1) amino acid residues 15 and 109 of wild-type human NGAL protein (namely, SEQ ID NOS:1 or 33); (2) amino acid residues 15 and 109 of wild-type human NGAL protein (namely, SEQ ID NOS:1 or 33) and at least one additional amino acid of wild-type human NGAL protein, wherein the additional amino acid is amino acid residue 158, 159 or 160 of wild-type human NGAL (namely, SEQ ID NOS:1 or 33); or (3) to a conformational epitope comprising amino acid residues 15, 109, 158, 159 or 160 of wild-type human NGAL (namely, SEQ ID NOS:1 or 33).

In yet another aspect, the present invention relates to murine hybridoma cell line 1-903-430 having ATCC Accession No. PTA-8026, deposited on Nov. 21, 2006. In yet another aspect, the present invention relates to an antibody produced by murine hybridoma cell line 1-903-430 having ATCC Accession No. PTA-8026, deposited on Nov. 21, 2006. The antibody produced by murine hybridoma cell line 1-903-430 can bind to: (1) amino acid residues 15 and 109 of wild-type human NGAL protein (namely, SEQ ID NOS:1 or 33); (2) amino acid residues 15 and 109 of wild-type human NGAL protein (namely, SEQ ID NOS:1 or 33) and at least one additional amino acid of wild-type human NGAL protein, wherein the additional amino acid is amino acid residue 158, 159 or 160 of wild-type human NGAL (namely, SEQ ID NOS:1 or 33); or (3) to a conformational epitope comprising amino acid residues 15, 109, 158, 159 or 160 of wild-type human NGAL (namely, SEQ ID NOS:1 or 33). Murine hybridoma cell line 1-903-430 has a variable heavy domain comprising the amino acid sequence of SEQ ID NO:17 and a variable light domain comprising the amino acid sequence of SEQ ID NO:21.

In still yet another embodiment, the present invention relates to an isolated antibody that specifically binds to a human NGAL protein as set forth in SEQ ID NOS:1, 2, 30 or 33 (especially as set forth in SEQ ID NOS: 30 or 33), wherein as a result of adding the antibody to the human NGAL protein (generally done in excess, particularly stoichiometric excess), the antibody causes as compared to when the antibody is not added, (1) a perturbation of from about 0.05 ppm to about 1.0 ppm in a $^1$H resonance position, particularly from about 0.04 ppm to about 0.06 ppm, especially of about 0.05 ppm in a $^1$H resonance position, (2) a perturbation of from about 0.3 ppm to about 3.0 ppm in a $^{15}$N resonance position, particularly of from about 0.1 ppm to about 2.0 ppm, especially of about 0.1 ppm, about 0.3 ppm, or about 0.6 ppm in a $^{15}$N resonance position, or (3) from about a 2.5-fold to about a 20-fold decrease in resonance intensity, especially from about a 3-fold to about a 15-fold decrease, and particularly about a 4-fold to about a 10-fold decrease in resonance intensity, in a TROSY proton-nitrogen correlation NMR spectra of at least three, four or five of the amide resonance positions for amino acids corresponding to residues of SEQ ID NOS:1 or 33, particularly from about two to six of the amide resonance positions for amino acids corresponding to residues of SEQ ID NOS:1, 2, 30 or 33 (especially of SEQ ID NOS: 30 or 33), selected from the group consisting of:

(a) for residue N116, a resonance position located at about $^1$H=9.47 or about $^{15}$N=118.30;

(b) for residue Q117, a resonance position located at about $^1$H=7.79 or about $^{15}$N=117.67;

(c) for residue H118, a resonance position located at about $^1$H=8.75 or about $^{15}$N=116.43;

(d) for residue T141, a resonance position located at about $^1$H=7.99 or about $^{15}$N=109.06;

(e) for residue K142, a resonance position located at about $^1$H=7.82 or about $^{15}$N=114.25;

(f) for residue E143, a resonance position located at about $^1$H=7.40 or about $^{15}$N=114.00; and (g) for residue E150, a resonance position located at about $^1$H=8.70 or about $^{15}$N=118.80. In other words, the shifts are in resonance positions that correspond to residues in the wild-type NGAL protein.

In still yet another embodiment, the present invention relates to an isolated antibody that specifically binds to a human NGAL protein as set forth in SEQ ID NOS:1, 2, 30 or 33 (especially as set forth in SEQ ID NOS: 30 or 33), wherein as a result of adding the antibody to the human NGAL protein (generally done in excess, particularly stoichiometric excess), the antibody causes as compared to when the antibody is not added, (1) a perturbation of from about 0.05 ppm to about 1.0 ppm in a $^1$H resonance position, particularly from about 0.04 ppm to about 0.06 ppm, especially of about 0.05 ppm in a $^1$H resonance position, (2) a perturbation of from about 0.3 ppm to about 3.0 ppm in a $^{15}$N resonance position, particularly of from about 0.1 ppm to about 2.0 ppm, especially of about 0.1 ppm, about 0.3 ppm, or about 0.6 ppm in a $^{15}$N resonance position, or (3) from about a 2.5-fold to about a 20-fold decrease in resonance intensity, especially from about a 3-fold to about a 15-fold decrease, and particularly about a 4-fold to about a 10-fold decrease in resonance intensity, in a TROSY proton-nitrogen correlation NMR spectra of at least three, four or five of the amide resonance positions for amino acids corresponding to residues of SEQ ID NOS:1 or 33, particularly from about two to six of the amide resonance positions for amino acids corresponding to residues of SEQ ID NOS:1, 2, 30 or 33 (especially of SEQ ID NOS: 30 or 33), selected from the group consisting of:

(a) for residue Y64, a resonance position located at about $^1$H=9.15 or about $^{15}$N=113.30;

(b) for residue V84, a resonance position located at about $^1$H=9.34 or about $^{15}$N=121.50;

(c) for residue G86, a resonance position located at about $^1$H=8.32 or about $^{15}$N=111.60;

(d) for residue T93, a resonance position located at about $^1$H=9.32 or about $^{15}$N=112.80;

(e) for residue L94, a resonance position located at about $^1$H=7.71 or about $^{15}$N=122.72;

(f) for residue G95, a resonance position located at about $^1$H=9.30 or about $^{15}$N=113.70; and (g) for residue S99, a resonance position located at about $^1$H=8.18 or about $^{15}$N=114.50.

D. METHODS OF MAKING AND USING NGAL ANTIBODIES

The antibodies of the present invention can be made using a variety of different techniques known in the art. For example, polyclonal and monoclonal antibodies against wild-type human NGAL can be raised by immunizing a suitable subject (such as, but not limited to, a rabbit, goat, murine or other mammal) with an immunogenic preparation which contains a suitable immunogen. The immunogen that can be used for the immunization can include cells such as cells from immortalized cell lines NSO which is known to express human NGAL.

Alternatively, the immunogen can be the purified or isolated human wild-type NGAL protein itself (namely, SEQ ID NOS:1 or 33) or a human NGAL fragment thereof. For example, wild-type human NGAL (See, SEQ ID NOS:1 or 33) that has been isolated from a cell which produces the protein (such as NSO) using affinity chromatography, immunoprecipitation or other techniques which are well known in the art, can be used as an immunogen. Alternatively, immunogen can be prepared using chemical synthesis using routine techniques known in the art (such as, but not limited to, a synthesizer).

The antibodies raised in the subject can then be screened to determine if the antibodies bind to wild-type human NGAL or human NGAL fragment. Such antibodies can be further screened using the methods described herein (See, e.g., Example 1). For example, these antibodies can be assayed to determine if they bind to amino acid residues 112, 118 and 147 of wild-type human NGAL or amino acid residues 15 and 109 of wild-type human NGAL (See, SEQ ID NOS:1 or 33). Suitable methods to identify an antibody with the desired characteristics are described herein (See, Example, 1). Moreover, it is fully anticipated that results obtained with antibodies that bind to mutant NGAL (See, SEQ ID NOS:2 or 30). are fully translatable to binding of wild-type NGAL, and that antibodies will bind to comparable residues of wild-type human NGAL (See, SEQ ID NOS:1 or 33). Accordingly, for convenience, and unless there lacks a rational basis in a particular instance for not doing so, mutant NGAL can be employed to assess binding properties of antibodies.

The unit dose of immunogen (namely, the purified protein, tumor cell expressing the protein, or recombinantly expressed human NGAL protein) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen, namely, human NGAL (SEQ ID NOS:1 or 33, or human NGAL fragment thereof) as described herein.

Other methods of raising antibodies against human NGAL (SEQ ID NOS:1 or 33, or a human NGAL fragment thereof) include using transgenic mice which express human immunoglobin genes (See, for example, WO 91/00906, WO 91/10741 or WO 92/03918). Alternatively, human monoclonal antibodies can be produced by introducing an antigen into immune deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (See, for example, WO 93/05796, U.S. Pat. No. 5,411, 749; or McCune et al., *Science,* 241:1632-1639 (1988)) or Rag-1/Rag-2 deficient mice. Human antibody-immune deficient mice are also commercially available. For example, Rag-2 deficient mice are available from Taconic Farms (Germantown, N.Y.).

Monoclonal antibodies can be generated by immunizing a subject with an immunogen. At the appropriate time after immunization, for example, when the antibody titers are at a sufficiently high level, antibody producing cells can be harvested from an immunized animal and used to prepare monoclonal antibodies using standard techniques. For example, the antibody producing cells can be fused by standard somatic cell fusion procedures with immortalizing cells such as myeloma cells to yield hybridoma cells. Such techniques are well known in the art, and include, for example, the hybridoma technique as originally developed by Kohler and Milstein, *Nature,* 256:495497 (1975)), the human B cell hybridoma technique (Kozbar et al., *Immunology Today,* 4:72 (1983)), and the EBV-hybridoma technique to produce human monoclonal antibodies (Cole et al., *Monoclonal Antibodies and Cancer Therapy*, Alan R. Liss, Inc. pp. 77-96 (1985)). The technology for producing monoclonal antibody hybridomas is well known to those skilled in the art.

Monoclonal antibodies can also be made by harvesting antibody producing cells, for example, splenocytes, from transgenic mice expressing human immunoglobulin genes and which have been immunized with the human NGAL protein. The splenocytes can be immortalized through fusion with human myelomas or through transformation with Epstein-Barr virus (EBV). These hybridomas can be made using human B cell- or EBV-hybridoma techniques described in the art (See, for example, Boyle et al., European Patent Publication No. 0 614 984).

Hybridoma cells producing a monoclonal antibody which specifically binds to the wild-type human NGAL protein (SEQ ID NOS:1 or 33) or a human NGAL fragment thereof are detected by screening the hybridoma culture supernatants by, for example, screening to select antibodies that specifically bind to the immobilized human NGAL protein, or by testing the antibodies as described herein to determine if the antibodies have the desired characteristics, namely, the ability to bind to human NGAL at the amino acid residues described herein. After hybridoma cells are identified that produce antibodies of the desired specificity, the clones may be subcloned, e.g., by limiting dilution procedures, for example the procedure described by Wands et al. (*Gastroenterology* 80:225-232 (1981)), and grown by standard methods.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (See, for example, R. H. Kenneth, in *Monoclonal Antibodies: A New Dimension In Biological Analyses*, Plenum Publishing Corp., New York, N.Y. (1980)). Conditioned hybridoma culture supernatant containing the antibody can then be collected. The monoclonal antibodies secreted by the subclones optionally can be isolated from the culture medium by conventional immunoglobulin purification procedures such as, for example, protein A chromatography, hydroxylapatite chromatography, gel electrophoresis, dialysis, or affinity chromatography.

Monoclonal antibodies can be engineered by constructing a recombinant combinatorial immunoglobulin library and screening the library with the human NGAL protein. Kits for generating and screening phage display libraries are commercially available (See, for example, the Pharmacia Recombinant Phage Antibody System, Catalog No. 27-9400-01; and the Stratagene SurfZAP Phage Display Kit, Catalog No. 240612). Likewise, yeast display vectors are known in the art and are commercially available (for example, pYD1 available from Invitrogen Corp., Carlsbad, Calif.). Briefly, the antibody library is screened to identify and isolate phages or yeast cells that express an antibody that specifically binds to the wild-type human NGAL protein (SEQ ID NOS:1 or 33). Preferably, the primary screening of the library involves screening with an immobilized wild-type human NGAL protein or a fragment thereof.

Following screening, the display phage or yeast is isolated and the polynucleotide encoding the selected antibody can be recovered from the display phage or yeast (for example, from the phage or yeast genome) and subcloned into other expression vectors (e.g., into Saccharomyces cerevesiae cells, for example EBY100 cells (Invitrogen Corporation, Carlsbad, Calif.)) by well known recombinant DNA techniques. The polynucleotide can be further manipulated (for example, linked to nucleic acid encoding additional immunoglobulin domains, such as additional constant regions) and/or expressed in a host cell.

Alternatively, recombinant forms of antibodies, such as chimeric and humanized antibodies, can also be prepared to minimize the response by a human patient to the antibody. When antibodies produced in non-human subjects or derived from expression of non-human antibody genes are used therapeutically in humans, they are recognized to varying degrees as foreign, and an immune response may be generated in the patient. One approach to minimize or eliminate this immune reaction is to produce chimeric antibody derivatives, namely, antibody molecules that combine a non-human animal variable region and a human constant region. Such antibodies retain the epitope binding specificity of the original monoclonal antibody, but may be less immunogenic when administered to humans, and therefore more likely to be tolerated by the patient.

Chimeric monoclonal antibodies can be produced by recombinant DNA techniques known in the art. For example, a gene encoding the constant region of a non-human antibody molecule is substituted with a gene encoding a human constant region (See, for example, PCT Patent Publication PCT/US86/02269, European Patent Application 184,187 or European Patent Application 171,496).

A chimeric antibody can be further "humanized" by replacing portions of the variable region not involved in antigen binding with equivalent portions from human variable regions. General reviews of "humanized" chimeric antibodies can be found in Morrison, S. L., Science, 229:1202-1207 (1985) and in Oi et al., BioTechniques, 4-214 (1986). Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Suitable "humanized" antibodies can be alternatively produced by complementarity determining region (CDR) substitution (See, for example, U.S. Pat. No. 5,225,539; Jones et al., Nature, 321:552-525 (1986); Verhoeyan et al., Science 239:1.534 (1988); and Beidler et al., J. Immunol, 141:4053-4060 (1988)).

Epitope imprinting can also be used to produce a "human" antibody polypeptide dimer that retains the binding specificity of the antibodies (e.g., hamster antibodies) specific for the wild-type human NGAL protein (SEQ ID NOS:1 or 33) or human NGAL fragment thereof. Briefly, a gene encoding a non-human variable region (VH) with specific binding to an antigen and a human constant region (CH1), is expressed in E. coli and infected with a phage library of human Vλ.Cλ genes. Phage displaying antibody fragments are then screened for binding to the human NGAL protein. Selected human Vλ genes are recloned for expression of Vλ.Cλ. chains and E. coli harboring these chains are infected with a phage library of human VHCH1 genes and the library is subject to rounds of screening with antigen coated tubes (See, WO 93/06213).

In another aspect, the present invention contemplates that the antibody is an antibody fragment. For example, the antibody fragment can include, but is not limited to, a Fab, a Fab', a Fab'-SH fragment, a di-sulfide linked Fv, a single chain Fv (scFv) and a F(ab')$_2$ fragment. Various techniques are known to those skilled in the art for the production of antibody fragments. For example, such fragments can be derived via proteolytic digestion of intact antibodies (See, for example, Morimoto et al., J. Biochem. Biophys. Methods, 24:107-117 (1992) and Brennan et al., Science, 229:81 (1985)) or produced directly by recombinant host cells. For example, Fab'-SH fragments can be directly recovered from E. coli and chemically coupled to form F(ab')$_2$ fragments (See, Carter et al., Bio/Technology, 10:163-167 (1992)). In another embodiment, the F(ab')$_2$ is formed using the leucine zipper GCN4 to promote assembly of the F(ab')$_2$ molecule. Alternatively, Fv, Fab or F(ab')$_2$ fragments can be isolated directly from recombinant host cell culture. Single chain variable region fragments (scFv) are made by linking light and/or heavy chain variable regions by using a short linking peptide (See, Bird et al. Science, 242:423-426 (1998)). An example of a linking peptide is GPAKELTPLKEAKVS (SEQ ID NO:31). Linkers can in turn be modified for additional functions, such as attachment of drugs or attachment to solid supports. Examples of other linker sequences that can be used in the present invention can be found in Bird et al., Science, 242: 423-426 (1988), Huston et al., Proc. Natl. Acad. Sci. USA, 85:5879-5883 (1988) and McCafferty et al., Nature, 348:552-554 (1990).

The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art. Moreover, other forms of single chain antibodies, such as diabodies are also contemplated by the present invention. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (See, for example, Holliger, P., et al., Proc. Natl. Acad. Sci. USA, 90:6444-6448 (1993); Poljak, R. J., et al., Structure, 2:1121-1123 (1994)).

Furthermore, in some aspects of the invention(s) as described herein (e.g., use as controls), it may be possible to employ commercially available anti-NGAL antibodies, or anti-NGAL antibodies or their methods for production described in the literature. These include but are not limited to: (1) anti-NGAL monoclonal antibodies (either HYB 211-01, HYB 211-02, or HYB 211-05, commercially available from AntibodyShop A/S, Gentofte, Denmark); (2) mouse anti-NGAL monoclonal antibody (e.g., Clone No. 697, Catalog No. HM2193B, HyCult Biotechnology, Uden, Netherlands); (3) rat anti-NGAL monoclonal antibody (e.g., Clone No. 220310, Catalog No. MAB1757, R&D Systems, Minneapolis, Minn.); (4) anti-NGAL antibodies contained in Quantikine® NGAL ELISA kit DLCN20 (R&D Systems, Minneapolis, Minn.), which purportedly detect the free NGAL form (i.e., form not complexed in a heterodimer) (U.S. Patent Application Publication No. 2007/0196876); (5) rabbit anti-human NGAL monoclonal antibodies produced in mouse hybridoma cells (EP 0 756 708 and U.S. Pat. No. 6,136,526); (6) purified monoclonal or polyclonal antibody against human NGAL (Kjeldsen et al., J. Biolog. Chem., 268:10425-32 (1993); Kjeldsen et al., J. Immunolog. Methods, 198(2): 155-64 (1996)); (7) polyclonal antibody against human NGAL (PCT International Application WO 2002/031507); and/or (8) discussing the use of solvent-exposed peptide loop areas of NGAL for making monoclonal antibody against human NGAL (U.S. Pat. No. 7,056,702 and U.S. Patent Application Publication US2004/0115728).

The antibodies of the present invention have a variety of uses. In one aspect, the antibodies of the present invention can be used as one or more immunodiagnostic reagents. For example, the antibodies of the present invention can be used as one or more immunodiagnostic reagents in one or more methods for detecting the presence of human NGAL antigen in a test sample. More specifically, the antibodies of the present invention can be used as one or more capture antibodies, one or more conjugate antibodies or as both one or more capture antibodies and one or more conjugate antibodies in immunoassays to detect the presence of human NGAL in a test sample.

E. SAMPLE COLLECTION AND PRETREATMENT

Methods well known in the art for collecting, handling and processing urine, blood, serum and plasma, and other body fluids, are used in the practice of the present invention, for instance, when the antibodies according to the invention are employed as immunodiagnostic reagents, and/or in an NGAL immunoassay kit.

The test sample may comprise further moieties in addition to the NGAL analyte of interest such as antibodies, antigens, haptens, hormones, drugs, enzymes, receptors, proteins, peptides, polypeptides, oligonucleotides or polynucleotides. For example, the sample may be a whole blood sample obtained from a subject. It may be necessary or desired that a test sample, particularly whole blood, be treated prior to immunoassay as described herein, e.g., with a pretreatment reagent. Even in cases where pretreatment is not necessary (e.g., most urine samples), pretreatment optionally may be done for mere convenience (e.g., as part of a regimen on a commercial platform). The pretreatment reagent can be a heterogeneous agent or a homogeneous agent.

With use of a heterogenous pretreatment reagent according to the invention, the pretreatment reagent precipitates analyte binding protein (e.g., protein capable of binding NGAL) present in the sample. Such a pretreatment step comprises removing any analyte binding protein by separating from the precipitated analyte binding protein the supernatant of the mixture formed by addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with the capture antibody in the antibody capture step. The pretreatment reagent employed for such an assay typically is diluted in the pretreated test sample mixture, either before the antibody capture step or during encounter with the antibody in the antibody capture step. Despite such dilution, a certain amount of the pretreatment reagent (for example, 5 M methanol and/or 0.6 M ethylene glycol) is still present (or remains) in the test sample mixture during antibody capture.

The pretreatment reagent can be any reagent appropriate for use with the immunoassay and kits of the invention. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, *Clin. Chem.*, 36:1969-1973 (1990) and Wallemacq et al., Evaluation of the New AxSYM Cyclosporine Assay:Comparison with TDx Monoclonal Whole Blood and EMIT Cyclosporine Assays, *Clin. Chem.* 45: 432-435 (1999)), and/or as commercially available. Additionally, pretreatment can be done as described in Abbott's U.S. Pat. No. 5,135,875, EP 0 471 293, U.S. Patent Application 60/878,017 filed Dec. 29, 2006; and U.S. patent application Ser. No. 11/490,624 filed Jun. 21, 2006 (incorporated by reference in its entirety for its teachings regarding pretreatment). Also, proteases, either alone or in combination with any other pretreatment agents (e.g., solvents, detergents, salts, and the like) can be employed.

F. NGAL IMMUNOASSAYS

Immunoassays can be conducted using any format known in the art, such as, but not limited to, a sandwich format. Specifically, in one aspect of the present invention, at least two antibodies are employed to separate and quantify human NGAL or human NGAL fragment in a test sample. More specifically, the at least two antibodies bind to certain epitopes of human NGAL or human NGAL fragment forming an immune complex which is referred to as a "sandwich". Generally, in the immunoassays one or more antibodies can be used to capture the human NGAL or human NGAL fragment in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody", "detection antibodies", a "conjugate" or "conjugates").

The antibodies of the present invention can be employed as an immunodiagnostic agent, e.g., in a method for detecting the presence of human NGAL antigen in a test sample. Such use and assays are described in U.S. Provisional Application Ser. No. 60/981,473 filed Oct. 19, 2007 (incorporated by reference for its teachings regarding such assays). Excellent immunoassays, particularly, sandwich assays, can be performed using the antibodies of the present invention as the capture antibodies, detection antibodies or as capture and detection antibodies. Other particular assays using the antibodies of the present invention are set forth as described in U.S. Provisional Application Ser. No. 60/981,473 filed Oct. 19, 2007 (incorporated by reference for its teachings regarding such assays).

The test sample being tested for (for example, suspected of containing) human NGAL or human NGAL fragment can be contacted with at least one capture antibody (or antibodies) and at least one detection antibody (which is either a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a test sample suspected of containing human NGAL or human NGAL fragment is first brought into contact with an at least one first capture antibody under conditions which allow the formation of a first antibody/human NGAL complex. If more than one capture antibody is used, a first multiple capture antibody/human NGAL complex is formed. In a sandwich assay, the antibodies, preferably, the at least one capture antibody, are used in molar excess amounts of the maximum amount of human NGAL or human NGAL fragment expected in the test sample. For example, from about 5 µg/mL to about 1 mg/mL of antibody per mL of buffer (e.g., microparticle coating buffer) can be used.

Optionally, prior to contacting the test sample with the at least one capture antibody (for example, the first capture antibody), the at least one capture antibody can be bound to a solid support which facilitates the separation the first antibody/human NGAL complex from the test sample. Any solid support known in the art can be used, including, but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind human NGAL or human NGAL fragment. Alternatively, the antibody (or antibodies) can be bound with microparticles that have previously coated with streptavidin or biotin (for example, using Power-Bind™-SA-MP streptavidin coated microparticles, available from Seradyn, Indianapolis, Ind.). Alternatively, the antibody (or antibodies) can be bound using microparticles that have been previously coated with anti-species specific monoclonal antibodies. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample being tested for and/or suspected of containing human NGAL or a human NGAL fragment is brought into contact with the at least one capture antibody (for example, the first capture antibody), the mixture is incubated in order to allow for the formation of a first antibody (or multiple antibody)-human NGAL complex. The incubation can be carried out at a pH of from about 4.5 to about 10.0, at a temperature of from about 2° C. to about 45° C., and for a period from at least about one (1) minute to about eighteen (18) hours, preferably from about 1 to about 20 minutes, most preferably for about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody/human NGAL complex, the complex is then contacted with at least one detection antibody (under conditions which allow for the formation of a (first or multiple) capture antibody/human NGAL/second antibody detection complex). The at least one detection antibody can be the second, third, fourth, etc. antibodies used in the immunoassay. If the capture antibody/human NGAL complex is contacted with more than one detection antibody, then a (first or multiple) capture antibody/human NGAL/(multiple) detection antibody complex is formed. As with the capture antibody (e.g., the first capture antibody), when the at least second (and subsequent) detection antibody is brought into contact with the capture antibody/human NGAL complex, a period of incubation under conditions similar to those described above is required for the formation of the (first or multiple) capture antibody/human NGAL/(second or multiple) detection antibody complex. Preferably, at least one detection antibody contains a detectable label. The detectable label can be bound to the at least one detection antibody (e.g., the second detection antibody) prior to, simultaneously with or after the formation of the (first or multiple) capture antibody/human NGAL/(second or multiple) detection antibody complex. Any detectable label known in the art can be used. For example, the detectable label can be a radioactive label, such as, $^3H$, $^{125}I$, $^{35}S$, $^{14}C$, $^{32}P$, $^{33}P$, an enzymatic label, such as horseradish peroxidase, alkaline phosphatase, glucose 6-phosphate dehydrogenase, etc., a chemiluminescent label, such as, acridinium esters, luminal, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label can be bound to the antibodies either directly or through a coupling agent. An example of a coupling agent that can be used is EDAC (1-ethyl-3-(3-dimethylaminopropyl)carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The (first or multiple) capture antibody/human NGAL/(second or multiple) detection antibody complex can be, but does not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the at least first capture antibody is bound to a solid support it can be simultaneously contacted with the human NGAL-containing sample and the at least one second detection antibody to form a first (multiple) antibody/human NGAL/second (multiple) antibody complex, followed by removal of the fluid (test sample) from contact with the solid support. If the at least one first capture antibody is not bound to a solid support, then the (first or multiple) capture antibody/human NGAL/(second or multiple) detection antibody complex does not have to be removed from the test sample for quantification of the amount of the label.

After formation of the labeled capture antibody/human NGAL/detection antibody complex (e.g., the first capture antibody/human NGAL/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of human NGAL or human NGAL fragment in the test sample is determined by use of a standard curve that has been generated using serial dilutions of human NGAL or human NGAL fragment of known concentration. Other than using serial dilutions of human NGAL or human NGAL fragment, the standard curve can be generated gravimetrically, by mass spectroscopy and by other techniques known in the art.

The methods described herein (namely, the immunoassays and kits) can be used to evaluate the renal tubular cell injury status of a subject based on the determination of the level of NGAL present in the test sample. The subject to be evaluated can either currently have renal tubular cell injury or be at risk of developing renal tubular cell injury.

The methods described herein can be carried out on a subject after treatment of a subject for renal tubular cell injury or while the subject is currently experiencing renal tubular cell injury.

The methods described herein can be used to monitor the nephrotoxic side effects of drugs or other therapeutic agents in a subject.

The methods described herein can be carried out or performed after an event experienced by a subject, such as after a surgical procedure (such as after cardiac surgery, coronary bypass surgery, cardiovascular surgery, vascular surgery or kidney transplantation), after the subject has experienced a diminished blood supply to the kidneys, if the subject has or is experiencing a medical condition selected from the group consisting of: impaired heart function, stroke, trauma, sepsis and dehydration, admittance of a subject to an intensive care unit, after administration to the subject of one or more pharmaceuticals, or after administration to the subject of one or more contrast agents.

It goes without saying that while certain embodiments herein are advantageous when employed to assess renal tubular cell injury status, the immunoassays and kits also optionally can be employed to assess NGAL in other diseases, e.g., cancer, sepsis, and any disease disorder or condition involving assessment of NGAL.

More specifically, in addition to assessment of renal disorders, diseases and injuries (see, e.g., U.S. Pat. App. Pub. Nos. 2008/0090304, 2008/0014644, 2008/0014604, 2007/0254370, and 2007/0037232), the assay and assay components as described herein optionally can also be employed in any other NGAL assay or in any other circumstance in which an assessment of NGAL levels or concentration might prove helpful: e.g., cancer-related assays (e.g., generally, or more specifically including but not limited to pancreatic cancer, breast cancer, ovarian/uterine cancer, leukemia, colon cancer, and brain cancer; see, e.g., U.S. Pat. App. Pub. No. 2007/0196876; see, also, U.S. Pat. Nos. 5,627,034 and 5,846,739); diagnosis of systemic inflammatory response syndrome (SIRS), sepsis, severe sepsis, septic shock and multiple organ dysfunction syndrome (MODS) (see, e.g., U.S. Pat. App. Pub. Nos. 2008/0050832 and 2007/0092911; see, also, U.S. Pat. No. 6,136,526); hematology applications (e.g., estimation of cell type); assessment of preeclampsia, obesity (metabolic syndrome), insulin resistance, hyperglycemia, tissue remodeling (when complexed with MMP-9; see, e.g., U.S. Pat. App. Pub. No. 2007/0105166 and U.S. Pat. No. 7,153,660), autoimmune diseases (e.g., rheumatoid arthritis, inflammatory bowel disease, multiple sclerosis), irritable bowel syndrome (see, e.g., U.S. Pat. App. Pub. Nos. 2008/0166719 and 2008/0085524), neurodegenerative disease, respiratory tract disease, inflammation, infection, periodontal disease (see, e.g., U.S. Pat. No. 5,866,432), and cardiovascular disease including venous thromboembolic disease (see, e.g., U.S. Pat. App. Pub. Nos. 2007/0269836), among others.

G. NGAL IMMUNOASSAY KITS

The present invention also contemplates kits for detecting the presence of mammalian NGAL antigen in a test sample. Such kits can comprise one or more of the immunodiagnostic reagents (e.g., antibodies) described herein. More specifically, if the kit is a kit for performing an immunoassay, the kit optionally can comprise the immunodiagnostic reagent described herein, and instructions. A variety of immunoassay kits, e.g., including the immunodiagnostic reagent and antibodies described herein, are set forth in U.S. Provisional Application Ser. No. 60/981,473 filed Oct. 19, 2007 (incorporated by reference for its teachings regarding such assays).

Thus, the present invention further provides for diagnostic and quality control kits comprising one or more recombinant antibodies or mammalian NGAL of the invention. Optionally the assays, kits and kit components of the invention are optimized for use on commercial platforms (e.g., immunoassays on the Prism®, AxSYM®, ARCHITECT® and EIA (Bead) platforms of Abbott Laboratories, Abbott Park, Ill., as well as other commercial and/or in vitro diagnostic assays). Additionally, the assays, kits and kit components can be employed in other formats, for example, on electrochemical or other hand-held or point-of-care assay systems. The present invention is, for example, applicable to the commercial Abbott Point of Care (i-STAT®, Abbott Laboratories, Abbott Park, Ill.) electrochemical immunoassay system that performs sandwich immunoassays for several cardiac markers, including TnI, CKMB and BNP. Immunosensors and methods of operating them in single-use test devices are described, for example, in US Patent Applications 20030170881, 20040018577, 20050054078 and 20060160164 which are incorporated herein by reference. Additional background on the manufacture of electrochemical and other types of immunosensors is found in U.S. Pat. No. 5,063,081 which is also incorporated by reference for its teachings regarding same.

Optionally the kits include quality control reagents (e.g., sensitivity panels, calibrators, and positive controls). Preparation of quality control reagents is well known in the art, and is described, e.g., on a variety of immunodiagnostic product insert sheets. NGAL sensitivity panel members optionally can be prepared in varying amounts containing, e.g., known quantities of NGAL antibody ranging from "low" to "high", e.g., by spiking known quantities of the NGAL antibodies according to the invention into an appropriate assay buffer (e.g., a phosphate buffer). These sensitivity panel members optionally are used to establish assay performance characteristics, and further optionally are useful indicators of the integrity of the immunoassay kit reagents, and the standardization of assays.

In another embodiment, the present invention provides for a quality control kit comprising one or more antibodies of the present invention for use as a sensitivity panel to evaluate assay performance characteristics and/or to quantitate and monitor the integrity of the antigen(s) used in the assay.

The antibodies provided in the kit can incorporate a detectable label, such as a fluorophore, radioactive moiety, enzyme, biotin/avidin label, chromophore, chemiluminescent label, or the like, or the kit may include reagents for labeling the antibodies or reagents for detecting the antibodies (e.g., detection antibodies) and/or for labeling the antigens or reagents for detecting the antigen. The antibodies, calibrators and/or controls can be provided in separate containers or pre-dispensed into an appropriate assay format, for example, into microtiter plates.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The kit further can optionally include instructions for use, which may be provided in paper form or in computer-readable form, such as a disc, CD, DVD or the like.

By way of example, and not of limitation, examples of the present invention shall now be given.

H. ADAPTATION OF ASSAY KIT

The kit (or components thereof), as well as the method of determining the concentration of NGAL antigen in a test sample by an assay using the components and methods described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., NGAL capture antibody) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours) an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an NGAL assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the second detection antibody labeled with alkaline phosphatase (or other label). Within the fluid pouch of the cartridge is an aqueous reagent that includes p-aminophenol phosphate.

In operation, a sample suspected of containing NGAL antigen is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between NGAL antigen, NGAL capture antibody, and the labeled detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of NGAL antigen in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent.

Example 1

Development of NGAL Murine Cell Lines

All wild-type NGAL recombinant antigen (rAg) and mutant C87S NGAL NGAL rAg clones, subclones, hybrids, and hybridomas (including names and numbering), vectors, and vector constructs not specifically described herein are described in their entirety in U.S. Provisional Application Ser. No. 60/981,470 filed Oct. 19, 2007 (incorporated by reference for its teachings regarding same). For ease of reference, certain of these materials, or illustrative depictions from U.S. Provisional Application Ser. No. 60/981,470 are also included herein. Specifically: FIG. 1 (which shows the human NGAL wild-type antigen sequence (SEQ ID NO:1); FIG. 2 (which shows plasmid pJV-NGAL-A3 (also known as pJV-NGAL-hisA) containing the wild-type human NGAL sequence as described in Example 1 of U.S. Provisional Application Ser. No. 60/981,470; FIG. 3 (which shows the human NGAL C87S mutant antigen sequences (SEQ ID NO:2)); FIG. 4 (which shows the wild-type human NGAL polynucleotide sequence (SEQ ID NO:3)) and FIG. 5 (which shows the mutant human NGAL polynucleotide sequence (SEQ ID NO:4)).

Certain of these materials in U.S. Provisional Application Ser. No. 60/981,470, as well as further commercially available polypeptides were employed in the creation and/or assessment of particular cell lines, as further described herein. In particular, two mouse strains and one rabbit strain were used in an animal immunogenicity trial to stimulate an immune response to human Neutrophil Gelatinase Associated Lipocalin (NGAL), namely, CAF1/J mice, RBF/DnJ mice (The Jackson Laboratory, Bar Harbor, Me.) and NZW rabbits (Covance, Kalamazoo, Mich.). The four NGAL antigens immunized into animals were: (1) recombinant human NGAL produced from NSO myeloma cells (R&D Systems (Minneapolis, Minn.)); (2) recombinant human NGAL produced in HEK293 cells (transient expression system, work done at Abbott Laboratories); (3) native mammalian-derived human NGAL isolated from human leukocytes (Diagnostics Development (Uppsala, Sweden)); and (4) recombinant NGAL produced in E. coli (ProSpec-Tany TechnoGene (Rehovot, Israel)).

Mice were given 5 bi-weekly immunizations of 5 µg NGAL, alternating between Freund's Adjuvant (Difco, Detroit, Mich.) and Ribi Adjuvant (Corixa, Hamilton, Mont.). Sera samples were taken 9-14 days following the fifth immunization for evaluation in the EIA described below. The rabbits were used in an adjuvant study and given five monthly immunizations with 20 µg of NGAL using one of four adjuvant regimens: (1) Adjulite Freund's Adjuvant (Pacific Immunology Ramona, Calif.); (2) Alhydrogel Aluminum hydroxide gel adjuvant (Accurate Chemical, Westbury, N.Y.) in combination with oligodeoxynucleotides containing unmethylated CpG nucleotides (CpG-ODN, Cell Sciences, Canton, Mass.); (3) Difco Freund's adjuvant alternating with Ribi adjuvant; and (4) Difco Freund's adjuvant alternating with Quil A (Brenntag Biosector, Denmark) supplemented with CpG-ODN.

Sheep anti-mouse IgG Fc (Jackson Immunoresearch, West Grove Pa.) or Sheep anti-rabbit IgG Fc (Jackson Immunoresearch, West Grove, Pa.) were coated on 96-well microtiter EIA plates (Nunc Corporation, Rochester N.Y.) at 5 µg/mL. After the capture reagent was coated on the solid phase, it was removed and any unoccupied binding sites remaining on the plates were blocked using a 2% BSA solution in PBS (block solution). The plates were washed and log 3 serial dilutions of control antibodies and animal sera samples were added for a one-hour incubation. The plates were washed in distilled water and log 4 serial dilutions of NGAL antigen, diluted in block solution, starting at 1.0 µg/mL were added to the plate and allowed to incubate for 10 minutes. The antigen was washed from the plate with distilled water, and biotin-labeled goat anti-NGAL polyclonal antibody (R&D Systems, Minneapolis Minn.) diluted to 100 ng/mL in block solution was added and allowed to incubate for 30 minutes. Following this incubation, the antigen was washed from the plates using distilled water. Streptavidin-HRPO (Jackson Immunoresearch, West Grove, Pa.) was diluted to approximately 200 ng/mL in block solution and added to the plates and allowed to incubate for 30 minutes. The plates were washed with distilled water and 0.05% Tween 20 and o-phenylenediamine substrate (OPD; Abbott Laboratories, Abbott Park, Ill.) was used as the chromogen to generate signal. Plates were read at 492 nm and the results analyzed by plotting using Kaleida Graph software (Synergy Software, Reading, Pa.), formula provided below:

$$y = m1 + m2 * m0/(m3 + m0)$$

Where m1 is background signal, m2 is maximum signal, m0 is variable antigen concentration, y is signal (i.e. optical density) and m3 is the antigen concentration at 50% of maximal binding. Sera samples were ranked relative to each other based on their overall anti-NGAL titer, and based on the $Ag_{50}$ which is the value generated at 50% of maximal binding signal, thus translating into the highest affinity. This testing was performed similar to that detailed in Friguet et al., J. Immunolog. Methods, 1985, 77:305-319.

Sera samples were ranked relative to each other based on their overall anti-NGAL titer, and based on which generated 50% of maximal binding signal with the lowest antigen concentration, thus translating into the highest affinity. Testing was done similar to that detailed in Friguet et al., J. Immunolog. Methods, 77, 305-319 (1985). Results are presented in Tables 1A, 1B and 1C.

TABLE 1A

| Antigen Source | Host | CAF1/J mice Average titer | CAF1/J mice Average $Ag_{50}$ (ng/mL) | CAF1/J mice $Ag_{50}$ range (ng/mL) |
|---|---|---|---|---|
| R&D Systems | NSO myeloma | 1:42,120 | 23 | 9-45 |
| Abbott Laboratories | HEK293 | 1:35,200 | 21 | 1-43 |
| Diagnostics Development | Human leukocytes | 1:44,000 | 23 | 15-29 |
| ProSpec-Tany | E. coli | 1:72,900 | 24 | 6-37 |

TABLE 1B

| Antigen Source | Host | RBF/DnJ mice Average titer | RBF/DnJ mice Average Ag$_{50}$ (ng/mL) | RBF/DnJ mice Ag$_{50}$ range (ng/mL) |
|---|---|---|---|---|
| R&D Systems | NSO myeloma | 1:1,487 | 44 | 22-70 |
| Abbott Laboratories | HEK293 | 1:5,850 | 84 | 46-137 |
| Diagnostics Development | Human leukocytes | 1:12,444 | 69 | 27-121 |
| ProSpec-Tany | E. coli | 1:170,100 | 93 | 32-185 |

TABLE 1C

| Antigen Source | Host/ Adjuvant | NZW rabbits Average titer | NZW rabbits Average Ag$_{50}$ (ng/mL) | NZW rabbits Ag$_{50}$ range (ng/mL) |
|---|---|---|---|---|
| Abbott Laboratories | HEK293 Adjulite Freund's | 1:906,332 | 8 | 6-9 |
| Abbott Laboratories | HEK293 Aluminum hydroxide/ CpG-ODN | 1:338,749 | 13 | 8-18 |
| Abbott Laboratories | HEK293 Difco Freund's/ Ribi | 1:200,384 | 16 | 10-19 |
| Abbott Laboratories | HEK293 Difco Freund's/ Quil A | 1:300,245 | 19 | 15-22 |

The EIA results obtained from mice sera in Tables 1A and 1B clearly indicated that the CAF1/j mice demonstrated a much higher titer and improved relative affinity (Ag$_{50}$) to the NGAL antigen. The CAF1/j mice demonstrated a stronger and more highly specific immune response to the mammalian-produced and glycosylated antigen than did the RBF/Dnj mice. This is possibly due to the role of major histocompatibility complex (MHC) presentation of antigen to the mouse immune system as described by Rudd et al., Science, 291: 2370-2376 (2001). It appears that the CAF1/j strain of mouse was genetically better equipped than the RBF/Dnj mice to process the glycosylated antigen and mount a more efficient immune response.

Results in Table 1C obtained from the rabbit sera samples indicate that those immunized with HEK293-expressed recombinant NGAL using Adjulite Freund's adjuvant yielded a statistically higher antibody titer than rabbits using the remaining three adjuvant regimens. Additionally, the rabbits immunized using Adjulite Freund's adjuvant yielded improved relative affinity. These animals were statistically similar to those immunized using Aluminum Hydroxide in combination with CpG-ODN. While rabbit B cells could have been used to generate anti-NGAL secreting hybridoma cell lines (Spieker-Polet et al., Proc. Natl. Acad. Sci. 92, 9348-9352 (1995)), the assay sensitivity requirements were met using mouse hybridoma cell lines.

After successfully demonstrating the highest titer and affinity to NGAL antigen, CAF1/J mice numbers 13, 14 and 20 were allowed to rest for seven weeks prior to pre-fusion boost of antigen. Three days prior to fusion, the mice were anesthetized and an incision was made in order to open the body cavity and expose the spleen. Each mouse was given a 10 µg injection of recombinant human NGAL antigen (R&D Systems, Minneapolis, Minn.) diluted in 0.9% saline solution directly into the spleen, and an additional 10 µg into the body cavity around the spleen. The incisions were closed using surgical staples and the mice were rested before fusion.

On the day of fusion, the mice were euthanized and their spleens containing anti-NGAL splenocytes were harvested and placed into Hybridoma Serum Free Medium (HSFM) (Invitrogen Corp., Carlsbad, Calif.). A cell fusion was performed as described by Kohler and Milstein, Nature, 2 56:495-7 (1975). Each mouse spleen was placed into a separate petri dish containing HSFM. The splenocytes were perfused out of each spleen using a syringe containing HSFM and a cell scraper, then counted using a hemocytometer. Approximately $1.7 \times 10^7$ splenocytes were pooled from each mouse and washed by centrifugation into a cell pellet and re-suspended in HSFM. These splenocytes were mixed with an equal number of SP 2/0 myeloma cells and centrifuged into a pellet. The fusion was accomplished by exposing the splenocytes and SP 2/0 cells to 50% polyethylene glycol (PEG) (Molecular Weight 1300-1600, ATCC, Manassas Va.) in HSFM. One mL of the PEG solution was added to the cell pellet over 30 seconds, followed by an additional one-minute incubation. The PEG and cell pellet were diluted by slowly adding thirty (30) mL of HSFM over 30 seconds. The fused cells were then removed from suspension by centrifugation and the supernatant decanted. The cell pellet was re-suspended into 428 mL of HSFM supplemented with 15% FBS (Hyclone Laboratories, Logan Utah), HAT (Hypoxanthine, Aminopterin, Thymidine) (Sigma Laboratories, St. Louis, Mo.), HT Supplement (Invitrogen Corp., Carlsbad, Calif.), Hybridoma Cloning Factor (Bioveris Corporation, Gaithersburg Md.), and L-Glutamine (Invitrogen Corp., Grand Island, N.Y.) in order to select for hybridomas. The cells were plated at 0.2 mL per well into twenty-four 96-well cell culture plates. At days 5, 7, 11 and 12, one half of the medium in each well was removed by aspiration and replaced with HSFM supplemented with 15% FBS, HT Supplement, and L-glutamine. Hybridomas were allowed to grow for 10 or 13 days prior to supernatant screening for antibody production.

Cell supernatant samples were analyzed for anti-NGAL antibodies by EIA. Either rabbit anti-mouse IgG Fc or sheep anti-mouse IgG Fc (Jackson Immunoresearch, West Grove, Pa.) was coated on 96-well microtiter EIA plates at 5 µg/mL. After the capture reagent has been coated on the solid phase, it was removed and any open binding sites on the plates were blocked using block solution. Cell supernatants were then added to the blocked plates and allowed to incubate at room temperature for at least one hour. The anti-mouse IgG Fc captures the anti-NGAL mouse antibody from the supernatant. Following the incubation, the supernatants were washed off using distilled water. NGAL antigen, which has been labeled with biotin, was added to the plates at 100-200 ng/mL and incubated for 30 minutes. Following this incubation, the antigen was washed from the plates using distilled water. Streptavidin-HRPO (Jackson Immunoresearch) was diluted to approximately 200 ng/mL in block solution and added to the plates and allowed to incubate for 30 minutes. The plates were washed with distilled water to remove the NGAL-biotin, and o-phenylenediamine substrate (OPD; Abbott Laboratories, Abbott Park, Ill.) was used as the chromogen to generate signal. Plates were read at 492 nm and the results were analyzed. Hybrids were considered positive if they had an EIA signal at least 3 times greater than background (See Table 2, below).

TABLE 2

| Hybrid No. | Background | CAF1 #14 sera @ 1:10,000 | Hybrid |
|---|---|---|---|
| 1-903 | 0.25 | 1.71 | 1.76 |
| 1-2322 | 0.08 | 1.73 | 2.50 |

Positive hybrids were expanded to 24-well plates in HSFM supplemented with 10% FBS and HT supplement. Following 3-7 days growth, the 24-well cultures were evaluated by EIA as described above, except that multiple concentrations of the biotin labeled NGAL were used to provide a relative affinity ranking (See, Tables 3 and 4, below). Hybrids that demonstrated a relatively high affinity to NGAL in this assay were expanded to culture flasks for additional evaluation using the BIAcore instrument (BIAcore International AB, Uppsala, Sweden).

TABLE 3

| Sample No. | 0 ng/mL | 50 ng/mL | 500 ng/mL |
|---|---|---|---|
| NC | 0.07 | 0.06 | 0.09 |
| AntibodyShop HYB 211-01 | 0.05 | 0.88 | 1.56 |
| AntibodyShop HYB 211-02 | 0.05 | 0.64 | 1.42 |
| AntibodyShop HYB 211-05 | 0.07 | 0.29 | 1.67 |
| 1-2322 | 0.07 | 1.47 | 1.82 |

TABLE 4

| Sample No. | 0 ng/mL | 25 ng/mL | 250 ng/mL |
|---|---|---|---|
| AntibodyShop HYB 211-01 | 0.05 | 0.68 | 1.54 |
| 1-903 | 0.05 | 0.76 | 2.01 |

Using BIAcore, NGAL hybrid supernatants are evaluated for relative binding affinity to NGAL and grouped accordingly in NGAL binding epitope groups. The affinity assay was completed on a goat anti-mouse IgG Fc Capture Biosensor as follows. Flow cells were first equilibrated with a running buffer (hereinafter "Running Buffer") that contains HBS-EP buffer spiked with 0.1% BSA and 0.1% CM-Dextran), at 10 µL/min. Next, 13 µL of supernatant was floated across individual flow cells capturing anti-NGAL antibody from the supernatant onto the biosensor, and with one flow cell being left blank as a reference flow cell. The flow cells then were washed for 5 minutes at 50 µL/min with Running Buffer, and 150 µL of NGAL antigen at a 100 nM concentration was injected across the chip followed by 5 minutes of Running Buffer. The relative binding kinetics, association and dissociation, were monitored via sensorgrams. The sensorgrams were analyzed using Scrubber 2.0 software (BioLogic Software Pty Ltd., Australia) to determine association and dissociation rates, as well as overall $K_D$. The results are shown in Table 5, below.

TABLE 5

| NGAL mAb | Epitope Group | k(on) ($M^{-1}s^{-1}$) | k(off) ($s^{-1}$) | $K_D$ (M) |
|---|---|---|---|---|
| NGAL 1-2322 | 1 | $4.68 \times 10^5$ | $7.28 \times 10^{-5}$ | $1.55 \times 10^{-10}$ |
| NGAL 1-181 | 1 | $4.67 \times 10^5$ | $8.49 \times 10^{-5}$ | $1.82 \times 10^{-10}$ |
| NGAL 1-680 | 1 | $3.81 \times 10^5$ | $8.54 \times 10^{-5}$ | $2.24 \times 10^{-10}$ |
| NGAL 1-192 | 1 | $4.58 \times 10^5$ | $1.07 \times 10^{-4}$ | $2.34 \times 10^{-10}$ |
| NGAL 1-1886 | 1 | $3.82 \times 10^5$ | $1.21 \times 10^{-4}$ | $3.17 \times 10^{-10}$ |
| NGAL 1-821 | 1 | $5.09 \times 10^5$ | $1.74 \times 10^{-4}$ | $3.42 \times 10^{-10}$ |
| NGAL 1-809 | 1 | $6.22 \times 10^5$ | $2.23 \times 10^{-4}$ | $3.58 \times 10^{-10}$ |
| HYB 211-01 | 1 | $\mathbf{2.00 \times 10^6}$ | $\mathbf{1.60 \times 10^{-3}}$ | $\mathbf{8.00 \times 10^{-10}}$ |
| NGAL 1-1944 | 1 | $3.18 \times 10^5$ | $2.82 \times 10^{-4}$ | $8.86 \times 10^{-10}$ |
| NGAL 1-2194 | 1 | $4.30 \times 10^5$ | $5.50 \times 10^{-4}$ | $1.28 \times 10^{-9}$ |
| NGAL 1-1952 | 1 | $2.08 \times 10^5$ | $3.69 \times 10^{-4}$ | $1.77 \times 10^{-9}$ |
| NGAL 1-2415 | 1 | $2.97 \times 10^5$ | $1.04 \times 10^{-3}$ | $3.49 \times 10^{-9}$ |
| NGAL 1-2315 | 1 | $2.13 \times 10^5$ | $1.06 \times 10^{-3}$ | $4.96 \times 10^{-9}$ |
| NGAL 1-1191 | 1 | $3.14 \times 10^5$ | $1.56 \times 10^{-3}$ | $4.97 \times 10^{-9}$ |
| NGAL 1-714 | 1 | $1.68 \times 10^5$ | $9.12 \times 10^{-4}$ | $5.42 \times 10^{-9}$ |
| NGAL 1-1672 | 1 | $2.37 \times 10^5$ | $1.41 \times 10^{-3}$ | $5.96 \times 10^{-9}$ |
| NGAL 1-2374 | 1 | $4.50 \times 10^5$ | 0.00271 | $6.02 \times 10^{-9}$ |
| NGAL 1-916 | 1 | $1.98 \times 10^5$ | $1.47 \times 10^{-3}$ | $7.42 \times 10^{-9}$ |
| NGAL 1-1638 | 1 | $1.68 \times 10^5$ | $1.31 \times 10^{-3}$ | $7.81 \times 10^{-9}$ |
| NGAL 1-904 | 1 | $1.44 \times 10^5$ | 0.01241 | $8.64 \times 10^{-9}$ |
| NGAL 1-362 | 1 | $2.28 \times 10^5$ | $2.04 \times 10^{-3}$ | $8.96 \times 10^{-9}$ |
| NGAL 1-2045 | 1 | $1.43 \times 10^5$ | $1.97 \times 10^{-3}$ | $1.38 \times 10^{-8}$ |
| NGAL 1-269 | 1 | $4.08 \times 10^5$ | $5.87 \times 10^{-3}$ | $1.44 \times 10^{-8}$ |
| NGAL 1-986 | 2 | $2.91 \times 10^5$ | $2.44 \times 10^{-4}$ | $8.40 \times 10^{-10}$ |
| NGAL 1-902 | 2 | $2.90 \times 10^5$ | $2.68 \times 10^{-4}$ | $9.23 \times 10^{-10}$ |
| NGAL 1-903 | 2 | $2.69 \times 10^5$ | $2.72 \times 10^{-4}$ | $1.01 \times 10^{-9}$ |
| NGAL 1-1026 | 2 | $2.73 \times 10^5$ | $2.76 \times 10^{-4}$ | $1.01 \times 10^{-9}$ |
| HYB 211-02 | 2 | $\mathbf{1.10 \times 10^5}$ | $\mathbf{1.30 \times 10^{-4}}$ | $\mathbf{1.18 \times 10^{-9}}$ |
| NGAL 1-2357 | 2 | $2.03 \times 10^5$ | $2.80 \times 10^{-4}$ | $1.38 \times 10^{-9}$ |
| NGAL 1-2190 | 2 | $7.22 \times 10^5$ | $1.10 \times 10^{-3}$ | $1.52 \times 10^{-9}$ |
| NGAL 1-205 | 2 | $3.92 \times 10^5$ | $6.71 \times 10^{-4}$ | $1.71 \times 10^{-9}$ |
| NGAL 1-174 | 2 | $6.16 \times 10^5$ | $1.51 \times 10^{-3}$ | $2.45 \times 10^{-9}$ |
| NGAL 1-2080 | 2 | $1.28 \times 10^5$ | $6.35 \times 10^{-4}$ | $4.96 \times 10^{-9}$ |
| NGAL 1-2092 | 2 | $1.21 \times 10^5$ | $6.29 \times 10^{-4}$ | $5.20 \times 10^{-9}$ |
| NGAL 1-1826 | 2 | $3.00 \times 10^5$ | $6.33 \times 10^{-3}$ | $2.11 \times 10^{-8}$ |
| NGAL 1-1732 | 3 | $2.35 \times 10^5$ | $1.77 \times 10^{-4}$ | $7.51 \times 10^{-10}$ |
| NGAL 1-1427 | 3 | $1.71 \times 10^5$ | $1.37 \times 10^{-4}$ | $8.02 \times 10^{-10}$ |
| NGAL 1-281 | 3 | $2.63 \times 10^5$ | $2.76 \times 10^{-4}$ | $1.05 \times 10^{-9}$ |
| NGAL 1-2302 | 3 | $2.71 \times 10^5$ | $2.99 \times 10^{-4}$ | $1.10 \times 10^{-9}$ |
| NGAL 1-2314 | 3 | $2.86 \times 10^5$ | $3.15 \times 10^{-4}$ | $1.10 \times 10^{-9}$ |
| NGAL 1-1090 | 3 | $2.72 \times 10^5$ | $3.20 \times 10^{-4}$ | $1.18 \times 10^{-9}$ |
| NGAL 1-1034 | 3 | $1.94 \times 10^5$ | $3.87 \times 10^{-4}$ | $1.99 \times 10^{-9}$ |
| NGAL 1-1136 | 3 | $1.94 \times 10^5$ | $4.24 \times 10^{-4}$ | $2.18 \times 10^{-9}$ |
| NGAL 1-1148 | 3 | $1.88 \times 10^5$ | $4.18 \times 10^{-4}$ | $2.22 \times 10^{-9}$ |
| NGAL 1-505 | 3 | $4.25 \times 10^5$ | $1.03 \times 10^{-3}$ | $2.42 \times 10^{-9}$ |
| NGAL 1-141 | 3 | $1.09 \times 10^6$ | 0.00265 | $2.43 \times 10^{-9}$ |
| NGAL 1-831 | 3 | $2.25 \times 10^5$ | $8.86 \times 10^{-4}$ | $3.94 \times 10^{-9}$ |
| NGAL 1-652 | 3 | $2.47 \times 10^5$ | $9.94 \times 10^{-4}$ | $4.03 \times 10^{-9}$ |
| NGAL 1-936 | 3 | $2.13 \times 10^5$ | $8.91 \times 10^{-4}$ | $4.19 \times 10^{-9}$ |
| NGAL 1-1552 | 3 | $1.43 \times 10^6$ | $6.04 \times 10^{-3}$ | $4.24 \times 10^{-9}$ |
| NGAL 1-280 | 3 | $2.52 \times 10^5$ | $1.21 \times 10^{-3}$ | $4.81 \times 10^{-9}$ |
| NGAL 1-289 | 3 | $1.96 \times 10^5$ | $9.63 \times 10^{-4}$ | $4.91 \times 10^{-9}$ |
| NGAL 1-406 | 3 | $3.15 \times 10^6$ | 0.01712 | $5.43 \times 10^{-9}$ |
| NGAL 1-1947 | 3 | $1.15 \times 10^5$ | $6.69 \times 10^{-4}$ | $5.84 \times 10^{-9}$ |
| NGAL 1-2389 | 3 | $1.59 \times 10^5$ | $1.06 \times 10^{-3}$ | $6.70 \times 10^{-9}$ |
| NGAL 1-2405 | 3 | $1.41 \times 10^5$ | $9.57 \times 10^{-4}$ | $6.77 \times 10^{-9}$ |
| NGAL 1-1959 | 3 | $1.99 \times 10^5$ | $1.41 \times 10^{-3}$ | $7.07 \times 10^{-9}$ |
| NGAL 1-438 | 3 | $1.83 \times 10^5$ | $1.29 \times 10^{-3}$ | $7.09 \times 10^{-9}$ |
| NGAL 1-277 | 3 | $1.35 \times 10^5$ | $1.09 \times 10^{-3}$ | $8.11 \times 10^{-9}$ |
| NGAL 1-469 | 3 | $1.30 \times 10^5$ | $1.09 \times 10^{-3}$ | $8.41 \times 10^{-9}$ |
| NGAL 1-1684 | 3 | $1.37 \times 10^5$ | $1.18 \times 10^{-3}$ | $8.57 \times 10^{-9}$ |
| NGAL 1-1118 | 3 | $3.99 \times 10^5$ | $3.91 \times 10^{-3}$ | $9.80 \times 10^{-9}$ |
| NGAL 1-1167 | 3 | $6.29 \times 10^5$ | $6.32 \times 10^{-3}$ | $1.01 \times 10^{-8}$ |
| NGAL 1-2444 | 3 | $2.32 \times 10^5$ | $2.64 \times 10^{-3}$ | $1.14 \times 10^{-8}$ |
| NGAL 1-1716 | 3 | $1.27 \times 10^5$ | $1.46 \times 10^{-3}$ | $1.15 \times 10^{-8}$ |
| NGAL 1-1733 | 3 | $4.66 \times 10^5$ | $6.09 \times 10^{-3}$ | $1.31 \times 10^{-8}$ |
| HYB 211-05 | 3 | $\mathbf{3.00 \times 10^4}$ | $\mathbf{7.80 \times 10^{-4}}$ | $\mathbf{2.60 \times 10^{-8}}$ |
| NGAL 1-419 | 3 | $3.15 \times 10^5$ | 0.01284 | $4.08 \times 10^{-8}$ |

NGAL binding epitope groups were determined by measuring the ability of each NGAL hybrid mAb to complete a mAb-antigen-mAb sandwich when NGAL is pre-complexed to one of three commercially available monoclonal antibodies known as HYB 211-01, HYB 211-02 or HYB 211-05 that are known to have different and distinct binding epitopes on NGAL. Briefly, using the same type of Fc capture biosensor and Running Buffer as in the affinity assay described above, the chip is equilibrated with Running Buffer at 5 µL/min for 2 minutes prior to loading 12 μL of each of the three outside vendor mAbs onto individual flow cells. One flow cell is left blank and is used as a reference. The flow cells are washed with Running Buffer for 2 minutes and then all empty Fc capture sites are blocked with 10 μL of a highly concentrated solution of mouse IgG. The chip is equilibrated for another 2 minutes prior to floating over 15 μL of either 1 μM NGAL or only Running Buffer. After one more 2 minute incubation, 15 μL of a NGAL hybrid supernatant is floated over the biosensor surface.

If the NGAL hybrid mAb creates a significant signal in the presence of NGAL compared to when only a Running Buffer was injected over the surface, then that NGAL hybrid mAb can form a mAb-antigen-mAb sandwich with the commercially available mAb. The NGAL hybrids were grouped into three different epitope groups based on their ability to form sandwiches with the external vendor mAbs. Successful sandwich formation of mAbs with NGAL is scored positive and considered as evidence of the compatibility of the paired mAbs binding to NGAL simultaneously. Each epitope group is capable of forming a sandwich with either of the two other groups, but not with members of its own group. (See, Table 6, below).

TABLE 6

| Epitope Group 1 | Epitope Group 2 | Epitope Group 3 |
|---|---|---|
| HYB 211-01 | HYB 211-02 | HYB 211-05 |
| 1-2322 | 1-903 | 1-419 |
| 1-181 | | |

The NGAL hybrids are relatively ranked based on the Biacore inhibition data and kinetic screening. Hybrids 1-903 and 1-2322 were selected for further evaluation because they bound to two distinctly different NGAL epitopes with improved relative affinity. These hybrids were selected for cloning to stabilize the cell line and ensure the absence of a mixed cell population.

Hybrid 1-903 was cloned by growing cells in semi-solid tissue culture medium and picking colonies for subculture with the ClonepixFL instrument (Genetix Ltd., Hampshire, UK). Briefly, the hybrid cell suspension was diluted into a 2× concentration of HSFM supplemented with 10% FBS and an equal volume of Clone Matrix methylcellulose medium (Genetix Ltd., Hampshire, UK). The semi-solid cell suspension was seeded into tissue culture plates and allowed to incubate for approximately 7 days at 37° C. At the time of cell plating, a 5 μg/mL solution of goat anti-mouse IgG-FITC solution (Clone Detect, Genetix Ltd., Hampshire, UK) was added to the semi-solid medium. A colony grown in a semi-solid medium is considered to be clonal because the single cell initiating it has not been allowed to move and mix with other cells. An immunoprecipitation reaction occurs between the antibody being produced by the colony and the goat anti-mouse IgG Fc-FITC which fluoresces. The brighter the fluorescence, the more antibody is being produced by the colony.

Figure 6:
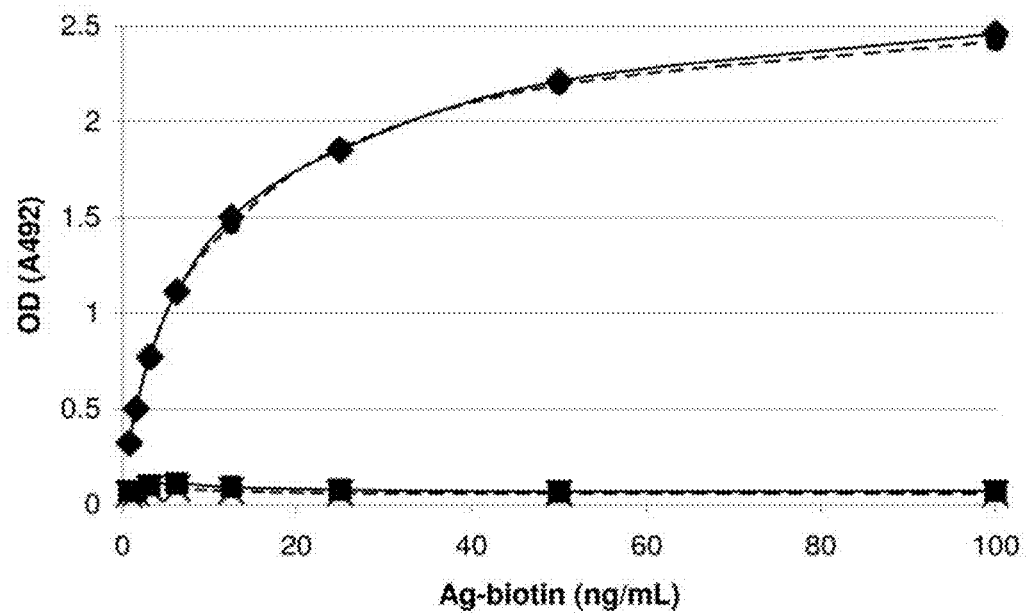
FIG. 6 is a graph that shows that purified antibody from subclone 1-903-430 demonstrates a similar dose response curve with biotin labeled human NGAL antigen (NGAL-Bt) when compared to parental mAb 1-903-102, thereby illustrating that the subcloning process did not alter the subclones' functional performance. Symbols: (-♦-) mAb 1-903-102 with NGAL-Bt; (-●-) mAb 1-903-430 with NGAL-Bt; (-■-) mAb 1-903-102 with irrelevant biotinylated antigen (NC Ag-Bt); (-x-) mAb 1-903-430 with NC Ag-Bt.

Colonies are analyzed for fluorescence on the ClonepixFL (See, FIG. 6) and the ones with the most intense signal were selected for automated transfer to 96-well tissue culture plates containing HSFM with 10% FBS. These plates were incubated for 7-10 days and clone supernatants were tested for anti-NGAL titer as previously described above. Clone 1-903-102 was selected for additional evaluation. This cell line was weaned to HSFM without FBS and subcloned using the semi-solid medium as described above. Cell line 1-903-430 also was selected for scale up and cell banking purposes. Liquid nitrogen freezers are used for long-term storage of the cell bank. In sum, anti-NGAL mAb hybrid 1-903-102 is the parental clone from which subclone 1-903-430 was derived.

Figure 7:
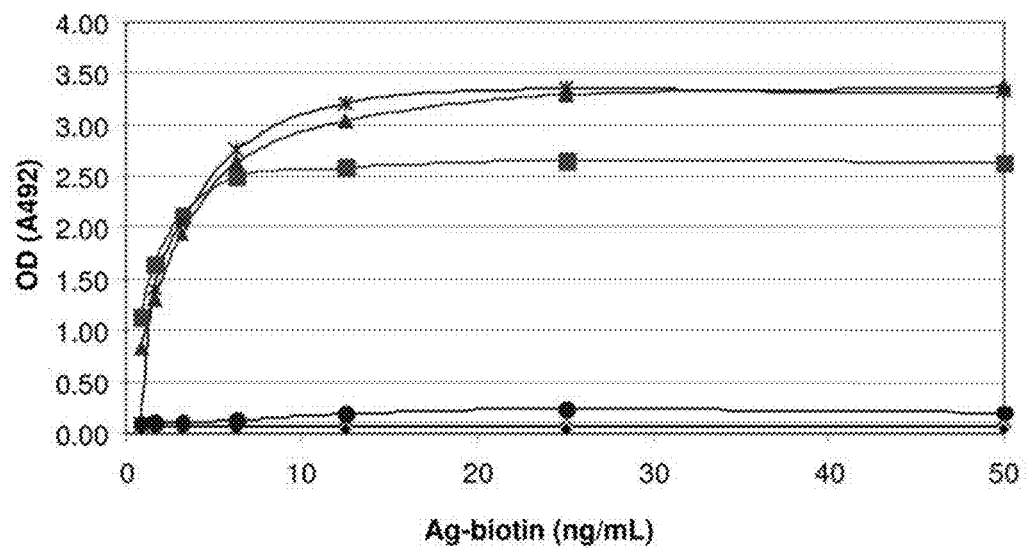
FIG. 7 shows the same dose response curve as in FIG. 6 comparing the parent and subclone material for the 1-2322 cell line except that in this figure a negative control mAb with a matching negative control biotin-labeled antigen (NC mAb) was included along with to demonstrate the absence of non-specific binding. Symbols: (-♦-) NC mAb with NGAL-Bt; (-●-) mAb 1-2322-455 with NC Ag-Bt; (-■-) NC mAb with NC Ag-Bt; (-▲-) mAb 1-2322-101 with NGAL-Bt; (-x-) mAb 1-2322-101 with NC Ag-Bt; (-*-) mAb 1-2322-455 with NGAL-Bt.

Hybrid 1-2322 was selected for cloning by limiting dilution. Briefly, hybrid cells were serially diluted in HSFM containing 10% FBS and seeded into 96-well tissue culture plates. These plates were incubated at 37° C. until confluent growth was apparent. Clone supernatants were tested (See, FIG. 7) for anti-NGAL titer as previously described above. Clone 1-2322-101 was selected for additional evaluation and weaned for growth in HSFM without FBS. This cell line was subcloned using the semi-solid medium as described above. Cell line 1-2322-455 was selected for scale up and cell banking purposes. Liquid nitrogen freezers are used for long-term storage of the cell bank. In sum, anti-NGAL mAb hybrid 1-2322-101 is the parental clone from which subclone 1-2322-455 was derived.

Example 2

Characterization of Antibodies

Purified antibody from each of the 1-903-430 and 1-2322-455 cell lines was tested with the Isostrip Mouse Monoclonal Antibody Isotyping Kit (Roche Diagnostics, Basel, Switzerland). An aliquot of 150 μL of 0.2 μg/mL for each sample was added to the development tube and mixed. An Isostrip was added to each tube and incubated for 5-10 minutes until color development on the strip's band. The results indicated that both the 1-903-430 and 1-2322-455 are mouse IgG1 subtype with kappa light chain.

Example 3

Antibody Production and Purification

The 1-903-430 and 1-2322-455 cell lines were expanded in HSFM and seeded into roller bottles at approximately $0.5 \times 10^{-5}$ cells/mL. The cultures were incubated at 37° C. while rotating at approximately 1 revolution per minute for 10-14 days, or until a terminal end culture was obtained. The terminal roller bottle supernatant was harvested and clarified with a 0.45 μM filter. The clarified supernatant was concentrated using a Pellicon system and filtered with a 0.45 μM filter. The mAb concentrate was diluted with an equal volume of 1.5 M glycine/3 N NaCl buffer at pH 8.9, then loaded onto a pre-equilibrated 5 ml Protein A column using the AKTA automated purification system (Amersham/Pharmacia). The column was then washed with 5 column volumes of binding buffer and when a stable baseline was achieved, the mAb was eluted with a pH 3.0 citrate buffer. The mAb was then transferred to a 70 mL G25 column for an exchange into PBS. The antibody was aliquoted and stored at −70° C.

Example 4

Antibody Binding Affinity

The equilibrium dissociation constants for both the anti-NGAL 1-2322-455 and the 1-903-430 mAb were determined using Kinetic Exclusion Assay (KinExA®), available from Sapidyne Instruments (Boise, Id.) (See, Darling and Brault, Assay and Drug Development Technologies, 2(6):647-657 (2004)). A constant amount of IgG antibody (1-2322-455 or 1-903-430) was incubated with various concentrations ($5 \times 10^{-8}$ M to $10^{-12}$ M) of human NGAL antigen and allowed to come to equilibrium (3-8 hours) before sampling. The amount of free binding sites was determined by injecting the antibody/human NGAL reaction mixture over human NGAL immobilized on solid-phase Polymethyl-methacrylate (PMMA) beads. The free anti-NGAL antibody bound to the human NGAL coated beads were subsequently detected using the fluorescent CY5-conjugated goat anti-mouse polyclonal antibody (GAM-Cy5). The degree of GAM-Cy5 bound was proportional to the amount of anti-NGAL IgG bound to the human NGAL-coated beads. The $K_D$ was determined by analyzing the amount of free binding sites versus the amount of antigen present in the reaction sample using software provided by the manufacturer (Sapidyne Instruments, Boise, Id.). Experiments were performed in a PBS, pH 7.4, and 1% BSA reaction diluent. The $K_D$ of the anti-NGAL 1-2322-455 IgG and 1-903-430 IgG for NGAL wild-type antigen and NGAL mutant C87S antigen are reported in Table 7 below.

TABLE 7

| | Wild-type NGAL rAg (CHO clone #662) | Mutant C87S NGAL rAg (CHO cell clone #734) |
|---|---|---|
| 1-903-430 | $3.2 \times 10^{-10}$ M | $1.1 \times 10^{-9}$ M |
| 1-2322-455 | $2.4 \times 10^{-11}$ M | $2.3 \times 10^{-11}$ M |

Affinity results measured by KinExA demonstrated that monoclonal antibody 1-2322-455 has the same affinity for both wild-type NGAL and mutant C87S NGAL. Monoclonal antibody 1-903-430 has higher affinity on wild-type NGAL antigen than that of the mutant C87S NGAL antigen.

Example 5

Purified Antibody Qualification

The purpose of this experiment was to test clones for their ability to form sandwiches in a chemiluminescent assay format. Goat anti-mouse IgG Fc was coated on a white 96 well micro-titer immunoassay plates at 2 µg/mL in PBS. After the capture reagent had been coated on the solid phase, it was removed and any open binding sites on the plates were blocked using a 2% Fish Gel in PBS solution. The block solution was then washed off and purified antibody from mAb 1-2322-101 was added at 1 µg/mL in PBS and allowed to incubate at room temperature for one hour. Following this incubation the plate was washed with water and NGAL rAg produced in CHO cells was added to the plate in log 2 serial dilutions from 0 to 100 ng/mL in PBS and allowed to incubate for one hour at room temperature. Following this incubation, the plates were washed with water and blocked again with a 1% normal mouse solution in Fish Gel block to occupy unbound goat anti-mouse IgG Fc capture antibodies, prior to adding the secondary mAb reagent. Following this block, the plates were washed and the acridinium-labeled secondary monoclonal reagents were added at 250-500 ng/mL in block solution. The secondary mAbs were incubated for 30 minutes at room temperature then washed with water. Assay signal was read on the Wallac Microbeta Jet Instrument (Perkin Elmer, Waltham Mass.) where Architect Pre-trigger Solution (Abbott No. 6E23-65) and Architect Trigger Solution (Abbott No. 6C55-60) are added and flash chemiluminescence is measured in luminescence counts per second (LCPS).

Figure 8:
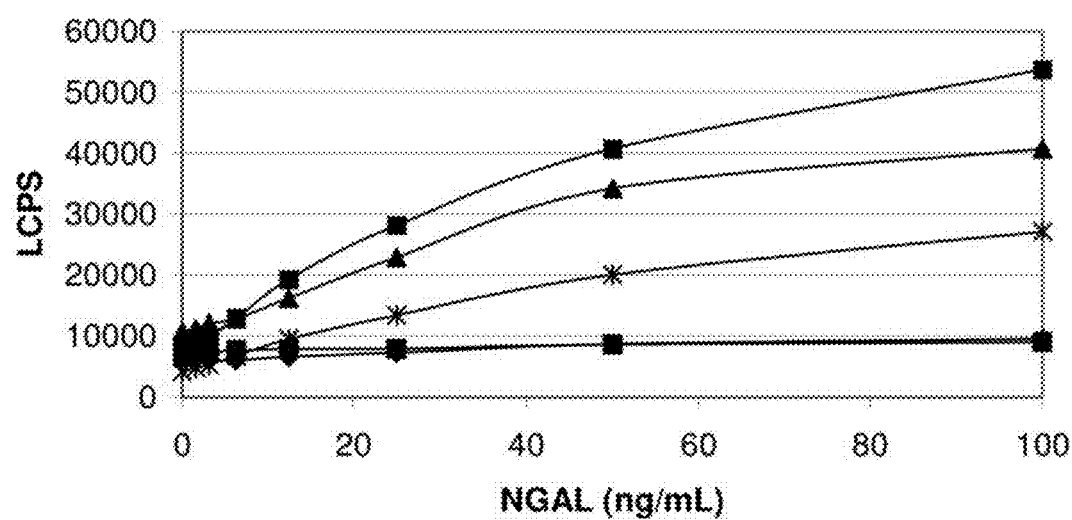
FIG. 8 is a graph of antigen titration curves for NGAL mAb CIA sandwich formation, with NGAL concentration (ng/mL) on the ordinate and luminescence counts per second (LCPS) on the abscissa. Symbols: (-♦-) acridinylated 211-01 mAb; (-■-) acridinylated 1-181-128 mAb; (-▲-) acridinylated 1-419-182 mAb; (-x-) acridinylated 1-903-102 mAb; (-*-) acridinylated 211-02 mAb.
Figure 11:
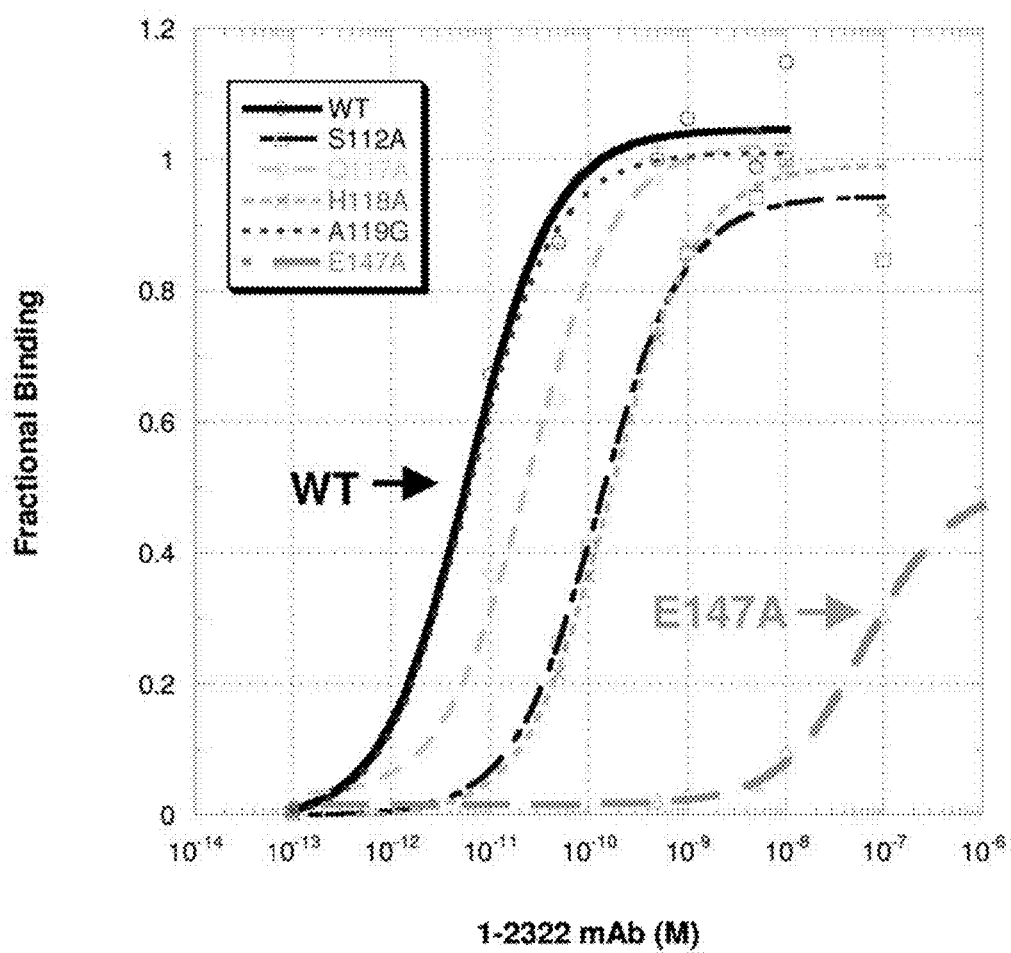
FIG. 11 is an isotherm binding data graph for monoclonal antibody 1-2322-455 binding to different functional epitopes as described in Example 7. Symbols: (-○-, solid line) wild-type NGAL epitope; (-□-, solid line) NGAL epitope comprising S112A mutation; (-◇-, long dashes line) NGAL epitope comprising Q117A mutation; (-x-, short dashes line) NGAL epitope comprising H118A mutation; (-+-, dotted line) NGAL epitope comprising A118G mutation; (-Δ-, extra long dashes line) NGAL epitope comprising E147A mutation.
Figure 12:
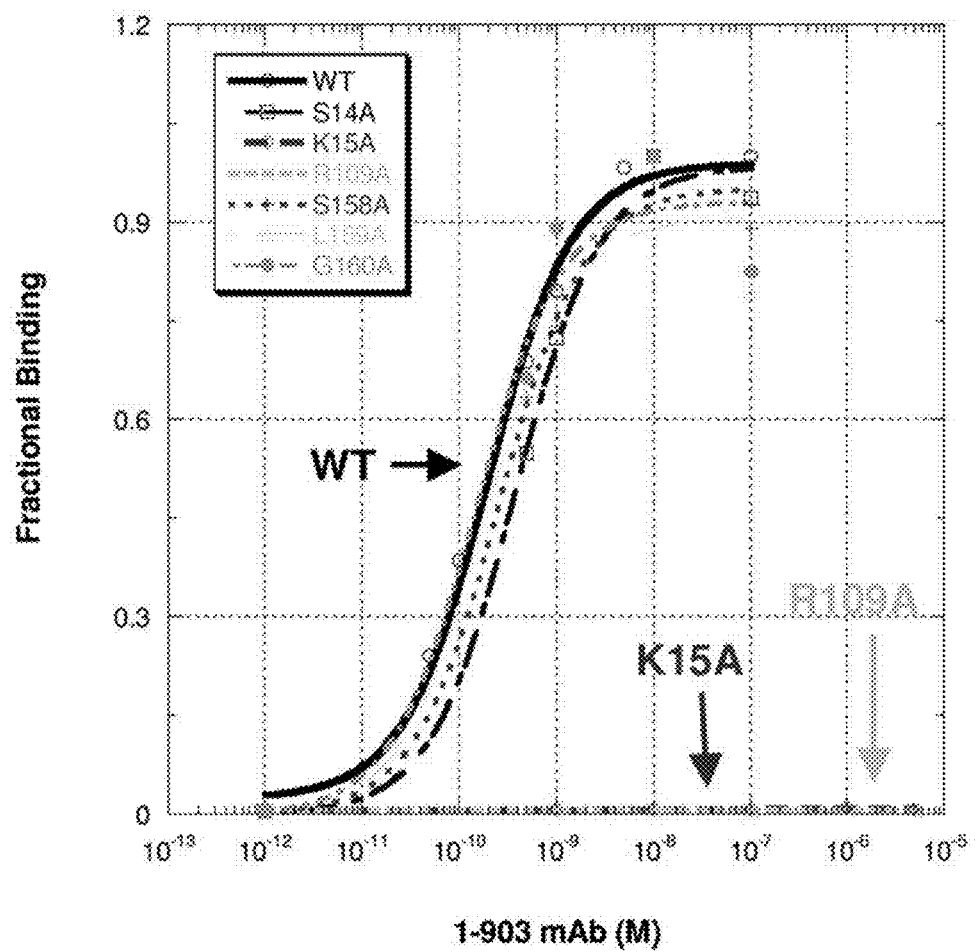
FIG. 12 is an isotherm binding data graph for monoclonal antibody 1-903-430 binding to different functional epitopes as described in Example 7. Symbols: (-○-, solid line) wild-type NGAL epitope; (-□-, solid line) NGAL epitope comprising S14A mutation; (-◇-, long dashes line) NGAL epitope comprising K15A mutation; (-x-, short dashes line) NGAL epitope comprising R109A mutation; (-+-, dotted line) NGAL epitope comprising S158A mutation; (-Δ-, extra long dashes line) NGAL epitope comprising L159A mutation; (-●-) NGAL epitope comprising G160A mutation.

FIG. 8 exhibits graphing of the antigen titration curves and demonstrates that the 1-2322-101 captured antibody does not form a sandwich with the two other members of epitope group 1 (i.e., HYB 211-01 and 1-181-128) tested in this assay. MAb 1-2322-101 can successfully form a sandwich with members of epitope group 2 (i.e., 1-903-102 and HYB 211-02) and epitope group 3 (i.e., 1-419-182). This data confirms the epitope groupings identified at the hybrid stage using the BIACore inhibition epitope grouping assay. This data also indicates that capture mAb 1-2322-101 used with secondary antibody 1-903-102 was the best antibody pairing.

Example 6

Antibody Sequencing

The purpose of this experiment was to determine the NGAL mAb 1-903-430 variable gene sequences and the NGAL mAb 1-2322-455 variable gene sequences.

mRNA was extracted from appropriate hybridoma cell cultures using commercially available reagents (Oligotex direct mRNA kit, Qiagen) following the manufacturer's recommendations. IgG heavy chain cDNA and kappa light chain cDNA was generated from the extracted mRNA using commercially available murine Ig primers, MuIgGVH3'-2 and MuIgkVL3'-1, respectively (Mouse Ig-Primer set, Novagen), following standard protocols. The variable heavy (VH) and variable light (VL) genes were then PCR amplified from their respective cDNA using pools of IgG- and Igk-specific primers from the same commercially available murine Ig primer kits referenced above using standard methods. Amplified VH and VL PCR products were cloned into a commercially available vector (pCR2.1-TOPO cloning kit, QIAGEN, Valencia, Calif.) per the manufacturer's directions and transformed into E. coli. Sequence analysis was performed (BigDye Terminator v3.1 cycle sequencing kit, Applied Biosystems, Foster City, Calif.)) on plasmids isolated from multiple transformed E. coli colonies to identify the VH and VL gene sequences.

The NGAL mAb 1-2322-455 and 1-903-430 variable gene and polypeptide sequences are shown in FIGS. 9A-B and 10A-B and SEQ ID NOS:17 and 21 (for mAb 1-903-430) and SEQ ID NOS:7 and 11 (for mAb 1-2322-455).

Example 7

Identification of Energetically Critical NGAL Residues for mAb Binding

The anti-NGAL monoclonal antibodies did not demonstrate reactivity to a series of linear sequences of about 10 to 20 residues in length that span about the entire length of NGAL. This suggests that the anti-NGAL 1-903-430 and 1-2322-455 mAb lineage reacted to conformational epitopes or discontinuous epitopes. Therefore a yeast display system was used to express unmutated (wild-type ("WT")) NGAL antigen and a library of NGAL antigens on the yeast surface as a fusion to the yeast mating protein, AGA2 (See, Boder and Wittrup, *Nature Biotechnology,* 15:553-557 (June 1997)) to determine residues critical for interaction with a panel of anti-NGAL mAbs. The wild-type NGAL antigen DNA encoding sequence was PCR amplified using the primers NGAL pYD41 for and NGAL pYD41 rev, and cloned into the yeast display vector pYD1 (Invitrogen Corp., Carlsbad, Calif.) using standard molecular biology techniques. The pYD1 vector includes a galactose inducible promoter, a C-terminal V5 epitope tag, and tryptophan and ampicillin markers for EBY100 and *E. coli* selection, respectively. The primers are as follows.

NGAL pYD41 for:
CAGCCGGCCATGGCCCAGGACTCCACCTCAGAC. (SEQ ID NO:25)

NGAL pYD41 rev:
CTCTAGACTCGAGGCCGTCGATACACTGGTCGATT (SEQ ID NO:26)
G.

A library containing random mutations in NGAL was generated by amplifying the wild-type NGAL antigen DNA encoding sequence under mutagenic conditions using a Genemorph II random mutagenesis kit (Stratagene, LaJolla, Calif.) following the manufacturer's directions using the primers pYD41 for and pYD41 rev. These primers are as follows.

pYD41 for:
TAGCATGACTGGTGGACAGC. (SEQ ID NO:27)

pYD41 rev:
CGTAGAATCGAGACCGAG. (SEQ ID NO:28)

The resulting repertoire was inserted into a linearized pYD1 yeast display vector using the inherent homologous recombination system after transformation into yeast as described (Schiestl and Gietz, *Current Genetics,* 16(5-6): 339-46 (December 1989)). Transformed yeast cells were selectively recovered using the auxotrophic tryptophan marker present on reconstituted vectors. The mutant library contained $5\times10^6$ diverse members, which is greater than 2 orders of magnitude higher than the possible number of replacements of every amino acid at each position of the 178-residue NGAL rAg.

The mutant library, induced for NGAL antigen expression, was the initial pool for serial rounds of fluorescence-activated cell sorting (FACS) as described in Chao et al., *J. Mol. Biol.,* 342:539-550 (2004)), with a panel of anti-NGAL mAbs (1-2322-101 and 1-903-102). Anti-NGAL mAbs 1-2322-101 and 1-903-102 are the parental clones from which the anti-NGAL subclones 1-2322-455 and 1-903-430 were derived, respectively. Cells were incubated with the primary NGAL mAb, washed, and remaining mAb bound to the cell surface detected with goat anti-mouse polyclonal antibody conjugated with phycoerythrin (GaM-PE). In each round of selection, full-length clones containing mutations that disrupted the ability to be bound by the particular anti-NGAL mAb were selectively enriched from those clones containing mutations that did not alter the binding interaction. Numerous individual clones isolated from each mAb selection were sequenced to identify the locations of mutations leading to loss of mAb binding. The mutant residue list was then filtered according to solvent-accessible surface areas to eliminate obvious mutations that globally disrupt NGAL antigen conformation (See, Table 8 below).

TABLE 8

| NGAL mAb 1-2322-101 | NGAL mAb 1-903-102 |
|---|---|
| S112N | K15N |
| | K15M |
| | K15Q |
| | K15T |
| | K15E |
| Q117P | R109Q |
| Q117L | R109L |
| H118P | S158F |
| A119D | L159P |
| E147K | G160V, D, C |
| E147V | |
| E147G | |

Figure 13:
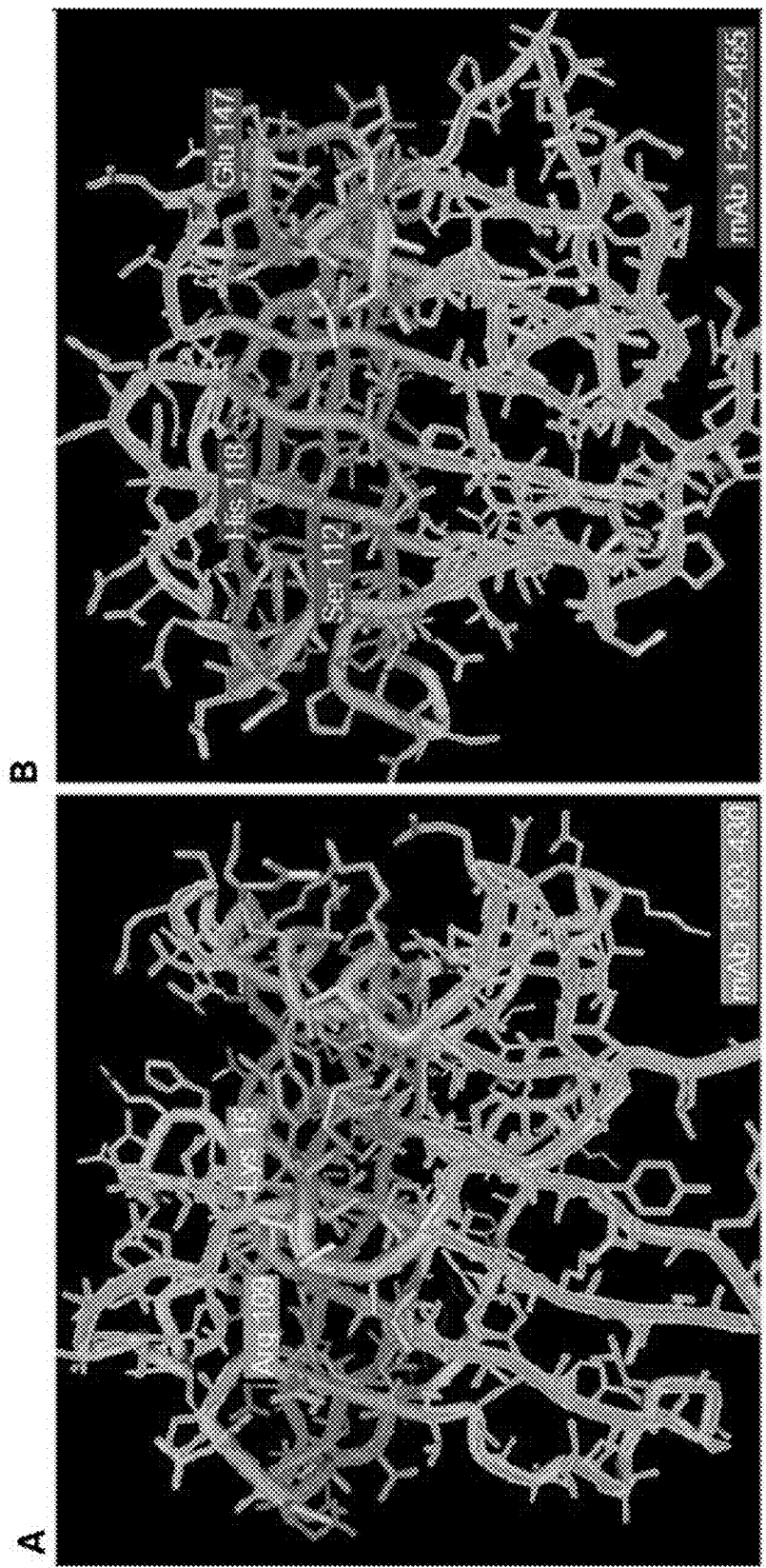
FIGS. 13A-B show molecular modeling of NGAL epitope residues on the X-ray crystal structure of human NGAL.

The side chain of each of the NGAL rAg residues identified from the epitope selections was altered by site-directed mutagenesis to alanine to confirm the functional epitope (direct contact residues) of each NGAL mAb subclone. Each NGAL rAg alanine mutant was expressed on the yeast cell surface and affinities were determined by measuring the amount of binding after titration of the respective NGAL mAb ($5\times10^{-6}$ M to $1\times10^{-11}$ M). Briefly, cells were incubated with the primary NGAL mAb (1-2322-455 or 1-903-430) from 4 hours to overnight at room temperature, washed, and mAb remaining bound to the antigen on the cell surface detected with goat anti-mouse polyclonal antibody conjugated with phycoerythrin (GaM-PE) using a flow cytometric assay.

Affinities were calculated using the following equation [1], $$F=F_{max}(L_F/(K_D+L_F))+B \qquad [1]$$

where F is the observed mean fluorescence intensity in the antigen-binding channel ("observed fluorescence"), $F_{max}$ is the amount of fluorescence at saturated mAb binding, $L_F$ is the free ligand concentration, $K_D$ is the equilibrium dissociation constant, and B is background fluorescence.

The change in Gibbs free binding energy ($\Delta\Delta G_{Ala-WT}$) was determined to assess the energetic impact of each alanine substitution for mAb binding. The change in Gibbs free binding energy upon alanine substitution was calculated using the following equation [2], $$\Delta\Delta G_{Ala-WT}=RT\ln(K_{D,Ala}/K_{D,WT}) \qquad [2]$$

where R is the gas constant ($1.9872\times10^{-3}$ kcal/M·Kelvin), T is temperature (297° Kelvin), $K_{D,Ala}$ and $K_{D,WT}$ are the equilibrium dissociation constants for mutant and wild-type antigens, respectively.

For these experiments, observed fluorescence (F) was used to solve for $K_D$ using equation [1]. The $K_D$ derived from equation [1] one was then used in equation [2] to derive the change in Gibbs free binding energy upon alanine substitution. Epitope mapping binding isotherms that were employed as data for determining contact residues are set forth in FIG. 11 and FIG. 12. The $K_D$ is read from the abscissa of each of the curves at the inflection point.

Residues with $\Delta\Delta G_{Ala-WT}$ values ≥1 kcal/mole were deemed significant and are listed in Table 9 below in bold.

TABLE 9

| Clone | $K_D$ (M) | $\Delta K_D$ | $\$\$G_{Ala-WT}$ (kcal/mole) |
|---|---|---|---|
| mAb 1-2322-455: | | | |
| WT | $8.10\times10^{-12}$ | 1.00 | 0.00 |
| S112A | $\mathbf{7.93\times10^{-11}}$ | 9.79 | 1.35 |
| Q117A | $3.07\times10^{-11}$ | 3.79 | 0.79 |
| H118A | $\mathbf{1.14\times10^{-11}}$ | 14.07 | 1.56 |
| A119G | $7.83\times10^{-12}$ | 0.97 | −0.02 |
| E147A | $\mathbf{4.92\times10^{-7}}$ | $\mathbf{6.1\times10^{4}}$ | 6.50 |
| mAb 1-903-430: | | | |
| WT | $2.04\times10^{-10}$ | 1.00 | 0.00 |
| S14A | $2.81\times10^{-10}$ | 1.38 | 0.19 |
| K15A* | $\mathbf{5.00\times10^{-6}}$ | $\mathbf{2.45\times10^{4}}$ | 5.97 |
| R109A* | $\mathbf{5.00\times10^{-6}}$ | $\mathbf{2.45\times10^{4}}$ | 5.97 |
| S158A | $2.42\times10^{-10}$ | 1.19 | 0.1 |
| L159A | $1.37\times10^{-11}$ | 0.67 | −0.23 |
| G160A | $1.64\times10^{-10}$ | 0.8 | −0.13 |

*Highest mAb titer concentration tested listed as $K_D$ value

As can be seen from Table 9, Anti-NGAL mAb 1-2322-455 directly contacts serine (S, Ser) 112, histidine (H, His) 118 and glutamic acid (E, Glu) 147 residues. Anti-NGAL 1-903-

430 directly contacts lysine (K, Lys) 15 and arginine (R, Arg) 109 side chains. Both of these residues are required for anti-NGAL 1-903-430 recognition as change of either of these residues to alanine (and elimination of their side chains) abolishes binding. Molecular modeling of the amino acid residues critical for mAb binding mutations on the X-ray crystal structure of human NGAL (PDB 1QQS) is shown in FIG. 13. It is worth noting that the residues highlighted in FIG. 13 as important in the antibody binding with human NGAL and identified by site-directed mutagenesis as described in this Example, also were identified using NMR, as described in the following Example.

Example 8

Antibody Interaction Characterization Using NMR Expression of Human NGAL in *E. Coli*

The polynucleotide sequence encoding the mature human NGAL protein (SEQ ID NO:33) was designed with EcoRI and BamHI sites at the 5'- and 3'-ends respectively. A start codon was inserted in-frame immediately upstream of the desired sequence such that it was positioned the optimal distance downstream (typically 12 to 14 bases) from the start of the vector-supplied Shine Dalgarno sequence. Following the start codon, the designed sequence codes for the mature NGAL protein (minus the signal peptide (See, SEQ ID NO:33)) plus a C-terminal sequence of six histidines. The sequence was codon optimized for high level expression in *E. coli*. Oligonucleotides coding for portions of the NGAL protein, and containing complementary overlapping ends were annealed, end-filled and the resulting assembled product amplified in a two-step PCR process. In the first PCR step, the 5'-cloning site (EcoRI) and a sequence coding a portion of the C-terminal histidine tag were introduced at the ends of the assembled gene and in the second PCR step, the remainder of the histidine tag-encoding sequence was incorporated followed by a stop codon. The amplified product was purified, digested with EcoRI and BamHI and ligated into a similarly-digested pKRR826 vector (a pL-based expression vector which generates a non-fusion product; described, e.g., in U.S. Pat. No. 5,922,533). The ligation products were transformed into the protease-deficient BL21 strain of *E. coli*. Clones were selected by ampicillin resistance. A clone possessing of the designed human NGAL sequence (called NGAL(+)1) was confirmed.

In order to minimize the potential of the expressed NGAL to form disulfide-linked dimers, amino acid 87 of clone NGAL(+)1 was altered from a Cys residue to a Ser residue using a QuikChange Site-Directed Mutagenesis Kit (Stratagene, Cedar Creek, Tex.) (See, SEQ ID NOS:29 and 30 and FIG. 14). The sequence of the mutagenized plasmid was confirmed (mutated NGAL polynucleotide sequence set forth at SEQ ID NO:29, and encoding a Met at residue −1), and the resulting plasmid (called NGAL(+)mut8) was transformed into the protease-deficient *E. coli* strain BL-21 (Amersham Pharmacia Biotech (ApBiotech), Uppsala, Sweden, now GE Healthcare).

Cells were grown at 30° C. until an $OD_{595}$ of 0.55 was reached, at which time the temperature was shifted to 42° C. to induce expression. After 3 hours of induction at 42° C., the cells were harvested by centrifugation and the pelleted cells were lysed with BugBuster Extraction Reagent (Novagen, Madison, Wis.). The expressed NGAL was present in the soluble fraction of the lysate, was purified using a His Bind® Purification Kit (Novagen, Madison, Wis.), and was dialyzed into 0.01 M phosphate buffer, pH 7.4 containing 0.15 M NaCl (PBS).

Preparation of Isotope-Labeled NGAL for NMR Studies

Human NGAL protein was prepared by expressing the protein in *E. coli* strain BL21 as described previously herein. Uniformly $^{15}N$-labeled human NGAL samples in a $^2H$ background were prepared by growing cells in commercial rich media (Cambridge Isotope Laboratories (CIL), Andover, Mass.) that contained 100% $^2H_2O$. Uniformly $^{13}C$, $^{15}N$-labeled samples were prepared on M9 media using U-$^{13}C$-glucose (3 g/L, Cambridge Isotope Laboratories (CIL), Andover, Mass.) and $^{15}NH_4Cl$ (1 g/L, Cambridge Isotope Laboratories (CIL), Andover, Mass.), $H_2O$ and 10 µM $FeSO_4$ was added. Soluble protein was purified as previously described herein.

Preparation of Fab Fragments from Monoclonal Antibodies (mAb 2322, mAb 809, mAb 269, mAb 181 and mAb 903)

Selected hybridomas were scaled up and monoclonal antibodies were isolated from the tissue culture media using rProteinA-PorosA50 columns. Six monoclonal antibodies were selected for further studies, namely, mAb 2322, mAb 809, mAb 269, mAb 181 and mAb 903.

Figure 15:
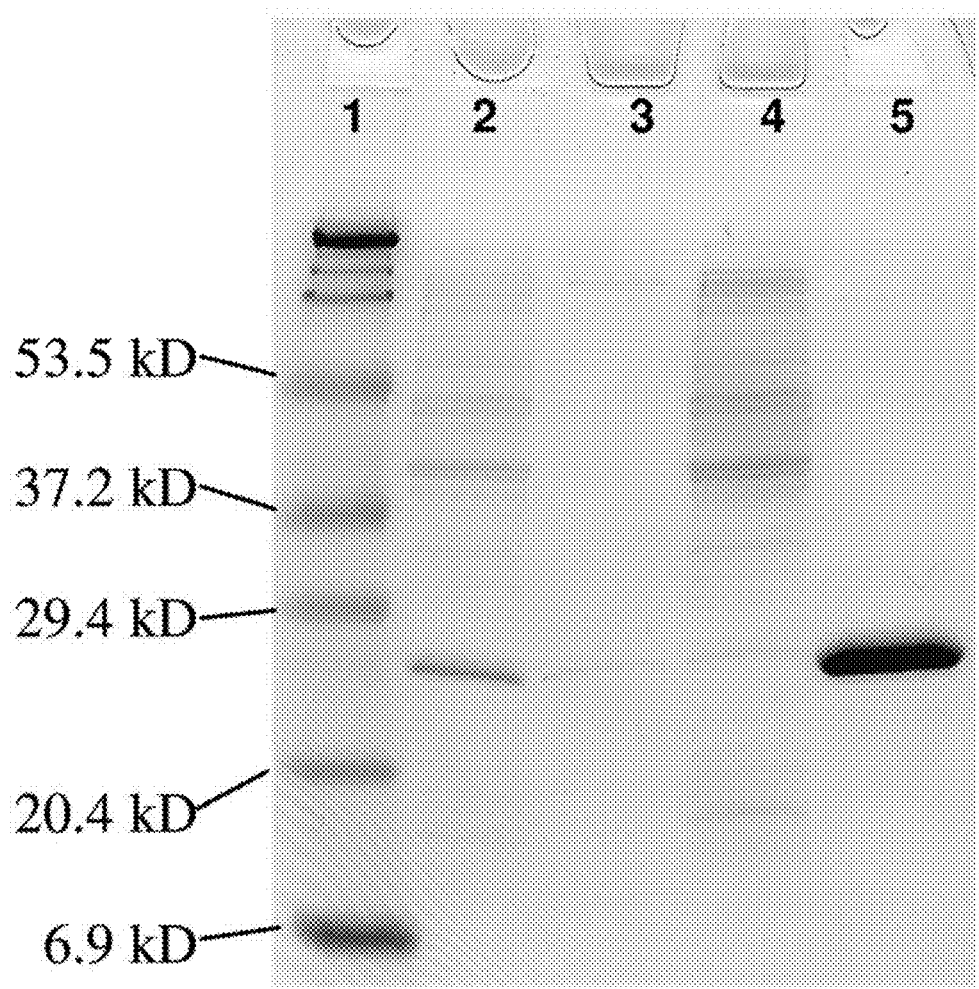
FIG. 15 shows a SDS-PAGE analysis of samples derived from the induction and purification of the NGAL(+)mut8 protein as described in Example 8. Lanes: (1) size markers; (2) lysate supernatant; (3) lysate pellet; (4) His•Bind® unbound fraction; and (5) His•Bind® purified fraction.

Fab fragments were prepared by limited digestion of the IgG antibodies with papain using a common digestion protocol as follows. Briefly, antibodies at the concentration range of 2-6 mg/mL in PBS were mixed with immobilized papain (Pierce Biotechnology, Rockford, Ill.) at the IgG/papain ratio of 100:1 (w/w) in the presence of 1 mM Dithiothreitol (DTT) and 1 mM EDTA and placed on a rotator at room temperature. Digestion was monitored by running samples every 30 or 60 minutes on a Tosoh K3433 G2000 SWx1 HPLC column. After completion, immobilized enzyme was removed by centrifugation and samples were passed through a rProteinA-PorosA50 column to absorb undigested IgG and Fc fragments. After concentration, Fab fragments were dialyzed against PBS. Purity of the Fab fragments higher than 80% was confirmed by PAGE and HPLC (See, FIG. 15). None of the particular impurities in the Fab preparations exceeded 5%.

NMR Experiments (NGAL Resonance Assignments)

NMR samples contained 0.15-0.50 mM labeled protein in 90% $H_2O$/10% $^2H_2O$. The protein resonance assignments for human NGAL were obtained from the public database Biological Magnetic Resonance Data Bank (database entry 4267; www.bmrb.wisc.edu/data/library_gen_saveframe) (See, Coles, M., et al., J. Mol. Biol. 289: 139-157 (1999)). The construct used in this example has a C87S substitution but is otherwise the same as that used in the work described in Coles, M., et al., J. Mol. Biol. 289: 139-157 (1999). A 3D HNCA (See, Yamazaki, T., et al., J. Am. Chem. Soc. 116: 11655-11666 (1994)) experiment and a 3D $^1H/^{15}N$-resolved NOESY (See, Fesik, S. W., et al., J. Magn. Reson. 78: 588-593 (1988)) spectra were acquired and compared to the published assignments (See, Coles, M., et al., J. Mol. Biol. 289: 139-157 (1999)). No significant differences were observed in the assignments except for residues adjacent to the C87S mutation. Assignments were made using samples consisting of 500 µM human NGAL in 50 mM sodium acetate buffer at pH 6.0. All NMR spectra were collected at 25° C. on Bruker DRX600 or DRX800 NMR spectrometers.

NMR Experiments (Binding Induced Shifts)

Human NGAL-Fab complexes contained 150 µM isotope-labeled human NGAL and 200 µM of unlabeled Fab fragments derived from each of six mAb were studied. Chemical shifts or broadening of peaks was monitored by comparing: $^1H$-$^{15}N$-TROSY HSQC (See, Pervushin, K., et al., *Proc Natl Acad Sci USA* 94, 12366-71 (1997) and Shimada, I, *Methods*

*Enzymol* 394, 483-506 (2005)) spectra of $^{15}$N,$^2$H-labeled NGAL or $^1$H-$^{13}$C HSQC (See, Bodenhausen, G, et al., *Chem. Phys. Lett.* 69, 185-188 (1980)) of $^{13}$C, $^1$H labeled human NGAL alone and in the NGAL-Fab complex. Changes in the chemical shift or relative broadening were categorized as 'no change' if a resonance was minimally perturbed by antibody binding, or 'medium' or 'large' perturbations depending on the magnitude of spectral change. Examples of these perturbations are shown in FIG. 16 for human NGAL after addition of mAb2322.

NMR Results and Discussion

NMR is a method that allows for the determination of contact residues or epitopes of protein-protein interactions (See, Shimada, I, *Methods Enzymol.*, 394:483-506 (2005), Clarkson, J., et al., *Biochem Soc Trans.*, 31:1006-9 (2003), Foster, M. P., et al., *Biochemistry*, 46:331-40 (2007), Zuiderweg, E. R., *Biochemistry*, 41:1-7 (2002), Betz, S. F., et al., *Proc Natl Acad Sci USA*, 95:7909-7914 (1998)). The method can identify contact residues that are not contiguous in the protein sequence but are in close proximity because of the fold of the protein, so-called 'discontinuous' or 'conformational' epitopes. The NMR spectrum reflects the native antigen—antibody interactions and is a very robust indicator of contacts.

Figure 16:
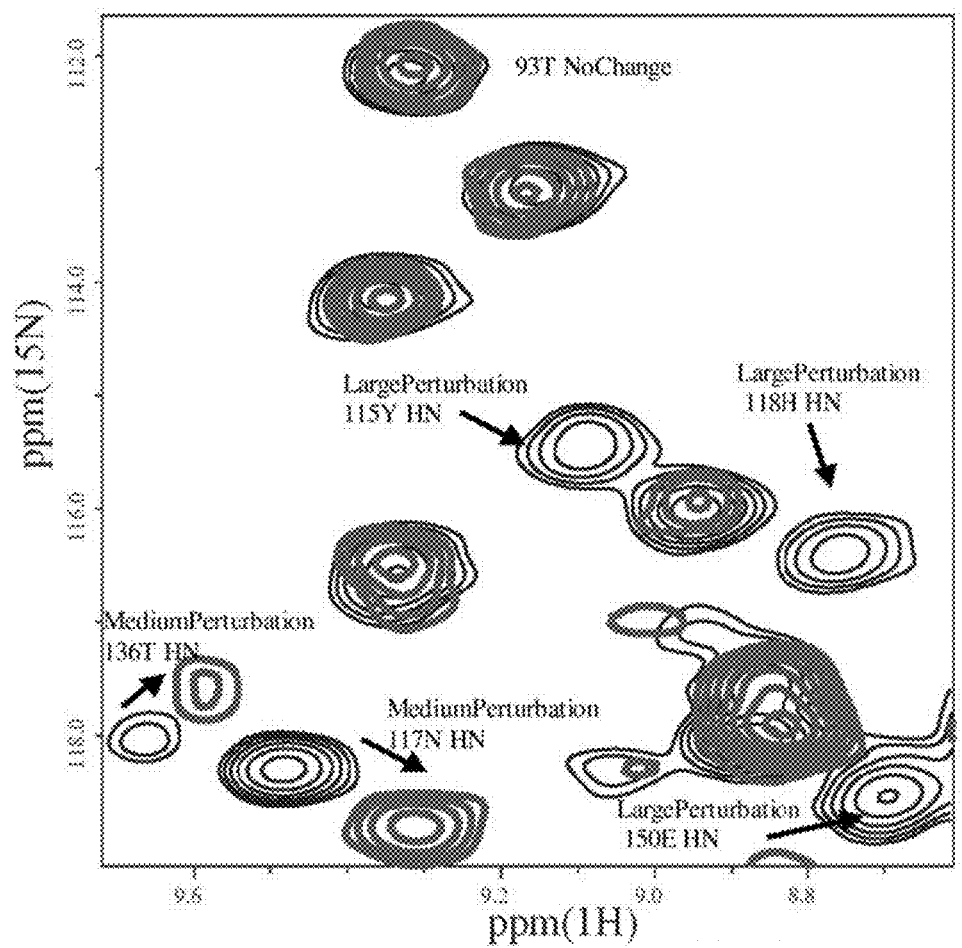
FIG. 16 shows a portion of the $^1H$-$^{15}N$ TROSY HSQC spectra of human NGAL after addition of an excess of mAb 2322. Assignments are based on those deposited in the public database *Biological Magnetic Resonance Data Bank* (database entry 4267), and examples of the perturbation categories observed are shown. Shifts due to antibody binding (indicated by gray thick lines) are superimposed on the corresponding spectra of the free protein (shown as fine black lines).

FIG. 16 shows a section of a $^1$H-$^{15}$N TROSY HSQC spectra (See, Shimada, I, *Methods Enzymol.*, 394:483-506 (2005) and Fernandez, C., et al., *Curr Opin Struct Biol.*, 13:570-80 (2003)) of human NGAL plus the human NGAL/antibody mAb 2322 complex. FIG. 16 shows that most of the resonances in the spectra of the complex (broad gray lines), overlay almost exactly on the resonance positions of the free protein spectra (fine black lines). These human NGAL resonances are not significantly affected by antibody binding. An example is 93T in FIG. 16, which shows no significant spectral changes in position and is thus inferred to be distal from the antibody contact site (See, Shimada, I, *Methods Enzymol.*, 394:483-506 (2005), Clarkson, J., et al., *Biochem Soc Trans.*, 31:1006-9 (2003), Foster, M. P., et al., *Biochemistry*, 46:331-40 (2007), Zuiderweg, E. R., *Biochemistry*, 41:1-7 (2002)). However, residues like 115Y and 150E which are highly perturbed by the presence of the antibody are inferred to be either in direct contact with the antibody (a first contact shell) or to be a residue that is in contact with residues in direct contact (a second sphere contact). Both of these contacts result in a spectral signature that can be detected by NMR of the mAb contact. These data showing perturbation on residues 115, 118 and 150 are consistent with and complement the loss-of-function mutation data and change in free energy binding data in Example 7, which supports that residues 112, 118 and 147 are directly contacted by mAb 2322. It is to be expected that these or nearby residues might be perturbed by the binding of the antibody.

In addition to the $^1$H-$^{15}$N TROSY HSQC spectra, the perturbation of side-chain resonances can be measured, in particular methyl groups from $^1$H-$^{13}$C HSQC spectra. Because the resonances overlap, only a handful of the $^1$H-$^{13}$C resonances were used in the analysis. This additional data from $^1$H-$^{13}$C supplements the results of the $^1$H-$^{15}$N TROSY HSQC spectra and is included in Table 10 below in the listing of residues with perturbed resonances.

TABLE 10

Antibody-induced perturbations in NGAL backbone ($^1$H-$^{15}$N) NMR spectra

| Amino Acid Residue/Antibody | mAb 2322 | mAb 809 | mAb 269 | mAb 181 | mAb 903 | mAb 419 |
|---|---|---|---|---|---|---|
| 15 Lys | 2 | 2 | 0 | 2 | 3 | 0 |
| 22 Phe | 0 | 0 | N.D. | N.D. | 2 | 0 |
| 24 Asp | 0 | 0 | 2 | N.D. | 0 | 0 |
| 26 Gln | 0 | 0 | 2 | 0 | 0 | 0 |
| 29 Gly | 0 | 0 | N.D. | 0 | 0 | 0 |
| 38 Gly | 0 | 0 | 0 | 0 | 2 | 0 |
| 52 Tyr | 0 | 0 | 0 | 0 | N.D. | 2 |
| 54 Thr | 0 | 0 | 0 | 0 | 0 | 0 |
| 59 Lys | 0 | 0 | N.D. | 0 | 0 | 2 |
| 61 Asp | 3 | 3 | 0 | 0 | 0 | 0 |
| 64 Tyr | 0 | 0 | 0 | 0 | 2 | 2 |
| 81 Arg | 0 | 0 | 0 | 0 | N.D. | 2 |
| 84 Val | 0 | 0 | 0 | N.D. | 1 | 2 |
| 86 Gly | 0 | 0 | 0 | 0 | 2 | 1 |
| 93 Thr | 0 | 0 | 0 | 0 | 2 | 2 |
| 94 Leu | 0 | 0 | 0 | 0 | 2 | 2 |
| 95 Gly | 0 | 0 | 0 | 0 | 2 | 2 |
| 99 Ser | 0 | 0 | 0 | 0 | 3 | 3 |
| 107 Leu | 0 | 0 | 0 | 0 | 0 | N.D. |
| 109 Arg | 0 | 0 | 0 | N.D. | N.D. | 0 |
| 110 Val | 0 | 0 | 0 | 0 | 0 | 0 |
| 111 Val | 2 | 2 | 0 | 2 | N.D. | N.D. |
| 112 Ser | 2 | 2 | 2 | 2 | 0 | 0 |
| 113 Thr | 0 | 0 | N.D. | N.D. | 0 | 0 |
| 115 Tyr | 2 | 2 | N.D. | N.D. | N.D. | N.D. |
| 116 Asn | 2 | 2 | 2 | 2 | 0 | 0 |
| 117 Gln | 3 | 3 | 3 | 3 | 3 | −0.11 |
| 118 His | 3 | 3 | 3 | 2 | 0 | 0 |
| 127 Ser | 0 | 0 | 0 | 0 | 0 | 0 |
| 135 Ile | 1 | 1 | 0 | N.D. | N.D. | N.D. |
| 141 Thr | 2 | 2 | 2 | 2 | 0 | 0 |
| 142 Lys | 3 | 3 | 2 | 3 | 0 | 0 |
| 143 Glu | 3 | 3 | 2 | 3 | 0 | 0 |
| 145 Thr | 2 | 2 | 2 | 2 | N.D. | 0 |
| 149 Lys | 0 | 0 | 0 | 0 | 0 | 0 |
| 150 Glu | 3 | 3 | 2 | 3 | N.D. | 0 |
| 154 Arg | 3 | 3 | N.D. | 3 | N.D. | 0 |

TABLE 10-continued

Antibody-induced perturbations in NGAL backbone ($^1$H-$^{15}$N) NMR spectra

| Amino Acid Residue/Antibody | mAb 2322 | mAb 809 | mAb 269 | mAb 181 | mAb 903 | mAb 419 |
|---|---|---|---|---|---|---|
| 160 Gly | 0 | 0 | 0 | 0 | N.D. | 0 |
| 166 Ile | 0 | 0 | 0 | 0 | 0 | 0 |

The perturbation amplitudes in Table 10 are ranked according to the following classification:
(a) "N.D."—Not Determined because resonance status in the experiment was ambiguous. Peaks are not sufficiently resolved and perturbations cannot be assigned.
(b) "0"—No change, Shift<0.2 ppm (1H+15N). Broadening similar to other peaks.
(c) "1"—Small shift: 0.5 ppm>Shift>0.2 ppm (1H+15N).
(d) "2"—Big shift. Shift>0.5 ppm (1H+15N).
(e) "3.0—Broadening or large shift, peak disappears.
(f) Peaks that overlapped are not included in Table 10.

Figure 17A:
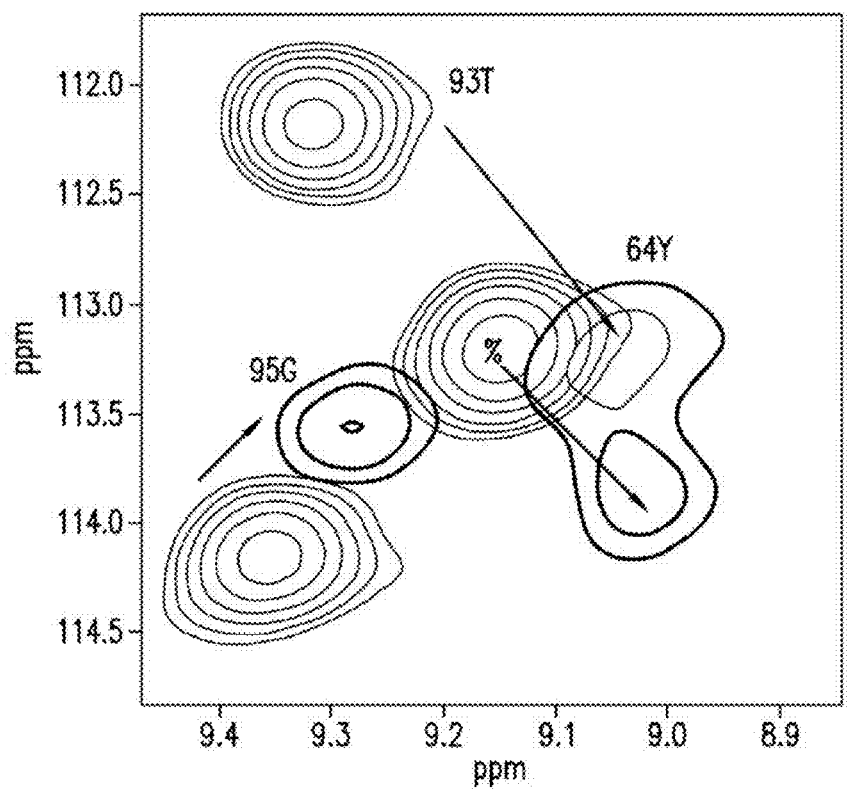
FIGS. 17A-B show portions of the $^1H$-$^{15}N$ TROSY HSQC spectra of human NGAL, with shifts due to antibody binding (spectra drawn with gray thick lines) superimposed on the corresponding spectra of the free protein (shown as fine black lines).
Figure 17B:
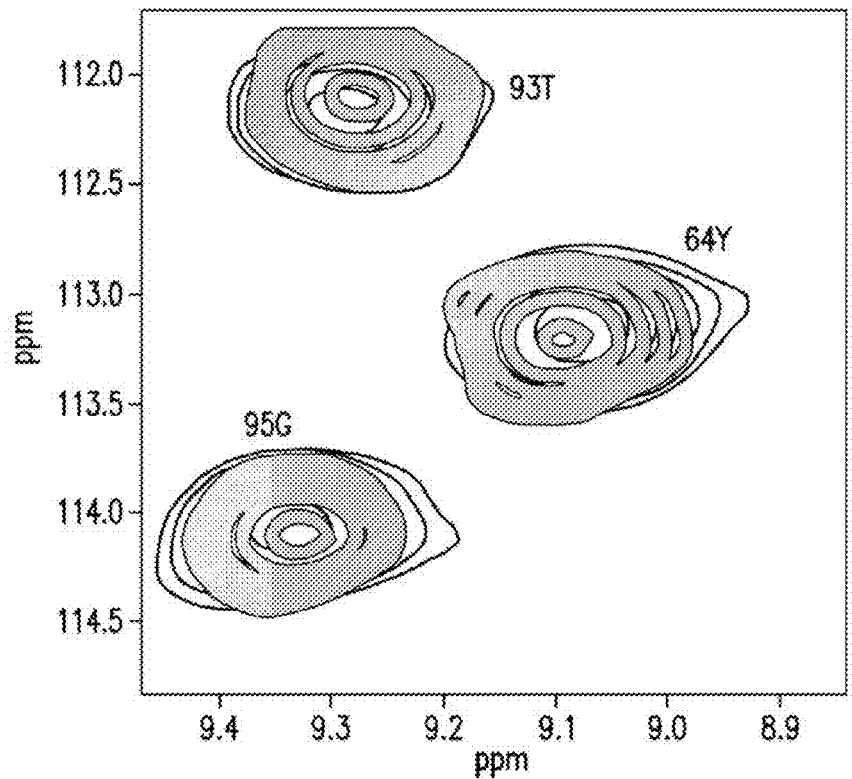
Figure 18A:
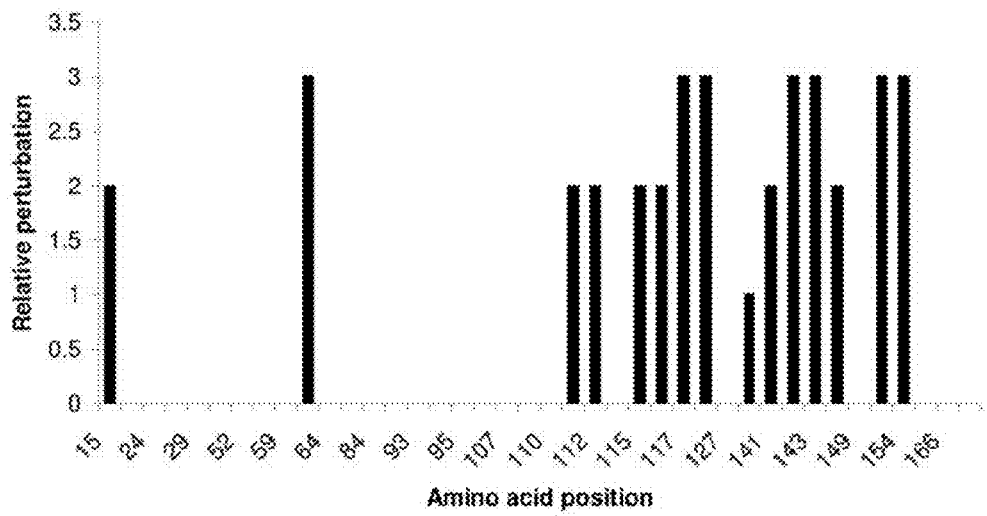
FIGS. 18A-F are graphs that show the NGAL backbone $^{1}H$–$^{15}N$ resonance perturbations caused by binding of various monoclonal antibodies (mAbs) as described herein in terms of amino acid position (abscissa) versus relative perturbation (ordinate).
Figure 18B:
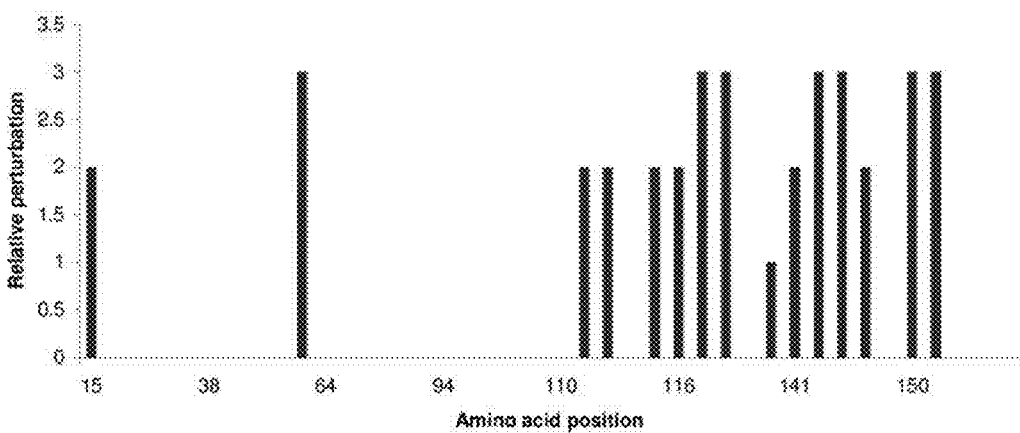
Figure 18C:
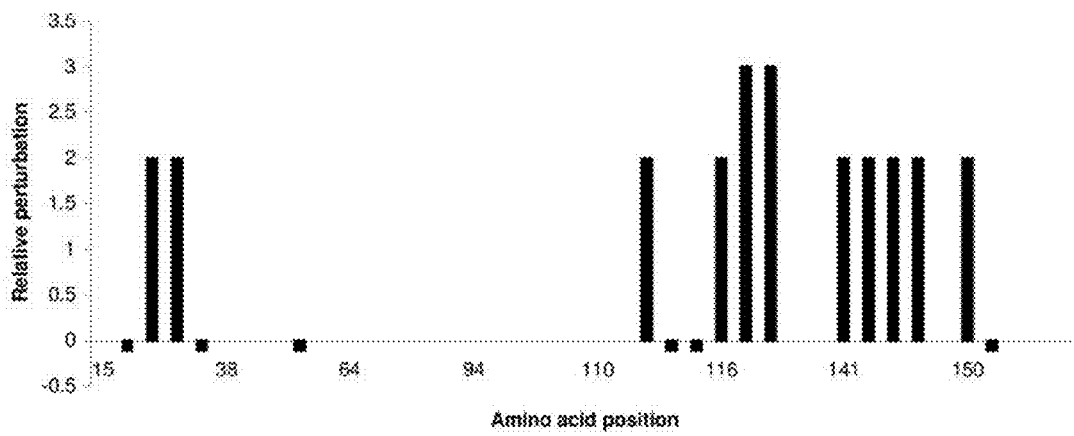
Figure 18D:
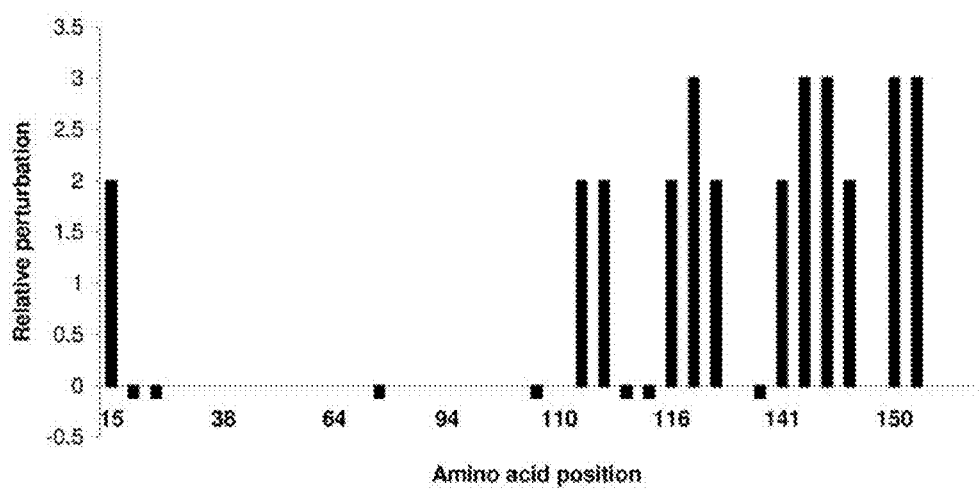
Figure 18E:
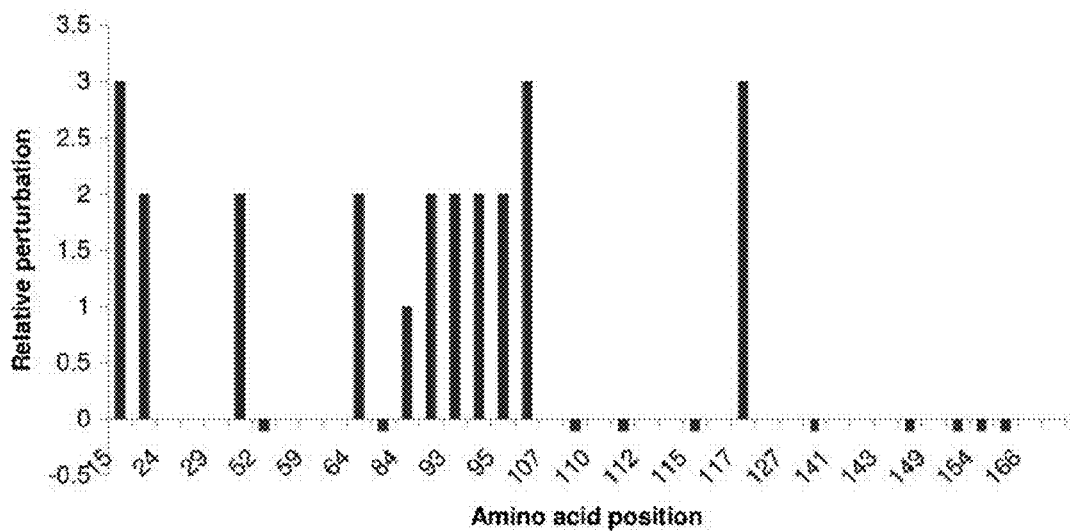
Figure 18F:
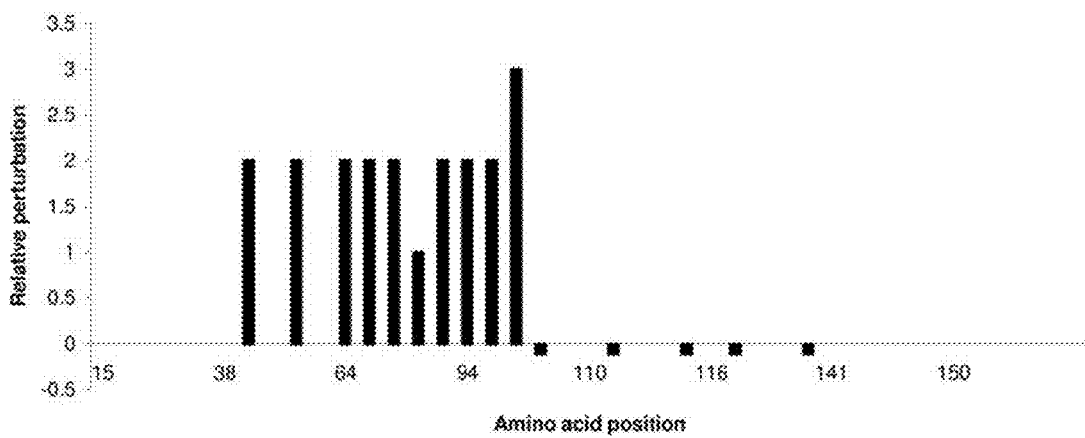

As shown in FIG. 17A, the perturbations of resonances of the native antigen human NGAL by mAb 903 binding (FIG. 17A) can be observed and differentiated from those observed by binding of a different antibody such as mAb 2322 (FIG. 17B). This illustrates how different binding interfaces have characteristic spectral changes that are distinct. This approach allows for the differentiation between antibodies that interact on different surfaces of the antigen protein human NGAL.

FIGS. 18A-18F show graphs that summarize the resonance changes observed for all the studied antibodies. When the resonances changes (ordinate) are graphed on the sequence (abscissa) it is apparent that the perturbed resonances are not all from residues that are contiguous in the sequence. In addition, because the plots compare the same set of resonances, it is easy to see when the resonance perturbations are different for the antibodies. From the comparison of this data, the six studied mAbs can be combined into three distinct groups. The first group ("Epitope Group 1") includes mAb 2322, mAb 809, mAb 269 and mAb 181 shown in FIGS. 18A-D. Two remaining antibodies, mAb 903 (FIG. 18E) and mAb 419 (FIG. 18F) demonstrate distinctly different NMR resonance perturbation signatures and are assigned to two separate groups, namely, group 2 and group 3 (i.e., "Epitope Group 2" and "Epitope Group 3", respectively).

Figure 19:
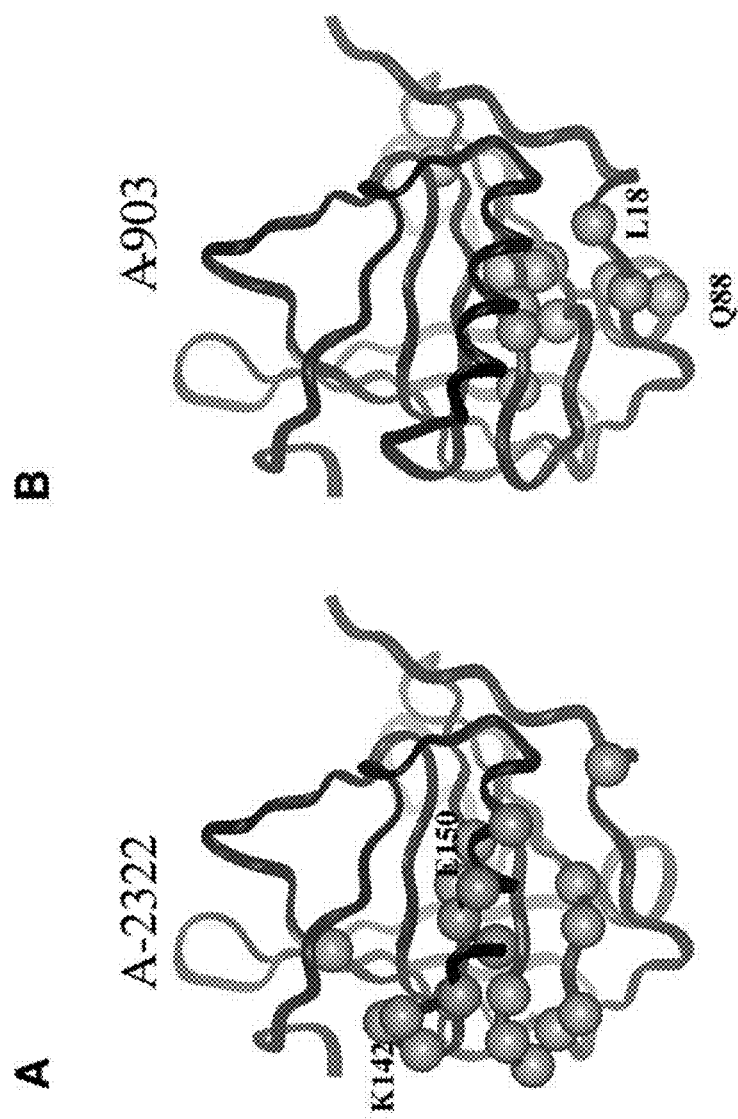
FIGS. 19A-B show the mapping of perturbed resonances onto the three dimensional (3D) structure of the human NGAL protein. Specifically, this figure shows the backbone ribbon depiction of human NGAL (pdb id: 1x89), with the perturbed residues' amides rendered as spheres and numbered according to the mature human NGAL sequence minus the signal peptide.

FIGS. 19A-B show how the residues for which resonances are perturbed are mapped onto the three-dimensional structure of the protein. The NGAL three-dimensional structure was determined using NMR (See, Coles, M., et al., *J Mol Biol.,* 289:139-57 (1999)) and X-ray crystallography (See, Goetz, D. H., et al., *Mol Cell.,* 10:1033-43 (2002) and Holmes, M. A., et al., *Structure,* 13:29-41 (2005)). As expected, the amino acid residues whose resonances are affected by antibody binding are located on the protein surface and likely participate in the contact interactions with the antibody. These amino acid residues are often defined as the first sphere, or contact, residues. There are also so-called the second sphere residues which are not exposed on the surface but are buried in the interior of the protein molecule. These amino acids are responsible for the positioning of the residues in the first sphere and their microenvironment can be also perturbed upon interaction with antibody. Thereupon, these amino acid residues will also contribute to the NMR signature of the binding epitope. Additionally, it is also often possible to register a perturbation in the resonance of residues on the periphery of the epitope that is not in the immediate contact with antibody but became perturbed due to binding-induced conformational adjustments in the binding surface.

As shown in FIG. 19A, the residues whose resonances of human NGAL are perturbed by mAb 2322 (e.g., from Table 11 below, residues from K142 to E150) are all on one face of the protein. These residues include residue 147, identified independently by loss-of-function mutation and change in free energy binding data in Example 7. Residues perturbed on the surface are in the direct contact sphere. Residues in the second sphere contact these residues and are likely perturbed indirectly because of structural rearrangements due to binding. These residues can be used to define the interaction surface with the antibody. The surface consists of non-contiguous residues that are in close proximity because of the fold of the protein. The antibody therefore recognizes a native-like fold of the protein.

The corresponding location of residues perturbed by mAb 903 binding is shown in FIG. 19B. This defines an interaction surface that is displaced from that of mAb 2322 as shown in the figure is located on the bottom of the protein. The two contact regions have interaction surfaces defined by NMR resonance perturbations that do not overlap and thus can be used to differentiate them. Thus, even though they are on adjacent faces of the protein there are contacts that are unique to each antibody. Also worth noting are the proximity of perturbed residues L18 and Q88 to residues 15 and 109, identified by loss-of-function mutation and change in free energy binding data in Example 7.

The shifts in methyl ($^1$H-$^{13}$C) group spectra and in amide ($^1$H-$^{15}$N) spectra and the broadening in amide ($^1$H-$^{15}$N) spectra are summarized below in Table 11.

TABLE 11

| Fab Fragment | Shift in methyl ($^1$H—$^{13}$C) group spectra | Shift in amides ($^1$H—$^{15}$N) spectra | Broadening in amides ($^1$H—$^{15}$N) spectra |
|---|---|---|---|
| 1-809-174 | 51, 66, 67 (148) 110, 135 | 112, 117, 116, 135, 138, 139 | 15, 111, 114, 115, 118, 141, 142, 143, 145, 150, 154 |
| 1-903-102 | 16, 18, 84, 93, 94, 103, 108, 120, 121 | 86, 95, 64, 93, 94 | 88, 18, 84 |
| 1-419-182 | 66, 70, 80, 94, 84, 93 | 28, 93, 64, 95, 86, 94 | 62, 99, 59, 81, 80, 63 |
| 1-181-150 | 51, 110, 136, 120 (148)* | 117, 116 | 15, 111, 118, 141, 142, 143, 145, 150, 154 |
| 1-269-161 | 51, 55, 66, 94, 114 | 118, 117 | 24, 26, 116, 141, 142, 143, 145, 150 |
| 1-2322-455 | 51, 66, 110, 135, (148)* | 112, 116, 117 (135, 138)* | 15, 111, 114, 115, 118, 141, 142, 143, 145, 149, 150, 154 |

*Low intensity peaks in native NGAL. The shifted methyl (tentatively assigned to 148) is at $^{13}$C ppm 22.14 and $^1$H - 0.54 ppm Generally, the data in this Example agree with and complement the epitope mapping data obtained in Example 7 on loss-of-function mutation and change in free energy binding data. In some cases, absence of $^{13}$C/$^{15}$N mapping data may stem from the magnitude of the shift being so great as to prevent identification of the shifted peak.

Example 9

Determination of Antibody Affinities and Sandwich Formation in Solution

Labeling of NGAL and mAbs with Fluorescent Labels and Quenchers

Human NGAL (C87S) produced in *E. coli* was purified using His•Bind Purification Kits (Novagen, EMD Chemicals, Inc. San Diego). Purified human NGAL was labeled using BHQ-10S succinimidyl ester (Black Hole Quencher®, Biosearch Technologies, Inc. Novato, Calif.). Anti-NGAL mAbs (1-809-174, 1-903-102, 2-9405, 1-2322-101) were labeled with ALEXA Fluor 488 carboxylic, succinimidyl ester (Invitrogen Corp., Carlsbad, Calif.). The unlabeled BHQ-10s and ALEXA Fluor 488 were removed on a G-25 column equilibrated with PBS.

The concentration of the labeled NGAL was determined by UV absorption in a 1 cm cuvette using $E_{279}^{1\ mg/L}=1.25$ on a Cary 4 spectrophotometer (Varian, Sugarland, Tex.), with corrections included for contributions from BHQ-10S. The concentrations of the labeled mAbs were determined by UV absorption in 1 cm cuvette using $E_{279}^{1\ mg/mL}=1.50$, with corrections included for contributions from the ALEXA Fluor 488.

The labeling procedures and concentration determinations of the labeled proteins were performed according to instructions provided by the manufacturers.

Determination of the Equilibrium Dissociation Constants

The equilibrium dissociation constants ($K_D$) of NGAL and six anti-NGAL antibodies were measured in direct binding experiments. The ALEXA 488-mAbs were kept at constant concentration (0.05 nM) while the BHQ-NGAL concentration was incrementally increased from the picomolar to the sub-micromolar range in the series of 15 samples. After 30 minutes incubation, all samples were measured on an SLM 8100 photon counting spectrofluorimeter. Samples were excited at 480 nm, and the emission was collected through a 530 nm (30 nm bandwidth) interference filter (Chroma Technology Corp., Rockingham, Vt.). All binding measurements were performed in 10 mM HEPES buffer, pH 7.4, containing 0.15 M NaCl, 3 mM EDTA, and 0.005% surfactant P20.

The fluorescence emission of ALEXA 488-labeled antibodies (mAb 2322, mAb 809, mAb 269, mAb 181 and mAb 903) were found to be quenched 25-40% upon binding to the BHQ-labeled NGAL. Unfortunately, binding of BHQ-NGAL to ALEXA 488-mAb 419 quenched the antibody fluorescence by less than 10%, which made it impossible to accurately quantitate its titration. Thus, the dissociation constant for mAb 419 was not determined.

Assuming that the changes in fluorescence intensity are directly proportional to the fraction of the antibody bound to BHQ-NGAL, the concentration of the unliganded (or free) BHQ-NGAL can be calculated from the equation [3] below:

$$\text{Ligand}_{free} = \text{Ligand}_{total} - \text{ABS}_{total} \times F_{bound} \qquad [3]$$

where $\text{Ligand}_{total}$ and $\text{ABS}_{total}$ are the BHQ-NGAL concentration and total antibody binding sites, respectively, and $F_{bound}$ is the fraction of bound antibody sites. The binding data were fitted with a simple binding model to obtain the equilibrium dissociation constant ($K_D$) according to equation [4]:

$$F_{bound} = \frac{[\text{Ligand}]_{free}}{K_d + [\text{Ligand}]_{free}}, \qquad [4]$$

Figure 20:
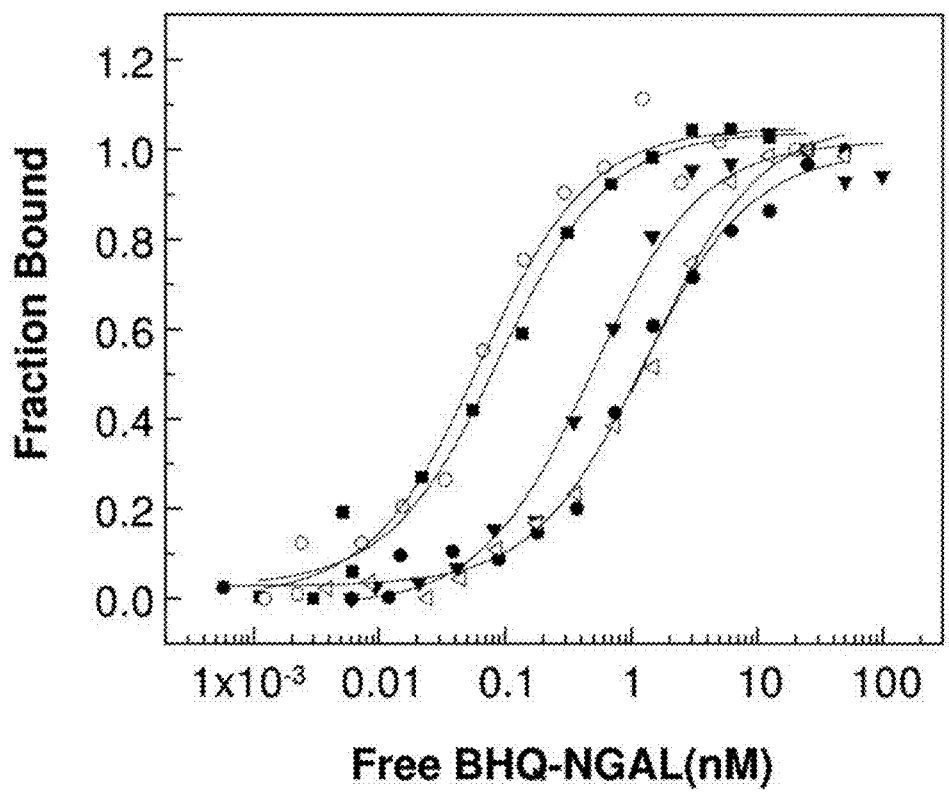
FIG. 20 shows the binding curves of anti-NGAL mAbs and NGAL (free NGAL concentration on the abscissa and fraction bound on the ordinate), and their calculated dissociation constants ($K_d$) as listed in Table 9. Symbols: (-●-) mAb 903; (-■-) mAb 809; (-○-) mAb 2322; (-▼-) mAb 181; (-Δ-) mAb 269.

FIG. 20 shows the binding curves of anti-NGAL mAbs and NGAL, and the calculated equilibrium dissociation constants ($K_D$) for anti-NGAL mAbs are listed in Table 12.

TABLE 12

| MAb | $K_D$ (nM) |
|---|---|
| 1-809-174 | 0.09 ± 0.02 |
| 1-903-102 | 1.2 ± 0.2 |
| 1-2322-101 | 0.06 ± 0.02 |
| 1-181-150 | 0.57 ± 0.1 |
| 1-269-161 | 1.4 ± 0.1 |
| 1-419-182 | N/A |

All of the measured values in Table 12 indicate high affinities to NGAL.

Evaluation of Anti-NGAL Antibodies for Sandwich Formation

The ability to form a complex consisting of two antibodies and human NGAL, hereafter referred to as a sandwich, was evaluated for the six anti-NGAL mAbs using dual-color fluorescence cross-correlation spectroscopy (DC-FCCS).

The concept of DC-FCCS was formulated by Eigen and Rigler as described in *Proc Natl Acad Sci USA* 91:5740-5747 (1994). Cross-correlation curves are calculated by temporal correlation of the signals measured in two optical channels optimized for two different emission wavelengths. When two molecular species of interest are tagged with two different fluorescent labels, only the molecular complexes can be simultaneously detected in both channels. This results in the amplitude of the cross-correlation plot being proportional to the concentration of molecular complex in solution. DC-FCCS can be applied to practically any size molecules. Therefore, it extends the capabilities of traditional fluorescence correlation spectroscopy (FCS), which is limited by the requirement of there being at least a two-fold difference in the diffusion coefficient of free and bound species in order to resolve these species using the autocorrelation function analysis (See, Meseth, U., et al., *Biophys J.*, 76:1619-31 (1999)).

The first experimental realization of DC-FCCS was accomplished in a study of hybridization of two single-stranded oligonucleotides labeled with different fluorescent dyes (See, Schwille, P., et al., *Biophys J.*, 72:1878-86 (1997)). Each fluorescently-labeled single-stranded DNA was monitored independently in a separate channel such that the amplitude of the calculated cross-correlation curve depended on the amount of the double-stranded DNA complex formed. Later, DC-FCCS was used to study activities of several DNA-processing enzymes (See, Collini, M., et al., *Nucleic Acids Res.*, 33:e165 (2005), Kettling, U., et al., *Proc Natl Acad Sci USA*, 95:1416-20 (1998) and Rarbach, M., et al., *Methods*, 24:104-116 (2001)), to detect specific DNA sequences (See, Berland, K. M., *J Biotechnol.*, 108:127-136 (2004)), and to characterize simultaneous binding of two DNA duplexes to a protein (See, Rippe, K., *Biochemistry*, 39:2131-2139 (2000)). Besides DNA studies, application of DC-FCCS also has been proposed for quantitative characterization of protein-protein interactions (See, Schwille, P., et al., *Biophys., J* 72:1878-1886 (1997) and Weidemann, T., et al., *Single Molecules*, 3:49-61 (2002)).

DC-FCCS Instrument and Data Analysis

DC-FCCS experiments were performed using a dual-channel fluorescence correlation spectrometer ALBA (ISS, Champaign, Ill.) integrated with an inverted Nikon Eclipse TE300 fluorescence microscope (Nikon Ins Tech Co., Ltd., Kanagawa, Japan).

A mode-locked Tsunami Titanium-Sapphire laser pumped with a 5W Millennia VIs (Spectra-Physics, Mountain View, Calif.) was used as a two-photon excitation light source. The Tsunami operates at 80 MHz with a 100-fs pulse width and is tunable between 700 nm and 1000 nm. The laser beam is expanded with a High Laser Beam Expander HB-4X-AR.16 coated for the 650-1000 nm region (Newport Corp., Irvine, Calif.) to overfill the back aperture of a Nikon Plan Apo 60X/1.2W objective, creating a diffraction-limited focal spot.

A dichroic mirror (700DCSPXR, Chroma Technology Corp., Rockingham, Vt.) is installed in the microscope to direct the excitation beam to the sample and the emission fluorescence light to the detector(s). In addition, a band pass filter (E700sp-2p, Chroma Technology) is placed before the detectors to further reduce any leakage of the excitation light.

The detection box (Alba box) consists of two SPCM-AQR-15-Si APD Single Photon Counting Modules with <50 dark counts/second (Perkin Elmer Inc., Fremont, Calif.) aligned perpendicularly. When performing DC-FCCS measurements, an additional dichroic mirror Q5651p and two band-pass filters HQ535/50, HQ645/75 (all Chroma Technology) were placed in the light pass before detectors.

A unique ISS-developed FCS data acquisition card (ISS, Champagne, Ill.) stores all the raw data, which can be utilized for further analysis or removal of bad data points. Other features of the card include the ability to simultaneously store data from two channels separately, and to collect data as short as 40 nanoseconds (ns) or as long as 1.3 milliseconds (ms).

The size of the excitation volume was calibrated using an analytically-prepared 35 nM solution of Rhodamine110 (Molecular Probes, Eugene, Oreg.). The autocorrelation curve calculated from the FCS data was fit with the single component model and the Rhodamine110 diffusion coefficient equal to 270 μm²/s. Typically, the resultant ω value and the $Z_0/\omega$ ratio were 0.3 μm and 4, respectively.

DC-FCCS data were processed with Vista FCS software (ISS) using intensity autocorrelation function to calculate the autocorrelation curve.

Samples were placed in a 96-microwell optical bottom plate (Nalge Nunc International, Rochester, N.Y.). The excitation wavelength was set at 810 nm, 3 mW on the sample. Sampling rate was set at 200 KHz and 10 million points were collected for each measurement. Each sample was measured twice. Experiments were performed on each sample after one-hour incubation.

In each antibody pair, one antibody was labeled with a green fluorophore (ALEXA 488), and the other antibody was labeled with a red fluorophore (TexasRed). Labeled antibodies were mixed at equal concentration (40 μL of 10 nM mAbs) and ligand (15 nM NGAL) was added to the solution. Cross-correlation curves before and after adding NGAL were calculated from the data sets acquired in each channel and the data were normalized.

For two channels i and j, the normalized fluorescence cross-correlation function $G_X(\tau)$ is defined below in equation [5] as:

$$G_x(\tau) = \frac{\langle \Delta F_i(t) \cdot \Delta F_j(t+\tau) \rangle}{\langle F_i(t) \rangle \langle F_j(t) \rangle} \quad [5]$$

where the difference $\Delta F_i(t)$ between the observed fluorescence $F_i(t)$ and the average fluorescence value $<F_i>$ expresses the fluctuation in fluorescence intensity in channel i as the function of time t: $\Delta F_i(t)=F_i(t)-<F_i>$. At the decay time $\tau=0$, the extrapolated value of G(0) reflects the amplitude of the auto- or cross-correlation function.

Results of DC-FCCS Experiments

Figure 21:
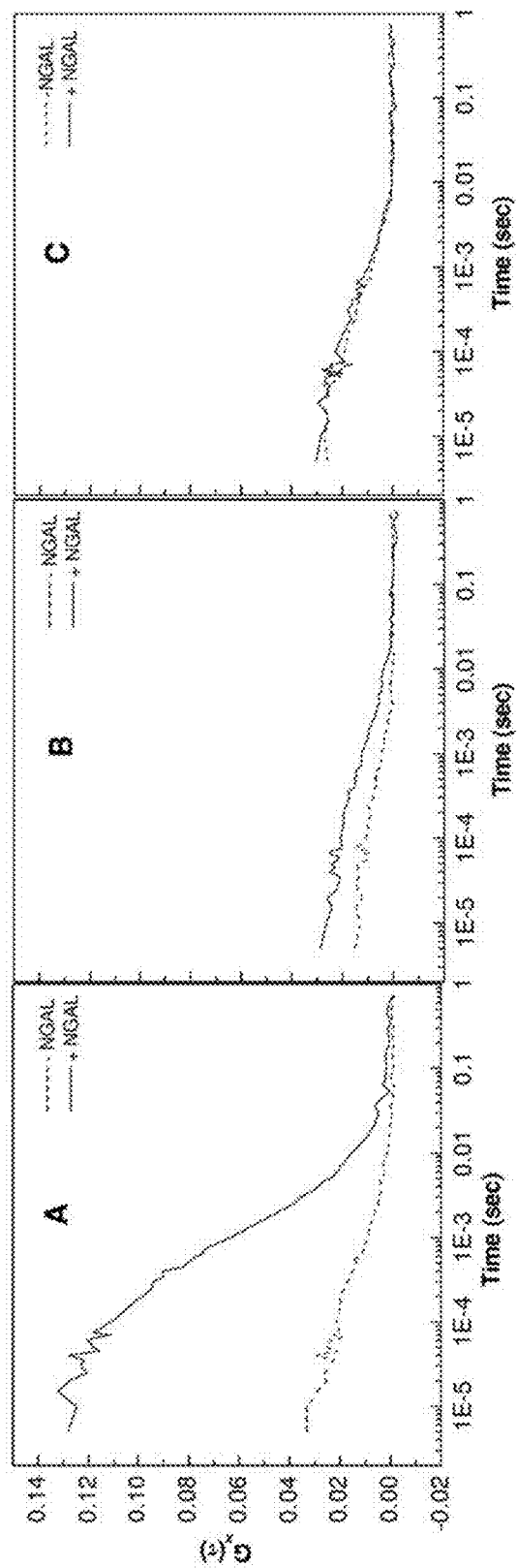
FIGS. 21A-C show the dual channel cross-correlation fluorescence curves for various antibody pairs both before (dotted line) and after (solid line) addition of NGAL with time (seconds, log scale) on the abscissa, and normalized fluorescence cross-correlation function $G_X(\tau)$ on the ordinate.

FIG. 21 shows examples of the cross-correlation curves of three antibody pairs [(A) mAb 2322 and mAb 903; (B) mAb 2322 and mAb 809; (C) mAb 809 and mAb 181)] before and after addition NGAL. The amplitude of the cross-correlation curve is proportional to the concentration of the formed antibody sandwich. Thus, a large increase in the amplitude of the cross-correlation curve and the Gx(0) value suggests productive sandwich formation.

For illustration purposes, a relative number was assigned to each antibody pair, which, in fact, is the ratio of Gx(0) values before and after the addition of NGAL to the antibodies (Table 13). All ratio values were corrected for the background. A value of "1" indicates no sandwich formation, values between 1.1 and 2.5 indicate a poor sandwich formation, and all values above 2.6 indicate productive antibody pairing.

Table 13 below shows the ratio values (background corrected) of Gx(0) before and after adding NGAL to each antibody pair.

TABLE 13

| mAb | 2322 | 809 | 903 |
|---|---|---|---|
| 2322 | 0.7 | 1.5 | 3.5 |
| 181 | 2.1 | 0.9 | 3.6 |
| 269 | 1.2 | 0.9 | 4.0 |
| 809 | 1.5 | 1.0 | 3.5 |
| 903 | 3.7 | 3.0 | 1.0 |
| 419 | 1.6 | 2.6 | 2.0 |

As it follows from Table 13, the results of DC-FCCS experiments are in a good agreement with the NMR perturbations described earlier. Namely, mAb 2322 and other antibodies from the Epitope Group 1 (e.g., mAb 181, mAb 269 and mAb 809) effectively make sandwiches with mAb 903 (Epitope Group 2). In contrast, mAb 419 (Epitope Group 3) is not as effective in sandwich formation with the antibodies from either Group 1 or Group 2.

Example 10

ATCC Deposit Information

As described in U.S. Provisional Application Ser. No. 60/981,470 filed Oct. 19, 2007 (incorporated by reference for its teachings regarding NGAL antigens), the wild-type NGAL rAg CHO 662 cell line was deposited with the American Type Culture Collection (ATCC) at 10801 University Boulevard, Manassas, Va. 20110-2209 on Nov. 21, 2006 and received ATCC Accession No. PTA-8020, and the mutant NGAL rAg CHO C87S cell line (CHO cell clone #734, also known as "mutant C87S NGAL rAg CHO 734) was deposited with the American Type Culture Collection (ATCC) at 10801 University Boulevard, Manassas, Va. 20110-2209 on Jan. 23, 2007 and received ATCC Accession No. PTA-8168.

Murine hybridoma cell lines 1-903-430 and 1-2322-455 were each deposited with the American Type Culture Collection (hereinafter referred to as "A.T.C.C"), 10801 University Blvd., Manassas, Va. 20110-2209, on Nov. 21, 2006. Cell line 1-903-430 was assigned ATCC Accession No. PTA-8026. Cell line 1-2322-455 was assigned ATCC Accession No. PTA-8024.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference. In particular, the following two U.S. patent applications, co-filed with the present disclosure, are incorporated by reference in their entireties: U.S. Provisional Application Ser. No. 60/981,470 filed Oct. 19, 2007; and U.S. Provisional Application Ser. No. 60/981,473 filed Oct. 19, 2007.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as encompassed by the appended claims. Moreover, it should be understood that where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

---

What is claimed is:

1. An isolated antibody comprising a complementary determining region (CDR) heavy chain 1, a CDR heavy chain 2, a CDR heavy chain 3, a CDR light chain 1, a CDR light chain 2, and a CDR light chain 3, wherein the CDR heavy chain 1 comprises an amino acid sequence of SEQ ID NO:8, the CDR heavy chain 2 comprises an amino acid sequence of SEQ ID NO:9, the CDR heavy chain 3 comprises an amino acid sequence of SEQ ID NO:10, the CDR light chain 1 comprises an amino acid sequence of SEQ ID NO:12, the CDR light chain 2 comprises an amino acid sequence of SEQ ID NO:13 and the CDR light chain 3 comprises an amino acid sequence of SEQ ID NO:14, wherein the antibody specifically binds to human NGAL protein.

2. The antibody according to claim 1, wherein the human NGAL protein comprises an amino acid sequence of SEQ ID NOS: 1, 2, 30 or 33.

3. The antibody according to claim 1, wherein said antibody is a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

4. The antibody of claim 1, wherein the antibody is a fully humanized antibody, a partially humanized antibody, a chimeric antibody, a single-chain Fv, a single chain antibody, a single domain antibody, a Fab fragment, a F(ab')$_2$ fragment, or a disulfide-linked Fv.

5. The antibody of claim 1, wherein the antibody comprises a detectable label.

6. The antibody of claim 1, wherein the antibody is immobilized on a solid phase.

7. A kit comprising the antibody of claim 1.

8. The kit of claim 7, wherein the kit additionally comprises a pretreatment reagent.

9. An isolated antibody comprising a complementary determining region (CDR) heavy chain 1, a CDR heavy chain 2, a CDR heavy chain 3, a CDR light chain 1, a CDR light chain 2, and a CDR light chain 3, wherein the CDR heavy chain 1 comprises an amino acid sequence of SEQ ID NO:18, the CDR heavy chain 2 comprises an amino acid sequence of SEQ ID NO:19, the CDR heavy chain 3 comprises an amino acid sequence of SEQ ID NO:20, the CDR light chain 1 comprises an amino acid sequence of SEQ ID NO:22, the CDR light chain 2 comprises an amino acid sequence of SEQ ID NO:23 and the CDR light chain 3 comprises an amino acid sequence of SEQ ID NO:24, wherein the antibody specifically binds to human NGAL protein.

10. The antibody according to claim 9, wherein the human NGAL protein comprises an amino acid sequence of SEQ ID NOS: 1, 2, 30 or 33.

11. The antibody according to claim 9, wherein said antibody is a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

12. The antibody of claim 9, wherein the antibody is a fully humanized antibody, a partially humanized antibody, a chimeric antibody, a single-chain Fv, a single chain antibody, a single domain antibody, a Fab fragment, a F(ab')$_2$ fragment, or a disulfide-linked Fv.

13. The antibody of claim 9, wherein the antibody comprises a detectable label.

14. The antibody of claim 9, wherein the antibody is immobilized on a solid phase.

15. A kit comprising the antibody of claim 9.

16. The kit of claim 15, wherein the kit additionally comprises a pretreatment reagent.

17. The kit of claim 15, wherein the kit additionally comprises the antibody of claim 9.

18. A method for detecting the presence of human NGAL antigen in a test sample, said method comprising:
   (1) contacting a test sample suspected of containing human NGAL with an immunodiagnostic reagent for a time and under conditions that allow formation of a human NGAL/antibody complex; and
   (2) detecting any human NGAL/antibody complex formed as indicating the presence of said human NGAL antigen, wherein said immunodiagnostic reagent comprises one or more antibodies as set forth in claim 1 and claim 9.

19. The method of claim 18, wherein the immunodiagnostic reagent is immobilized on a solid phase.

20. The method of claim 18, wherein the immunodiagnostic reagent comprises a detectable label.

21. The method of claim 20, wherein the detectable label is selected from the group consisting of a radioactive label, an enzymatic label, a chemiluminescent label, a fluorescence label, a thermometric label, and an immuno-polymerase chain reaction label.

22. The method of claim 20, wherein the detectable label is acridinium.

23. The method of claim 18, wherein the method is adapted for use in an automated system or semi-automated system.

24. A method for detecting the presence of human NGAL antigen in a test sample, comprising:
   (a) contacting a test sample suspected of containing human NGAL with at least one first antibody so as to form a first antibody/human NGAL complex, wherein said at least one first antibody binds to human NGAL and is an antibody selected from the group consisting of an antibody of claim 1 and an antibody of claim 9;
   (b) contacting said first antibody/human NGAL complex with a second antibody that binds to human NGAL so as to form a second antibody/human NGAL/first antibody complex, wherein said second antibody differs from said first antibody and is an antibody selected from the group consisting of an antibody of claim 1 and an antibody of claim 9; wherein the first antibody or the second antibody comprises a detectable label; and
   (c) determining the amount of the second antibody/human NGAL/first antibody complex formed in step (b), thereby detecting the presence of human NGAL antigen in the test sample.

25. The method of claim 24, wherein the first antibody is immobilized on a solid phase.

26. The method of claim 24, wherein the detectable label is selected from the group consisting of a radioactive label, an enzymatic label, a chemiluminescent label, a fluorescence label, a thermometric label, and an immuno-polymerase chain reaction label.

27. The method of claim 24, wherein the detectable label is acridinium.

28. The method of claim 24, wherein the method is adapted for use in an automated system or semi-automated system.

* * * * *